(12) United States Patent
Clark et al.

(10) Patent No.: US 7,265,262 B2
(45) Date of Patent: Sep. 4, 2007

(54) TELOMERIZING NUCLEAR DONOR CELLS AND IMPROVING THE EFFICIENCY ON NUCLEAR TRANSFER

(75) Inventors: A. John Clark, Midlothian (GB); Wei Cui, Midlothian (GB); Chris Denning, Loughborough (GB); Debbiao Zhao, Midlothian (GB)

(73) Assignee: Roslin Institute (Edinburgh), Roslin, Midlothian (GB)

( * ) Notice: Subject to any disclaimer, the term of this patent is extended or adjusted under 35 U.S.C. 154(b) by 193 days.

(21) Appl. No.: 10/105,616

(22) Filed: Mar. 21, 2002

(65) Prior Publication Data

US 2003/0175967 A1   Sep. 18, 2003

Related U.S. Application Data

(60) Provisional application No. 60/277,749, filed on Mar. 21, 2001.

(51) Int. Cl.
*C12N 15/00* (2006.01)
(52) U.S. Cl. .......................................... 800/24; 435/455
(58) Field of Classification Search ............. 435/320.1, 435/455, 462, 463, 375; 800/24
See application file for complete search history.

(56) References Cited

U.S. PATENT DOCUMENTS

| | | | | |
|---|---|---|---|---|
| 4,959,317 | A | 9/1990 | Sauer | 435/172.3 |
| 5,698,763 | A | 12/1997 | Weissmann et al. | 800/2 |
| 5,821,117 | A | 10/1998 | Sandrin et al. | 435/320.1 |
| 5,849,991 | A | 12/1998 | d'Apice et al. | 800/2 |
| 5,929,301 | A | 7/1999 | Baszcynski et al. | 800/278 |
| 6,147,276 | A | 11/2000 | Campbell et al. | 800/24 |
| 6,252,133 | B1 | 6/2001 | Campbell et al. | 800/24 |
| 6,261,836 | B1 | 7/2001 | Cech et al. | 435/325 |

FOREIGN PATENT DOCUMENTS

| | | |
|---|---|---|
| AU | 678234 | 11/1994 |
| WO | WO98/39416 | 9/1998 |
| WO | WO 99/21415 | 5/1999 |
| WO | WO99/21415 | * 5/1999 |
| WO | WO99/27113 | 6/1999 |
| WO | WO99/46982 | 9/1999 |
| WO | WO 00/25578 | 5/2000 |
| WO | WO 00/31237 | 6/2000 |
| WO | WO 00/31238 | 6/2000 |
| WO | WO 01/00650 | 1/2001 |
| WO | WO 01/42421 | 6/2001 |

OTHER PUBLICATIONS

Simerly, C. et al. Molecular Correlates of Primate Nuclear Transfer Failures. Science. Apr. 11, 2003, vol. 300, p. 297.*
Mitalipov et al. Rhesus Monkey Embryos Produced by Nuclear Transfer from Embryonic Blastomeres or Somatic Cells. Biology of Reproduction. 2002, vol. 66, pp. 1367-1373.*
Meirelles et al. Complete Replacement of the Mitochondrial Genotype in a Bos indicus Calf Reconstructed by Nuclear Transfer to a Bos taurus Oocyte. Genetics 2001, vol. 158, pp. 351-356.*
Fehilly et al. Cytogenic and Blood Group Studies of Sheep/Goat Chimaeras. J. Reproduct. Fertility. 1985, vol. 74, pp. 215-221.*
Cibelli et al. Cloned Transgenic Calves Produced from Nonquiescent Fetal Fibroblasts. Science. May 22, 1998, vol. 280, pp. 1256-1258.*
Bodnar et al. Extension of Life-Span by Introduction of Telomerase Into Normal Human Cells. Science. Jan. 16, 1998, vol. 279, pp. 349-352.*
Yang et al. Human Endothelial Cell Life Extension by Telomerase Expression. Journal of Biological Chemistry. Sep. 10, 1999, vol. 274, pp. 26141-26148.*
Denning, C. et al. Gene Targeting in Primary Fetal Fibroblasts from Sheep and Pig. Cloning and Stem Cells. 2001, vol. 3, pp. 221-231.*
Cui et al. Telomerase-Immortalized Sheep Fibroblasts Can Be Reprogrammed by Nuclear Transfer to Undergo Early Development. Biol. Reprod. 2003, vol. 69, pp. 15-21.*
Bodnar et al., Extension of life-span by introdution of telomerase into normal human cells, Science 279:349 (1998).
Campbell et al., Sheep cloned by nuclear transfer from a cultured cell line, Nature 380:64 (1996).
Clark et al., Gene targeting in livestock: a preview, Transgenic Res. 9:263 (2000).
Clark, Gene expression in the mammary glands of transgenic animals, Biochem. Soc. Symp. 63:133 (1998).
Clark, The mammary gland as a bioreactor: expression, processing, and production of recombinant proteins, Mammary Gland Biol. Neoplasia 3:337 (1998).
Goldmann, et al., Two alleles of a neural protein gene linked to scrapie in sheep, Proc. Natl. Acad. Sci. USA 87:2476 (1990).
Jiang et al., Telomerase expression in human somatic cells does not induce changes associated with a transformed phenotype, Nat. Genet. 21:111 (1999).
Kim et al., Specific association of human telomerase activity with immortal cells and cancer, Science 266:2011 (1997).

(Continued)

*Primary Examiner*—Deborah Crouch
(74) *Attorney, Agent, or Firm*—Finnegan, Henderson, Farabow, Garrett & Dunner, LLP

(57) ABSTRACT

This disclosure provides a system for creating cloned cells and embryos that are genetically modified. Cells are treated to increase expression of telomerase and potentially extend replicative capacity. One or more genetic modifications is made to inactivate a gene or confer desirable features, growing and selecting the cells as needed. The modified nucleus can then be transferred to a suitable recipient cell, which can then be used to grow an embryo with the conferred attributes. This technology makes it possible to create embryos, animals and embryonic cell lines with multiple genetic modifications, including homozygously inactivated genes and gene substitutions.

32 Claims, 8 Drawing Sheets

OTHER PUBLICATIONS

Wilmut et al., Viable offspring derived from fetal and adult mammalian cells, Nature 385:810 (1997).

Roslin Signs Six Year Deal With geron, Roslin Biomed Press Release (1999).

Annual Report, Roslin Institute Edinburgh 98-99.

Solter, D., Mammalian cloning: advances and limitations, Nat Rev Genet. 1:199 (2000) Review.

Yang, et al., Human endolethial cell life extension by telomerase expression, J Biol Chem. 274:26141 (1999).

Australian Provisional Patent Application PR 1109, A Novel Cell Type for NuclearTransfer.

* cited by examiner

TELOMERIZING NUCLEAR DONOR CELLS AND IMPROVING THE EFFICIENCY ON NUCLEAR TRANSFER

RELATED APPLICATIONS

This application claims priority benefit of U.S. provisional patent application 60/277,749, filed Mar. 21, 2001, pending. The priority application is hereby incorporated herein by reference in its entirety, as are U.S. Ser. No. 60/277,811 and issued U.S. Pat. Nos. 6,147,276, 6,252,133, and 6,261,836.

TECHNICAL FIELDS

This invention relates to the field of nuclear transfer between cells and animal cloning. The invention also relates generally to the field of cell senescence and increasing replicative capacity using telomerase reverse transcriptase.

BACKGROUND

Animals were first cloned from adult cells by Keith Campbell and Ian Wilmut at the Roslin Institute, U.K. This seminal work has been described in U.S. Pat. No. 6,147,276, International Patent Applications WO 97/07669 and WO 97/07668, and in Wilmut et al., Nature 385:810, 1997. The technique involves transferring the nucleus of a cell from the animal to be cloned into a suitable recipient cell. It is thought that the recipient cell causes the genes in the nucleus to be expressed in such a way that a program of embryonic development begins anew. The embryo is then implanted into a surrogate carrier animal for gestation into a viable offspring.

Subsequent to this teaching, other scientists have succeeded in cloning from adult cells. U.S. Pat. No. 5,994,619 reports production of chimeric bovine or porcine animals using cultured inner cell mass cells. U.S. Pat. No. 6,011,197 relates to a method for cloning cows by reprogramming non-embryonic bovine cells using leukocyte inhibitory factor (LIF) and fibroblast growth factor (FGF), then transferring the nucleus into an enucleated oocyte. International Patent Publication WO 99/21415 reports nuclear transfer for production of transgenic animal embryos. WO 99/05266 and WO 00/52145 propose trans-species nuclear transfer, using bovine oocytes as the recipient cell for a nucleus taken from the donor cell of a different species. WO 99/36510 reports efficient nuclear transfer using fetal fibroblasts. WO 00/25578 proposes a cloning method in which an oocyte is chemically enucleated by exposure to a compound that destabilizes a meiotic spindle apparatus in the recipient cell. WO 00/31237 and WO 99/46982 outline methods for cloning pigs. WO 00/74477 propose a process for animal cloning in which somatic cells denatured by heating are transferred into enucleated metaphase II oocytes. WO 01/00795 describes surgical methods useful for obtaining oocytes from cows for cloning.

Loi et al. (Reprod. Nutr. Dev. 38:615, 1998) discuss embryo transfer and related technologies in sheep reproduction. Wells et al. (Biol. Reprod. 57:385, 1997) report production of cloned lambs from an established embryonic cell line. Liu et al. (Mol. Reprod. Dev. 47:255, 1997) discuss the effect of cell cycle coordination between nucleus and cytoplasm and the use of in vitro matured oocytes in nuclear transfer in sheep embryos. Campbell et al. (Nature 380:65, 1996) report sheep cloned by nuclear transfer from an established cell line.

There is considerable promise in this field for cell therapy and adaptive agriculture. Until the technique of nuclear transfer was developed, genetically modified livestock were made by pronuclear injection (Clark et al., Transgenic Res. 9:263, 2000). Using this methodology, the nucleus of an embryonic cell can be transfected to place a new recombinant gene into the genome of the animal. The new transgene can have any one of a number of desired effects—such as causing secretion of a therapeutic protein into milk, which can then serve as a bioreactor for commercial production (A. J. Clark, Biochem. Soc. Symp. 63:133, 1998, and J. Mammary Gland Biol. Neoplasia 3:337, 1998).

The discovery that animals can be cloned by nuclear transfer from cultured somatic cells provides a new avenue for making animals with a modified genome.

SUMMARY

This disclosure provides a system for facilitating the creation of cloned cells and embryos that have been genetically modified. Cells are obtained that are suitable for nuclear transfer, and treated to increase expression of telomerase and potentially extend replicative capacity. One or more genetic modifications can then be made to confer desirable features, growing and selecting the cells as needed, which is facilitated by the effect of telomerase on the cells. The modified nucleus is then transferred to a suitable recipient cell, which can then be used to grow an embryo with the conferred attributes.

One embodiment of the invention is a method for producing a vertebrate cell with an altered genome by increasing telomerase activity in the cell at some point in the process of altering the genome.

Using this technique, multiple alterations to the genome are possible, including alterations to one or both alleles of a particular gene, or introducing transgenes at random locations, in any desired combination. Methods are provided in this disclosure to inactivate or replace the encoding region of a particular gene by homologous recombination or some other technique, and then selecting targeted clones by combinations of drug selection, mRNA analysis, or phenotype-based separation. Throughout this disclosure, it is understood that the altered cell can be expanded at any point in the process, and that multiple alterations to one cell is equivalent to alterations made sequentially to progeny of the cell.

Telomerase activity can be increased by expressing an encoding region for telomerase reverse transcriptase in either a transient or permanent fashion. If the TERT sequence is integrated into the genome in an expression cassette or as part of a targeting vector, it can later be removed by flanking the sequence with recombinase recognition sites.

Another embodiment of the invention is a method for producing a chimeric cell by nuclear transfer. A genetically altered donor cell is prepared according to the invention, and the nucleus is then transferred to a recipient cell suitable for chromatin remodeling or reprogramming, thereby permitting an embryo or pluripotent stem cell to be obtained. An embryo produced by this procedure can be used to birth a vertebrate animal by implanting into a suitable carrier. A major advantage of this strategy is that several genetic alterations can be produced in the embryo or animal in a single generation. The techniques of this invention may be brought to bear on any vertebrate species, amongst which livestock species such as sheep, cows, and pigs are exemplary.

Other embodiments of the invention are cells, embryos, and animals produced according to these methods. The cell, embryo or animal may have a normally expressed diploid gene which is inactivated or contains an artificially introduced genetic alteration. Where different targeting vectors are used, the gene may have a different alteration on each allele. A further embodiment of the invention is a cell line that has an increased level of telomerase activity or TERT expression, elected for high relative frequency of successful genetic targeting and is suitable as a donor for nuclear transfer.

Also embodied in the invention is a vector for homologous recombination in a eukaryotic cell, comprising a TERT encoding region for insertion into the genome. Homologous recombination is effected by way of other sequences in the vector that are highly homologous with genomic DNA to which it is targeted. The targeting site can be selected to inactivate an endogenous gene—such as the prion protein (PrP) gene, or the α(1,3)galactosyltransferase gene. This allows the cell to be targeted and telomerized at the same time, which improves replicative capacity of the cells and enhances genomic stability. The vector can have other features that enhance its use for nuclear transfer. For example, the TERT encoding region or a drug resistance gene can be is flanked on either side by recognition sites for a site-specific recombinase, to allow these sequences to be removed after genetic modifications are complete and the cell is being readied for nuclear transfer.

These and other aspects of the invention will be apparent from the description that follows.

DRAWINGS

FIG. 1 is a map of plasmid pGRN145, which causes cells to express telomerase reverse transcriptase (abbreviated here as hTRT), the limiting component of telomerase activity in most mammalian cells. Transcription is under control of the myeloproliferative sarcoma virus (MPSV) promoter.

FIG. 2 is a map of the adapted telomerizing plasmid PWpGB5. The MPSV promoter controls expression of the gene for telomerase reverse transcriptase (hTRT), followed by IRES sequences, and the puromycin selection gene. This entire region is flanked by loxP sequences, which allows the cassette to be excised from the genome after genetic manipulation and before expansion or nuclear transfer.

FIG. 3 is a graph showing the growth of primary sheep fibroblasts transduced to express telomerase reverse transcriptase. Each line is a single clone, except BW6F2, which is the parental (untransfected) fibroblast line. ○=telomerase-expressing clones; ▲=telomerase-negative clones; ■=clones that were telomerase-negative initially, but became positive later. All telomerase-negative clones became senescent towards the end of the growth curve, but cells with telomerase activity continued growing beyond 200 doublings.

FIG. 4 is a photocopy of light micrograph of cloned sheep fibroblasts stained with X-gal for cell senescence. Telomerase negative clones are in the left panels, and contain >10% positive cells. Cells expressing hTERT, shown on the right, did not stain positively even when carried to ~256 doublings.

FIG. 5 is a half-tone reproduction showing vectors used for gene inactivation in sheep fibroblasts. They are targeted to inactivate the α(1,3)galactosyltransferase (GGTA) and prion protein (PrP) genes by homologous recombination. Successful targeting creates PCR products and Southern blot restriction fragments of different size. Results from clones shown on the right are for the unaltered wild-type cells (−), and cells with a gene knockout on one of the two alleles (+).

FIG. 6 is a photocopy of a gel, showing results of targeting telomerized sheep fibroblasts with the α1,3GT targeting vector. Lanes: 1-5, PCR products using primers for the neo gene; Lanes 6-10, PCR products using primers for the α1,3GT sequence. Lanes 1, 2, 7, & 8 is clone B9; Lanes 3, 4, 8, & 9 is clone C9; Lanes 5 & 10 is a positive targeting control. Clone B9 shows successful inactivation of the α1,3GT gene.

FIG. 7 is a map of the two promoter-less neo PrP gene knockout targeting vectors for targeting the sheep PrP gene. The vectors contain the hTERT gene in forward or reverse orientation, under control of the PGK promoter. These vectors can be used to inactivate the PrP gene and simultaneously telomerize the cells for further genetic manipulation and improved nuclear transfer efficiency.

Figure 10:
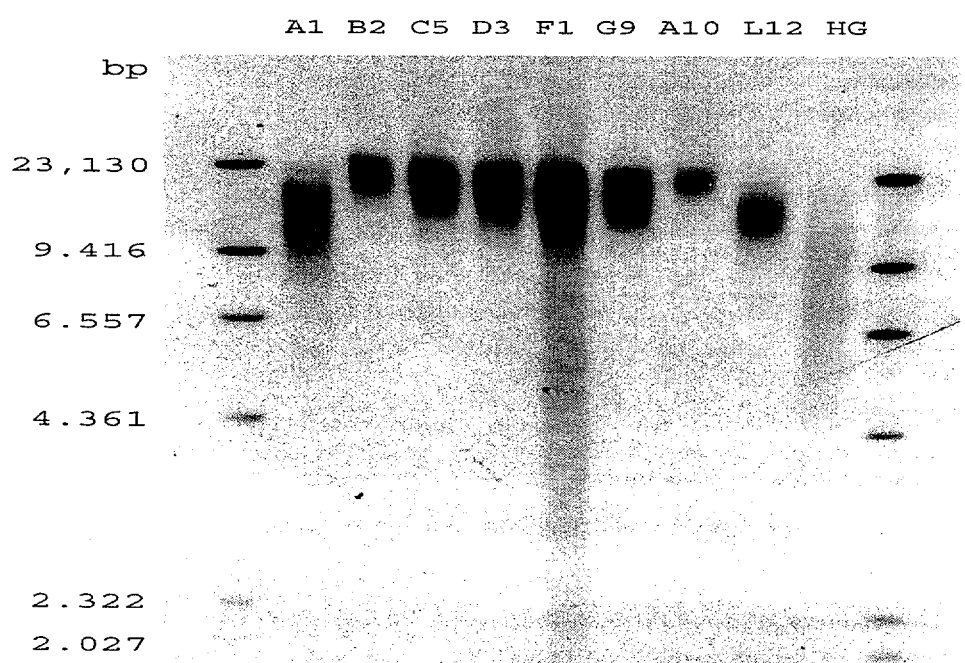

FIG. 10 is a half-tone reproduction of analysis for telomere restriction fragments (TRF) of targeted and non-targeted cell lines. Both the parental line (A1) and cells targeted without telomerization (L12) showed shortened telomeres. However, the lines that were targeted and telomerized simultaneously retained long TRF, indicating they retain replicative capacity and genomic stability.

DETAILED DESCRIPTION

In creating genetically modified animals, it is sometimes desirable to inactivate a gene that is normally expressed. This is a more difficult problem than turning on expression of a new gene—which can be accomplished by placing a single copy of the new gene into any transcribable site in the genome of the embryonic cell. To turn off expression of an endogenous gene, a specific locus in the genome must be targeted for genetic alteration. Furthermore, the gene usually must be targeted on both alleles before the desired phenotype is attained.

The availability of techniques for cloning by nuclear transfer considerably enhances the opportunity for producing genetically modified animals. The somatic donor cell is established in culture, and subjected to genetic modification and selection. The nucleus from the selected cell is then transferred to a suitable recipient cell that initiates formation of the embryo.

In experiments where particular genes were targeted in sheep cells by homologous recombination described below in the Example section, it was found that cells successfully targeted on one allele according to standard techniques may be suitable for nuclear transfer at only a low frequency. In order to obtain a phenotypic knockout, it would be necessary to bring the cloned animal to term, and then breed animals carrying the knockout on one allele until a homologous knockout animal is obtained.

It has now been discovered that the frequency of obtaining genetically modified cells suitable for nuclear transfer can be improved by increasing the expression of functional telomerase. The presence of active telomerase was found to have a number of important effects:

1. It increases the replicative capacity of the cell sufficiently to extend the genetic manipulation process—which can now include more extensive cell selection, and/or multiple serial genetic modifications on the same cell line. This substantially improves
2. It was found to improve the frequency of obtaining cell lines that have been successfully targeted by homologous recombination. As illustrated below, the usual frequency of targeting events is typically less than 1 in 100 cells, with only 1 in 10 of those cells forming cell lines. The presence of active telomerase apparently enhances the outgrowth and recovery of selected cells.
3. Unexpectedly, it also appears to increase the frequency of successful nuclear transfer. When the nucleus of one cell is transferred to a suitable recipient, active telomerase can in certain circumstances improve the probability that the reconstituted cell can be activated to grow into an embryo. This may be attributable to an effect of telomerase on enhancing or facilitating the chromosome remodeling that occurs during reprogramming of the nucleus in the recipient cell.

These effects need not all be present or understood in order to practice the invention, but may assist the reader in understanding the approach being taken.

The invention is particularly powerful to achieve more than one genetic modification in a single generation. In particular, homozygous knockout cells can be created in which the gene is modified either simultaneously or sequentially on both alleles. For example, the gene can be targeted with one vector comprising a drug resistant gene, and selected using the corresponding drug. The gene is then targeted with a second vector comprising a second drug resistant gene, and selected using the second drug. The surviving cell can be used to clone an animal that is modified on both alleles, without having to inter-breed to obtain the desired trait. In this illustration, the genome of the cell (and the cloned animal) will contain a different artificial genetic modification in each allele (i.e., the two different drug-resistant genes). This can be used, for example, to create homozygously inactivated genes, and genes that have been inactivated on one allele, and modified or substituted on the other.

The proliferative capacity is increased using telomerase to facilitate genetic modifications of this sort, but is typically not required subsequently. Where telomerase activity is increased by genetic transfection, this invention also provides for removing the transfecting gene after the other genetic modifications are complete. If the transfecting gene is integrated into the genome of the cell, it can be flanked with recombination sites and removed at an appropriate time by site-specific recombination.

Definitions

For purposes of this disclosure, an "endogenous" gene refers to a genetic locus that naturally occurs in the cell of a vertebrate species, in its normal context in an unaltered form. The gene may or may not include one or more encoding regions, one or more control elements, and internal or flanking untranscribed or untranslated regions. An endogenous gene element (such as a promoter) that is part of the endogenous gene can remain functional in a modified gene (for example, by linking to a new encoding region).

A "naturally expressed" gene is capable of being transcribed into a functional gene product (such as a biologically active protein or RNA molecule) in at least one cell type of an animal having it in its genome.

An endogenous gene in a cell or animal is said to be "modified" when the DNA sequence of the gene has been modified by recombinant means to alter the molecular or biological function of the gene or gene product in some measurable way.

An endogenous gene in a cell or animal is said to be "inactivated" when it is rendered incapable of transcribing a functional protein. For example, an inactivated gene may be missing necessary transcription or translation control elements, it may be lacking an essential part of the protein encoding region, or the encoding region may be placed out of phase. In another example, the gene may be interrupted by an inserted sequence, or mutated in such a way as to interfere with transcription or translation of the gene product. In a third example, the inactivated gene may produce a translation product that has been altered in such a way that it lacks important enzymatic activity of the native gene product. A gene is also "inactivated" when the normal encoding region is switched with an encoding region for a different gene product with a different biological function.

In the descriptions of genetic modification and inactivation in this disclosure, it is understood that changes to the genome of a cell are inherited by progeny of the cell, unless further genetic manipulation occurs. Thus, it is possible to select the modified cells, let them proliferate, and then make a subsequent modification to the progeny. A sequence of genetic modifications made to cell and its ancestors are considered equivalent to making all the modifications to the same cell, unless explicitly directed otherwise.

A cell is said to be "transfected", "genetically transformed", or "genetically altered", when the cell has been introduced with a recombinant polynucleotide, or is the progeny of such a cell that has inherited the polynucleotide. The alteration may (but need not) be integrated into the genome of the cell. Non-limiting examples include the following: 1. A cell containing a vector with a sequence encoding a protein of interest, capable of causing the protein to be expressed by the cell on a transient or inheritable fashion; 2. A cell containing a genetic construct for targeting an endogenous gene (whether or not the gene has been successfully targeted); and 3. A cell containing a genetic modification introduced by recombinant means.

The genetic alteration is said to be "inheritable" if progeny of the altered cell has the same alteration. Determination of whether the genetic alteration is inheritable can be made by detecting presence of the polynucleotide template (e.g., by PCR amplification), or by detecting a phenotypic feature (such as expression of a gene product or effect thereof) that depends on the genetic alteration to be manifest.

An "alteration to the genome" of the cell refers to a change in sequence of chromosomal DNA (a deletion, insertion, or mutation) introduced by artificial manipulation of the cell, particularly by recombinant DNA technology. The change will be inheritable by progeny of the cell acquiring the altered chromosome, by chimeras made by transferring the nucleus of the cell to a suitable recipient cell, and by embryos or animals grown from them.

A cell is described as "telomerized" if it has been treated to increase the expression of telomerase reverse transcriptase (TERT) and/or functional telomerase activity by any suitable means beyond the level usually expressed by cells of the same type in the same environment. Methods for telomerizing cells are illustrated in a later section of this disclosure. The term also applies to progeny of the originally treated cell that have inherited the ability to express telomerase at an elevated level.

The terms "polynucleotide" and "oligonucleotide" are used interchangeably to refer to a polymeric form of nucleotides of any length. Included are genes and gene fragments, mRNA, cDNA, plasmids, vectors, synthetic nucleic acids, targeting constructs, nucleic acid probes, and primers.

A "control element" or "control sequence" is a nucleotide sequence involved in an interaction of molecules that contributes to the functional regulation of a polynucleotide, such as replication, duplication, transcription, splicing, or translation. Transcriptional control elements include promoters and enhancers.

The term "embryo" as it is used in this disclosure refers to an organism developing from a fertilized ovum or its equivalent generated by nuclear transfer technology. This includes an embryo growing in utero, and an early embryo growing in tissue culture before engrafting into a carrier. The terms "engrafting" or "transplanting", in reference to embryo manipulation, refer to any known process for artificially introducing one or more embryos into the uterus of a female animal.

The term "tissue" refers to a heterogeneous collection of cells responsible for maintaining one or more physiological functions. Of interest for certain embodiments of this invention are organs suitable for transplantation, such as a whole kidney; however, the term also includes organ fragments and other embodiments, such as a piece of connective tissue, or a collection of cells in a medical support device.

This invention can be practiced on cells of any vertebrate animal, such as a member of an avian or mammalian species, including but not limited to domestic animals, non-human primates, humans, agricultural livestock, and vertebrates suitable for growing biological compounds or tissue for human therapy.

General Techniques

For further elaboration of general techniques useful in the practice of this invention, the practitioner can refer to standard textbooks and reviews in cell and molecular biology, tissue culture, embryology, and veterinary and human medicine.

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology* and *Short Protocols in Molecular Biology*, 3rd Edition (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

Texts that describe reproductive techniques and embryo transfer in animals include *Manual of the International Embryo Transfer Society: A procedural guide and general information for the use of embryo transfer technology emphasizing sanitary procedures*, 3$^{rd}$ ed. (Stringfellow et al., Savoy, Ill.: International Embryo Transfer Society, Savoy Ill.); and *Embryo transfer in farm animals: A review of techniques and applications* (K. J. Betteridge, ed., Agriculture Canada Monographs No. 16, Ottawa, 1977).

Increasing Telomerase Activity in the Nuclear Donor

Donor cells for genetic manipulation according to this invention are typically nucleated cells of the desired species with a germ line genotype, selected to be easily maintained in culture. Exemplary are primary fibroblast cells, which are relatively easy to prepare for most species. For example, cells are collected from sheep or pig fetuses at about 35 days of gestation, and subjected to mild trypsin/EDTA solution, then cultured in a suitable culture medium. Except where explicitly directed otherwise, the techniques of this invention can be applied to any cell type without restriction, including embryonic cells, primary cells from a fetus, offspring, or adult, and established cell lines from any vertebrate.

The replicative capacity of the nuclear donor cell is increased by increasing telomerase activity. This assists the cells in maintaining telomere length, thereby expanding the replicative capacity (the number of cell doublings possible before reaching the Hayflick limit and entering crisis). Typically, telomerase activity is modified before inactivation of the target gene, but such modifications are also permitted at a later stage in the procedure.

Increasing telomerase activity can be accomplished by a number of strategies, including but not limited to the following:

a) genetically altering the cell with a nucleotide having an encoding region for telomerase reverse transcriptase (TERT);
b) artificially placing TERT protein or telomerase holoenzyme into the cell;
c) altering TERT expression from the endogenous gene; or
d) altering expression of a telomerase related protein, thereby effectively increasing telomerase activity.

A convenient method for increasing telomerase activity is to genetically alter the cells so that they express TERT, which is usually the limiting component of telomerase enzyme expression. A TERT gene can be cotransfected with a gene for the telomerase RNA component, or a TERT can be selected that is compatible with the RNA component already expressed by the cell.

It has been discovered that when cells from large mammals such as sheep and pigs are genetically altered with human TERT, they express increased telomerase activity, which indicates that the hTERT gene product can combine with endogenous RNA component to create a functional enzyme. It is a hypothesis of this invention that combinations of mammalian TERT into the cells of other mammals will often be effective.

The human TERT gene sequence is provided in U.S. Pat. No. 6,166,178, which also describes the use of TERT to increase replicative capacity of various cell types. The mouse TERT sequence is provided in International Patent Application WO 99/27113. Other publications with telomerase-related sequences include International Patent Application WO 98/21343 (Amgen); WO 98/37181 (Whitehead); WO 98/07838A1 (Mitsubishi); WO 99/01560 (Cambia), and U.S. Pat. No. 5,583,016 (Geron Corp.). U.S. Pat. No. 5,968,506 describes purified telomerase and methods for obtaining it. When TERT is referred to in this description, it is understood to mean a polypeptide comprising a TERT sequence from any mammalian, vertebrate, or other species, with or without alterations, so long as the polypeptide has telomerase activity when associated with telomerase RNA component, as measured by TRAP assay (described below) in the cell line being treated.

Typically, the vector will comprise a TERT encoding region under control of a heterologous transcription control element that promotes transcription in the intended undifferentiated or differentiated cell line. Sequences that can drive expression of the TERT coding region include viral LTRs, enhancers, and promoters (such as MPSV, SV40, MoLV, CMV, MSCV, HSV TK), eukaryotic promoters (such as β-actin, ubiquitin, elongation factors exemplified by EF1α, and PGK) or combinations thereof (for example, the CMV enhancer combined with the β-actin promoter). Expression of a marker gene can optionally be driven by the same promoter that's driving the TERT gene, either as a separate expression cassette, as part of a polycistronic transcript (in which the coding regions of TERT and the marker gene are separated by an IRES sequence, allowing both individual proteins to be made from a single transcript driven by a single promoter), or as part of the same cassette (a fusion between the coding regions of both TERT and the marker gene, producing a protein that provides the functions of both TERT and the marker gene). Transfection and expression of telomerase in human cells is described in Bodnar et al., Science 279:349, 1998 and Jiang et al., Nat. Genet. 21:111, 1999.

An alternative strategy is to use a vector that substitutes or supplements the promoter in the endogenous TERT gene with a regulatory control element (such as those listed above) that increase expression in the cultured cells. Further illustration of the general strategy of replacing promoters in endogenous genes can be found in U.S. Pat. No. 6,063,630.

When the nucleus of the telomerized cell is transferred to another cell and used to produce a cloned animal or embryo, the tissue will contain alterations to the genome of the donor cell. The presence of a recombinant TERT gene in a donor cell may have other consequences. Accordingly, it may be desirable to provide a mechanism for removing or otherwise inactivating the recombinant TERT gene once the telomeres have been elongated but before nuclear transfer, or before cloned cells are used for another purpose.

This invention provides a mechanism by which the replicative capacity of the nucleus donor cell is enhanced with a telomerase gene during genetic manipulation and selection, but then is removed before nuclear transfer. The telomerase expression cassette is provided in a form that is capable of being passed down during replication, typically by integration into the genome, but adapted for subsequent excision.

This can be accomplished by flanking the TERT gene and/or the transcription control element on both sides with recognition sequences for a site-specific recombinase. Suitable are lox sites recognized by Cre recombinase (U.S. Pat. No. 4,959,317), and frt sites recognized by Flp recombinase (U.S. Pat. No. 5,929,301). Other site-specific recombinases include XerC (Becker et al., Curr. Microbiol. 32:232, 1996), XerD (Subramanya et al., EMBO J. 16:5178, 1997), xisF (Genes Dev. 8:75, 1994), and Int recombinase (Kolot et al., Mol. Biol. Reprod. 36:207, 1999; Tirumalai et al., Proc. Natl. Acad. Sci. USA 94:6104, 1997). An illustrative lox containing TERT vector is provided in Example 1.

Also contemplated are vectors in which a particular gene (such as a selectable marker) is flanked by one type of recombinase recognition site, and the TERT gene or control element is flanked with another type of recognition site. An example is the following:

5'arm-loxP-frt-neopA-frt-pGK promoter-hTERTpA-LoxP-3'arm

This allows the drug resistance marker (neo) to be removed from the line after selection using the first recombinase (Flp), while retaining TERT. Further genetic manipulation can then be performed—for example, targeting the other allele of the same gene, possibly using the same vector and selecting for neo again. After all manipulation is complete, the TERT encoding region can be removed using the second recombinase (Cre).

Another way of obtaining cells with genomic modifications that do not include TERT is to increase telomerase activity without integrating a TERT gene into the genome. For example, TERT can be transiently expressed using a suitable expression system such as adenovirus, or by introducing TERT protein (or the telomerase holoenzyme) directly into the cell. The TERT will be diluted out as the cell divides, but extension of telomeres in the parent cell should increase replicative capacity of the cell line by several doublings.

Another alternative is to upregulate TERT expression from the endogenous gene by upregulating expression of trans-activating transcriptional regulators. The TERT promoter contains a number of regulator recognition sequences, such as c-Myc, SP1, SRY, HNF-3β, HNF-5, TFIID-MBP, E2F and c-Myb. See International Patent Publication WO 00/46355.

A further alternative is not to increase TERT expression, but enhance the effective activity of telomerase already present in the cell. This can be done in cells that have an endogenous level of TERT expression, such as in bone marrow progenitor cells and gonadal tissue. For example, TRF1 and TRF2 are proteins that bind to telomere repeats and regulate access of telomerase (Smogorzewska et al., Mol. Cell Biol. 20:1659, 2000). Decreasing expression of such factors may enhance the ability of telomerase to increase telomere length, thereby increasing replicative capacity of the cell.

Characterizing Cells with Increased Telomerase Activity

Evidence of increased telomerase expression can be obtained by a variety of techniques, including but not limited to determining gene transcript levels (for example, by Northern or RT-PCR analysis), protein expression (for example, by immunocytochemistry), or telomerase activity (for example, by primer extension assay). Extended lifespan or replicative capacity of the treated cells, while often desirable, need not be positively demonstrated for the invention to be put into practice, except where explicitly required.

Telomerase activity can be determined, for example, by TRAP assay (Kim et al., Science 266:2011, 1997; Weinrich et al., Nature Genetics 17:498, 1997), or other suitable technique (e.g., U.S. Pat. No. 5,741,677). Evaluation of hTERT expression by RT-PCR or immunoassay can be done by standard methods, using the sequences disclosed in U.S. Pat. No. 6,166,178. The following assay kits are available commercially for research purposes: TRAPeze® XK Telomerase Detection Kit (Cat. s7707; Intergen Co., Purchase N.Y.); TeloTAGGG Telomerase PCR ELISAplus (Cat. 2,013,89; Roche Diagnostics, Indianapolis Ind.); and Light-Cycler Telo TAGGG hTERT quantification kit (Cat. 3,012,344).

Figure 3:
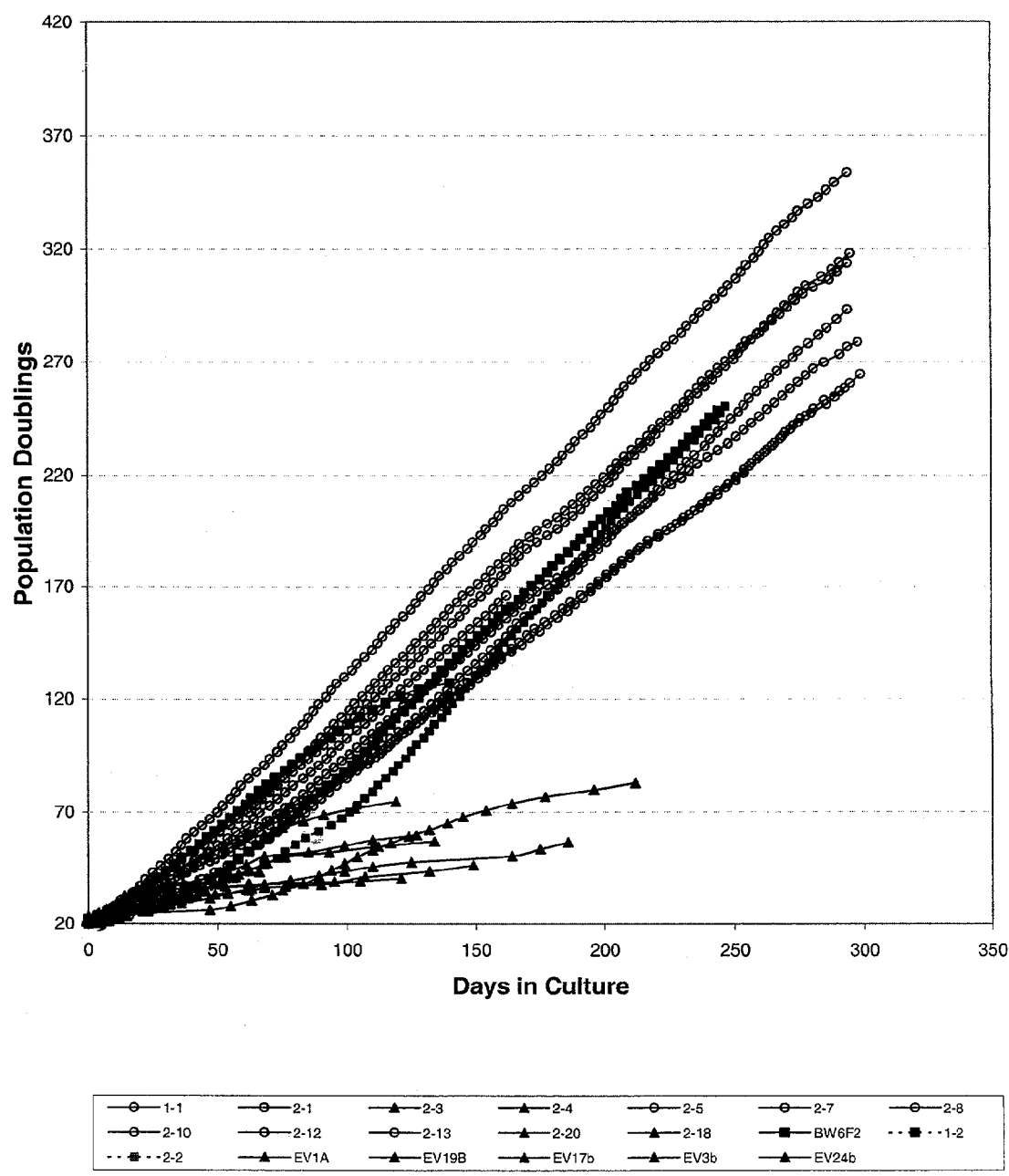

If desired, the cells can also be characterized as to their replicative capacity. This can be determined by passaging cells in a culture environment that supports growth, and monitoring the number of cell doublings. Unmodified fetal fibroblasts will typically grow through a number of doublings until they reach the Hayflick limit, and then enter into senescence. As illustrated in FIG. 3, cells with increased telomerase activity may grow through additional doublings, 10, 25, 100 or more (over 100 doublings for fetal cells; over 50 doublings for adult cells), and may grow indefinitely if TERT continues to be expressed.

The cells can also be characterized by their ability to undergo specific gene targeting. This is determined empirically, according to the purpose for which the cells will ultimately be used. For example, the cells are divided into subpopulations or cloned by limiting dilution, and each line is then sampled and treated using a targeting vector and subsequent drug selection. Selected cells are then expanded, and the number of expanded colonies is quantitated as a proportion of cells in the originally targeted population. A frequency of more than 0.2%, 0.5%, or 2% may be obtainable in certain circumstances.

The cells can also be characterized by their suitability as nuclear donors. This is also determined by empirical methods. For example, cell lines that have proved to have good replicative capacity and/or a high frequency of successful targeting are used as nuclear donors for nuclear transfer into a suitable recipient cell, for example, in the cloning of embryos, as described below. Lines can then be selected for a relatively high frequency of activation of the recipient cell after transfer, or for a relatively high frequency of viable embryo production. A frequency of 2% or 10% may be obtainable in certain circumstances.

Particular embodiments of this invention include cell lines selected for one or more of these attributes in any combination.

Genetically Altering the Target Gene

The genome of the nuclear donor can be altered in any manner that is desirable to have in the recipient cell, or an embryo or tissue made from it. For example, a mutation can be introduced into a native encoding region that corrects a congenital defect or adds some desirable trait. A new encoding region can be integrated into the genome proximal to an endogenous gene element, such as a promoter that will cause it to be expressed in certain cells. Conversely, a new control element can be integrated proximal to an endogenous encoding region, to enhance or redirect its expression.

The techniques of this invention are particularly appropriate for creating gene knockouts, in which a particular gene is inactivated on one or both chromosomes. There is a variety of ways in which a gene can be inactivated. For example, a control element that regulates transcription (such as a promoter or transcription start sequence) can be altered or deleted. Alternatively, the gene can be adapted so that any mRNA that is produced is not translatable into the protein product. This can be effected, for example, by deleting or altering a translation control element, such as a ribosomal binding site or a translation initiation codon. Alternatively, the gene can be adapted so that any protein that is produced lacks the essential features of the endogenous gene product. For example, the encoding region can be interrupted with stop codons, the encoding region can be placed out-of-phase, or critical portions of the protein may be missing, such as a structural component or a signal peptide for secretion. In a further alternative, the gene can be adapted so that the encoded protein no longer has the specificity of the natural gene product—for example, because a change in enzyme activity or ligand binding specificity.

Efficient targeting of the gene typically entails use of a targeting vector, comprising nucleotide sequence identical or nearly identical to a portion of the gene of interest, linked to another structure capable of introducing the alteration. One such method uses homologous recombination, in which a DNA vector comprising homologous regions recombines at the targeted site, substituting its DNA sequence for that of the target. Cloned cells that have been selectively targeted can be identified by PCR amplification of a sequence exclusive to the targeting vector, restriction analysis of the recombination site, or expression phenotype.

Generally it is more convenient to include a selectable marker in the targeting construct, so that targeted cells can rapidly be separated from untargeted cells. U.S. Pat. No. 5,614,396 describes a method for obtaining a cell containing a desired sequence in the cell's genome, by using a targeting vector having two regions homologous to the targeting sequence, flanking a sequence that is to be inserted, and having a selectable marker. The DNA undergoes homologous recombination at the target site, and recombined cells are recovered under selective culture conditions.

Positive selection markers include the neo gene, selectable using G418 or kanamycin; the hyg gene, selectable using hygomycin; the gpt gene, selectable using xanthine, and hypoxanthine-phosphoribosyltransferase (HPRT), selectable using hypoxanthine. Negative selection markers include thymidine kinase (tk), selectable using acyclovir or ganciclovir; HPRT, selectable using 6-thioguanine; and cytosine deaminase, selectable using 5-fluoro-cytosine. Markers can also have an intrinsic label, like green fluorescent protein or β-galactosidase, which permit clones of targeted cells to be identified and selected. Another option is a gene that causes expression of a cell-surface antigen—for example, a transmembrane protein targeted to the plasma membrane, or a glycosyltransferase that causes formation of a surface oligosaccharide determinant. Cells that have incorporated the targeting vector will be selectable using an antibody or lectin specific for the surface determinant by a technique such as affinity adsorption or fluorescence-activated cell sorting.

For effecting homologous recombination, U.S. Pat. Nos. 5,464,764 and 5,631,153 describe a double-selection strategy, in which two sequences homologous to the gene target flank a positive selection marker, and a negative selection marker is attached to the 3' terminal of the second flanking region. Homologous integration retains the positive selection marker, but eliminates the negative selection marker, whereas random integration usually retains both markers. Thus, by screening for both markers sequentially or together, cells that have been correctly targeted will be positively selected, and those that have been incorrectly targeted are selected out. U.S. Pat. No. 5,789,215 reports the use of homologous recombination targeting vectors for modifying the cell genome of mouse embryonic stem cells. Other information of interest for homologous recombination targeting can be found in U.S. Pat. Nos. 5,589,369 and 5,776,774.

Example 4 describes illustrative targeting vectors that are capable of inactivating the sheep gene for α(1,3)galactosyltransferase (α1,3GT) (SEQ. ID NOs: 2 & 3) via homologous recombination. The vectors comprise flanking regions identical to the targeted α1,3GT sequence, one side being about 1 kb, the other being at least 1 or 2 kb, in either order. In between the flanking regions is a selectable marker such as neo, designed to replace one of the Exons in the α1,3GT coding sequence. The selectable marker genes are not provided with their own promoter, and require continued translation through the upstream α1,3GT sequence in order to be expressed. This helps the marker select for properly integrated vector, because vector inserted at a random site will probably not link the marker gene to a suitable promoter, and resistance to the selector drug will not be conferred.

As an alternative to homologous recombination, a target gene can be inactivated using triplex-forming oligonucleotides that induce intrachromosomal gene conversion (Luo et al., Proc. Natl. Acad. Sci. USA 97:9003, 2000; Barre et al., Proc. Natl. Acad. Sci. USA 97:3084, 2000). Other techniques and reagents can be found in Inonue et al., J. Virol. 73:7376, 1999; Cole-Strauss et al., Science 273:1386, 1996;

Hasty et al., Mol. Cell Biol. 11: 4509, 1991; and International Patent Publication WO 98/48005.

Examples 5 to 7 provide illustrations of the use of targeting vectors for inactivating endogenous genes for α1,3GT and prion protein (PrP). A suitable cell line is combined with the vectors in a culture medium, and the vectors are introduced into the cell. In the illustration, the vectors are introduced by optimized conditions of electroporation. The cells are cultured for a time in an appropriate medium for maintenance of the cells, during which time the recombination event should occur. The cells are then subjected to culture conditions that permit outgrowth of cells bearing the selectable marker from successful recombination.

After genetic manipulation has been completed and altered cells have been selected, inactivation of the gene can be confirmed by testing at the mRNA level or at the protein level. The nature of the genetic alteration can be determined by PCR amplification using primers bracketing the targeted recombination site, and characterizing the amplification product, or by Southern analysis. If the targeting vector contains a unique sequence, then correct integration can be confirmed using a primer specific for the inserted sequence. Production of amplification product of the predicted size in a PCR reaction confirms correct integration.

The extended replicative capacity of the nuclear donor cells of this invention facilitates production of cells with a single genetic alteration, inducible by any suitable method, such as those already described. It is now also possible to undertake multiple genetic modifications on the same cell (or its progeny), before nuclear transfer.

For example, the techniques of this invention make it possible to generate a nuclear donor cell in which both alleles of a diploid gene are inactivated, or otherwise modified.

One method for generating cells modified on both alleles is to use a single targeting vector in combination with a selection process that requires double integration. This can be accomplished, for example, by assaying for the silencing of a naturally expressed autosomal dominant gene product. For example, if the gene causes expression of a cell-surface determinant, then the cells can be targeted, and then selected for phenotypic expression of the determinant. A cell not expressing the determinant should be inactivated on both alleles. The double recombination event will be statistically rare, but the extended proliferative capacity of the cell population puts batch screening for such an event within the scope of routine experimentation.

Another method for generating cells modified on both alleles is to use two different targeting constructs. The constructs can be each created with different selection markers that facilitate screening for double integration. For example, the cell can be targeted with a first targeting vector containing a first drug resistance gene, and selected using the corresponding drug. After a round of proliferation, the progeny can then be targeted with a second vector containing a second drug resistance gene, and selected using the second drug. In a variation of this technique, both targeting constructs are used at once, and selection of doubly modified cells is performed in a medium containing both drugs. The use of two different targeting constructs for the same gene on the two different alleles generates a cell in which the diploid gene contains a different artificial genetic modification in each allele.

Many types of genetic modifications are possible using these techniques. Cells and cloned animals with a gene knockout can be generated by inactivating the gene on both alleles. Gene modifications are possible in which both alleles are modified to change the encoding region, for example, to correct a congenital defect, or provide an improved trait patterned on another strain or species.

It is also possible to inactivate a gene and substitute another encoding region. For example, the first allele is inactivated using a targeting vector that inserts a drug resistance gene in place of the transcription start signal of the endogenous gene. Heterozygous knockouts are selected using the corresponding drug. The second allele is then targeted using a vector that inserts the substitute encoding region before or in place of the transcription start signal of the endogenous gene, but under control of the endogenous promoter. In this way, expression of the first encoding region will be phenotypically suppressed, and the substitute encoding region will be expressed in its place with a similar tissue specificity.

The increased proliferative capacity of the cells makes possible not just the multiple targeting of a single locus—but any type of genetic manipulation comprising multiple events. Superimposed on the modification of one or both alleles of one or more gene locus, the practitioner has the option of inserting one or more transgenes into the genome for expression of new gene products. With reflection upon these illustrations in the context of this disclosure, other embodiments of the invention will come readily to the mind of the skilled reader.

The timing of the telomerization step bears consideration in the context of these genetic manipulations. It is typically most convenient to increase telomerase activity in the cell before any further genetic manipulation takes place. This helps ensure that telomeres will be maintained at the same length as the parental cell throughout the genetic modification process. However, it is also possible to increase telomerase activity as an intermediate step in the process (say, after a first round of drug selection), or even after several genetic manipulations have been performed, in order to restore telomeres to an appropriate length. Also contemplated are strategies in which the TERT encoding region is included in a targeting vector used to inactivate an endogenous gene. In this way, telomerization of the cell occurs simultaneously with inactivation of one of the alleles. The vector can contain its own promoter controlling TERT expression, or the vector can insert the encoding region into the genome operatively linked to the endogenous promoter, providing the promoter is active in the cell type being used to generate the nuclear donor cell.

Once the desired genetic modifications have been made to the nuclear donor, the cell can be prepared for nuclear transfer. If TERT expression was increased by integrating a TERT encoding region into the genome, and if the cassette has been flanked with recognition sequences for site-specific recombination, as described in the previous section, then the cassette can be removed from the genome by introducing the corresponding recombinase into the cell.

Transient expression of the recombinase can be effected by transducing the nuclear donor cell with a suitable vector, such as an adenovirus or liposome-associated polynucleotide in which an encoding region for the recombinase is put under control of a heterologous promoter (such as those already listed) that is suitable for expression in the target cell. Also contemplated is a procedure whereby treatment with the recombinase is done after nuclear transfer, with the embryo (or its derivative cells) in culture.

Nuclear Transfer and Cloning

Once all the desired genetic manipulations have been performed, the donor cell can then be used for cloning. The nucleus is transferred into an enucleated recipient cell, such as an oocyte or other cell that is capable of developing into a fertile embryo after transfer and activation.

International Patent Application WO 97/07669 (Roslin Institute) describes quiescent cell populations for nuclear transfer. International Patent Application WO 97/07668 (Roslin Institute) describes inactivated oocytes as cytoplast recipients for nuclear transfer. For purposes of prosecution in the U.S., these patents and patent applications are hereby incorporated herein by reference in their entirety.

Nuclear transfer methods are particularly effective if the nucleus of the donor cell is quiescent, which can be achieved by culturing the donor cell in a serum-free medium (WO 97/07669). In an exemplary method, the nucleus of a donor cell is transferred into an oocyte that is arrested in the metaphase of the second meiotic division, and subsequently activating the reconstituted cell. Briefly, unfertilized metaphase II oocytes are collected as follows: Female animals are synchronized using progestagen sponges for ~14 days, and induced to superovulate with single injections of follicle-stimulating hormone on two successive days. Ovulation is induced with a suitable dose of gonadotrophin-releasing hormone or an analog thereof (e.g., ~8 mg GnRH Receptal™, Hoechst, UK) on the following day. The oocytes are recovered by flushing from the oviduct one day later, washed, and enucleated by treating with cytochalasin B and aspirating the nucleus using a glass pipette. Enucleated oocytes are then placed into contact with a single cell that acts as the nucleus donor.

Fusion of the donor nucleus into the enucleated recipient cell is effected by placing the couplet in a fusion chamber and aligning it between the electrodes. Electrical pulses are then applied to induce fusion, typically a low-voltage AC pulse for several seconds, followed by a plurality of very short high-voltage DC pulses. Following an incubation period, activation is induced by application of an additional electrical pulse. The reconstructed zygote is then cultured for a time before engrafting into a surrogate female. Further details and alternative procedures are described in the patent publications cited above.

Estrus in the surrogate female is typically synchronized artificially using a suitable combination of inducing agents. Cameron et al. (Aust. Vet. J. 66:314, 1989) discuss synchronization methods and other practical aspects for commercial embryo transfer in pigs. Blum-Reckow et al. (J. Anim. Sci. 69:3335, 1991) report experiments relating to transfer of pig embryos after long-term in vitro culture. Replacing medium every 12 h during culture improved survival, and pregnancy rate improved if the sexual cycle of recipients was 24 h behind that of the donor.

The embryos are introduced into the uterus of the recipient female using any suitable technique, including devices adapted for the purpose, or appropriate surgical methods. For example, U.S. Pat. No. 4,326,505 describes surgical procedures for embryo transplants in animals, in which the uterine horn is positioned in the peritoneal cavity proximate to the vaginal wall, a cannula is inserted through the vaginal wall and into the uterine horn, and the embryo is introduced through the cannula. Non-surgical methods include using a suitable device to manipulate the injection port through the folds of the cervix to the bifurcation of the uterus. For example, devices and techniques for porcine non-surgical embryo transfer are reported by Li et al. (J. Anim. Sci. 74:2263, 1996). Wallenhorst et al. (J. Anim. Sci. 77:2327, 1999) describe the effect of transferring pig embryos to different uterine sites.

Use of Cloned Embryos

An embryo prepared according to this invention can be used for any desirable purpose, including but not limited to therapeutic cloning, cloning for agricultural purposes, production of embryo-derived cell lines and derivatives, and production of genetic knockouts and genetically modified animals to investigate gene function.

One potential use is the generation of animal tissue suitable for xenotransplantation. The main xenogeneic antigen causing rejection of animal tissues in humans is the cell-surface oligosaccharide determinant Galα(1,3)Gal. The epitope is made by α(1,3)galactosyltransferase, present in the cells of most mammals, but not humans (Joziasse et al., Biochim. Biophys. Acta 1455:403, 1999).

This invention provides a method for making animal tissue free of the Galα(1,3)Gal antigen by knocking out the α1,3GT gene on both alleles. The sheep α(1,3)galactosyltransferase cDNA sequences are provided in SEQ. ID NOs: 2 & 3 of this disclosure, and the corresponding biological deposit. The pig α(1,3)galactosyltransferase cDNA sequence can be found in Strahan et al., Immunogenetics 41, 101 (1995) and GenBank Accession L36152; U.S. Pat. Nos. 5,821,117; 5,849,991; and International Patent Application WO 95/28412. The genomic organization of porcine α1,3GT was reported by Katayama et al. (Glycoconjugate J. 15:83, 1998). Example 1 below provides exemplary vectors with different drug resistance genes that can be used for sequential inactivation of the two α1,3GT alleles. Examples 5 to 7 illustrate how such vectors are used in telomerized animal cells suitable for nuclear transfer.

Also contemplated is modification of the animal tissue with other glycosyltransferase enzymes. In place of the Galα(1,3)Gal epitope on human cells, the N-acetyl lactosamine acceptor oligosaccharide is processed by an α(1, 2)fucosyltransferase (α1,2FT). This enzyme makes the determinant Fucα(1,2)Galβ(1,4)GlcNAc (otherwise known as H precursor substance), present on most human cells, and the acceptor substrate for ABO blood group substance. Switching the α1,3GT gene in animal tissue to α1,2FT is believed to have advantages in preparing xenotransplant tissue. The tissue may further contain transgenes of the ABO blood group transferases.

Another potential use of this invention is to improve the safety of agricultural products. Creutzfeldt-Jakob disease is a fatal human neurodegenerative disease caused by prions. A variant form (vCJD) is thought to relate to the consumption of beef from animals affected with bovine spongiform encephalopathy ("Mad Cow Disease"). Scrapie is the corresponding spongiform disease in sheep and goats. The pathological characteristics of prion diseases include neuronal vacuolation, astrocytic gliosis, and amyloid plaques with filaments composed of prion protein. The gene for prion protein (PrP) is present in all species, and heavily implicated in disease pathology (Bolton et al., Science 218, pp. 1309–11 (1982); (Basler et al., Cell 46, pp. 417–28 (1986). However, the physiological role of PrP is uncertain, and it appears that mice can get along perfectly well without it (U.S. Pat. No. 5,698,763).

This invention provides a technique whereby PrP expression is prevented in agricultural livestock, particularly sheep and cows. The sheep PrP gene sequence is provided in Goldmann et al., Proc. Natl. Acad. Sci. USA 87:2476, 1990 (SEQ. ID NOs: 4 & 5). The bovine PrP sequence is provided in Goldmann et al., J. Gen. Virol. I72:201, 1991. Targeting vectors that disrupt the PrP encoding region (Example 4) can be used in telomerized cells to produce nuclear donors that are homozygously inactivated at the PrP locus.

A further potential use of an embryo prepared according to this invention is the generation of stem cell lines. Human stem cells can be established from blastocysts and passaged in culture by known techniques (U.S. Pat. No. 6,200,806 and WO 99/20741). The stem cells can then be differentiated into specialized cells (such as cells of the hepatocyte or neural lineage) or their precursors, and used for such purposes as preparing therapeutic compositions for regenerative medicine, and testing the metabolic effects of potential medicaments. If telomerase activity is increased in the nuclear donor by integrating a TERT gene flanked by recombination sites, the gene can be removed before nuclear transfer, or after establishing a cell line from the embryo.

The examples that follow are provided by way of further illustration, and are not meant to imply any limitation in the practice of the claimed invention.

EXAMPLES

Example 1

Expression of hTERT in Sheep Nuclear Donor Cells

A vector containing an expression cassette for telomerase reverse transcriptase was found to increase functional telomerase activity and replicative capacity in sheep fibroblasts suitable for nuclear transfer.

Figure 1:
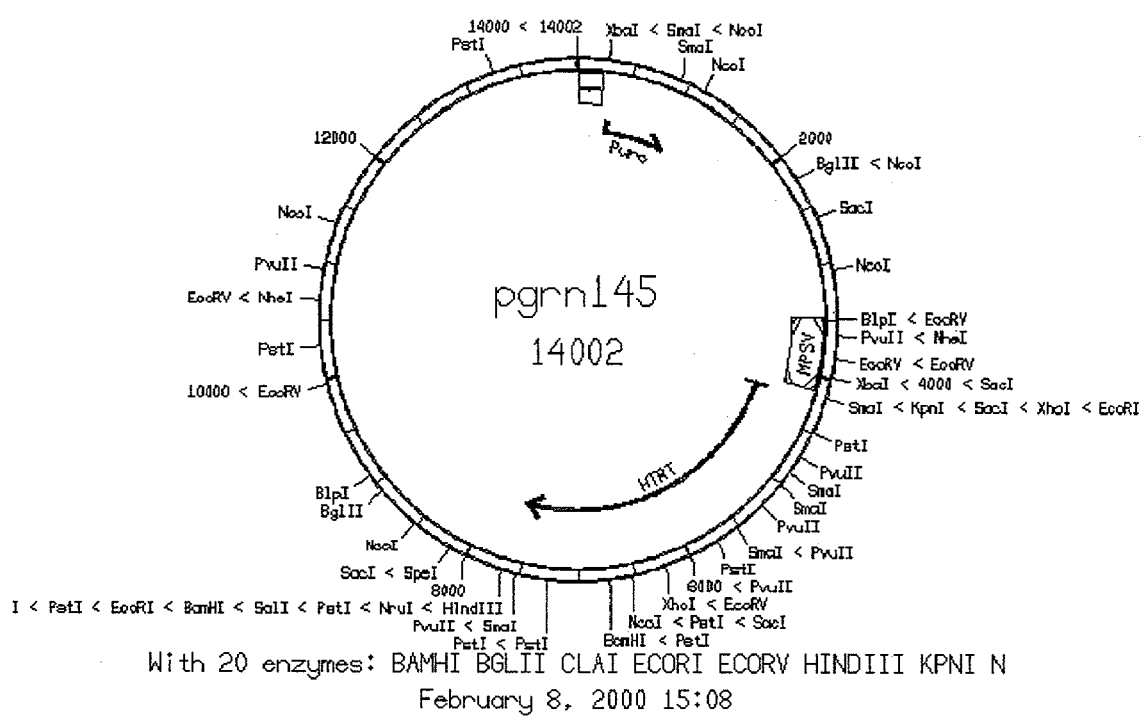

FIG. 1 is a map of plasmid pGRN145. It contains sequences encoding telomerase reverse transcriptase (abbreviated here as hTRT) with a consensus Kozak sequence downstream of the myeloproliferative sarcoma virus (MPSV) promoter. It also contains puromycin and hygromycin resistant gene sequences and allows drug selection of the transfected clones. SEQ. ID NO: 1 is the nucleotide sequence of pGRN145.

Primary sheep fibroblast cell line designated BW6F2 (passage 6, obtained from a Black Welsh sheep) was transfected with linearized pGRN145. The cells were plated in 96 well plates, and selected using puromycin at 1 µg/mL. PCR screening with puromycin primers showed that all but one of the selected clones contained the vector sequence.

Fourteen of the clones were developed into cell lines. hTERT expression was measured in the cloned sheep fibroblasts by Western blot. Thirty µg cell lysate was separated by 7.5% SDS-PAGE, blotted onto nitrocellulose, and detected using antibody 1A4 (specific for hTERT) at 1:10,000, followed by goat anti-mouse IgG labeled with horse-radish peroxidase at 1:5000.

hTERT expression was also measured by immunocytology. Cells were grown in chamber slides and fixed with 4% paraformaldehyde. The cells were stained with 1A4 anti-hTERT antibody at 1:1000 dilution for 1 h, then with biotinylated secondary antibody at 1:500, and finally with streptavidin Texas Red™ at 1:200. Nuclei were counterstained with DAPI. hTERT protein was detected by immunocytochemistry in some cell lines but not others, correlating with hTERT production in the lines detected by Western blot.

Functional telomerase activity was measured by TRAP assay, and was found to be positive in 10 of these clones, compared with the original BW6F2 line.

Vector Containing an Excisable TERT Cassette

The pGRN145 vector has been adapted to flank the hTERT encoding region with two lox sites for site-specific recombination and removal of the gene before nuclear transfer.

Figure 2:
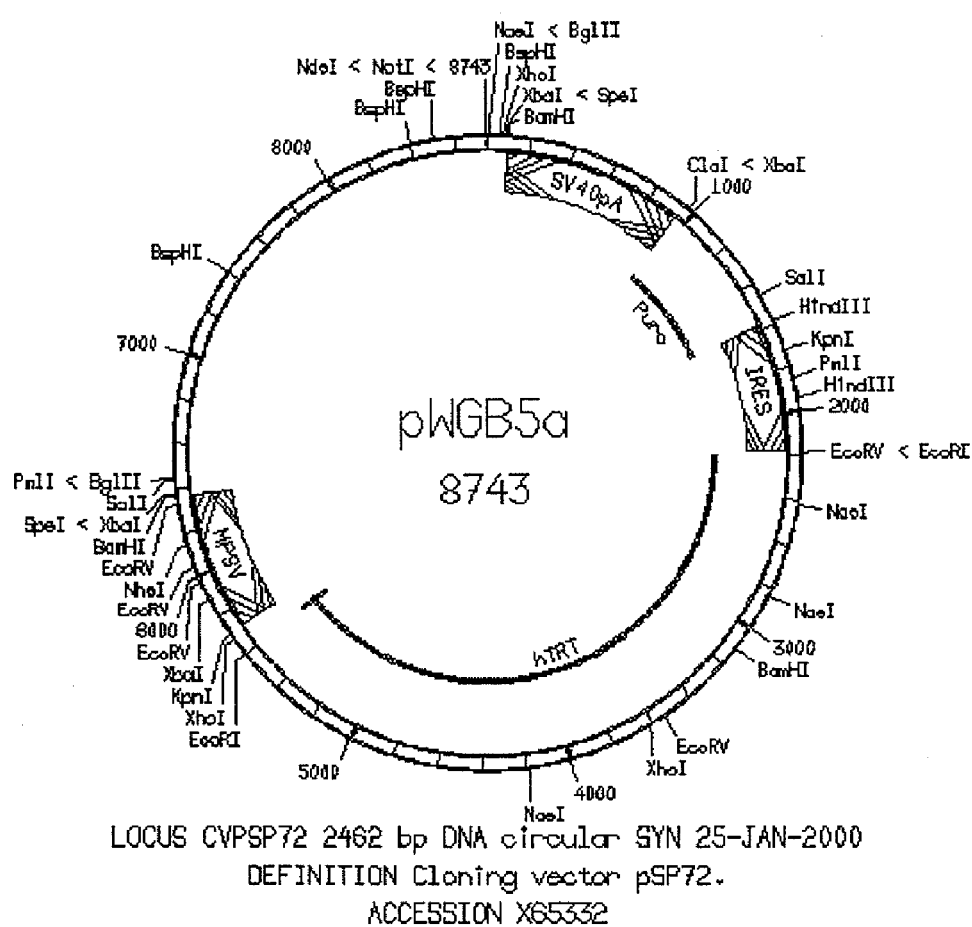

FIG. 2 shows the design of the adapted targeting vector. It is an IRES bicistronic expression vector, comprising the MPSV promoter, followed by hTERT cDNA, IRES sequences, and the puromycin selection gene. This entire region is flanked by loxP sequences.

The hTERT vector was constructed as follows. A 0.85 kb fragment containing the SV40 small-t intron and polyadenylation signal was blunt-ligated into SalI site of pBluescript™ IIKS. A BIpI-NotI fragment of plasmid GRN145, containing MPSV promoter and hTERT cDNA was blunt-ligated into PstI site. An EcoRI-XbaI fragment from a plasmid containing IRES sequences and puromycin resistant gene, was blunt-ligated into HindIII site.

Finally, the NotI fragment (comprising the MPSV promoter, hTERT cDNA, IRES sequences, puromycin resistant gene and SV40 polyadenylation signal) was blunt-ligated into EcoRI-XhoI sites of a plasmid containing two loxP sites. The conjunctions have been sequenced to confirm the fidelity. This vector has been designated pWGB5 (SEQ. ID NO: 6). An empty vector control was constructed by deleting the hTERT cDNA sequence from pWGB5 by EcoRI digestion and religation.

Example 2

Human TERT Extends Replicative Capacity in Non-Human Nuclear Donor Cells

In order to determine the replicative capacity of the cloned fibroblast cell lines derived in Example 1, the cells were passaged continuously using standard culture conditions. The cells were cultured in GMEM containing 10% fetal calf serum at 37° C., 5% $CO_2$ in continuous log phase.

FIG. 3 shows the growth curves for these cells. Each line represents a single clone designation, except BW6F2, which is the parental (untransfected) line. The solid circles represent telomerase-expressing clones, and the solid triangles represent telomerase-negative clones. Open squares represent clones that were telomerase-negative initially, but became positive later. All telomerase-negative clones became senescent towards the end of the growth curve, as did the parental BW6F2 cells.

The clones expressing hTERT have been grown through at least 260 population doublings (PDs) and still grow like young cells. Cells transfected with a control plasmid without hTERT cDNA or the transfected cells not expressing hTERT grew less than 83 PDs. The parental cells only replicate through 127 PDs, when they become senescent.

Figure 4:
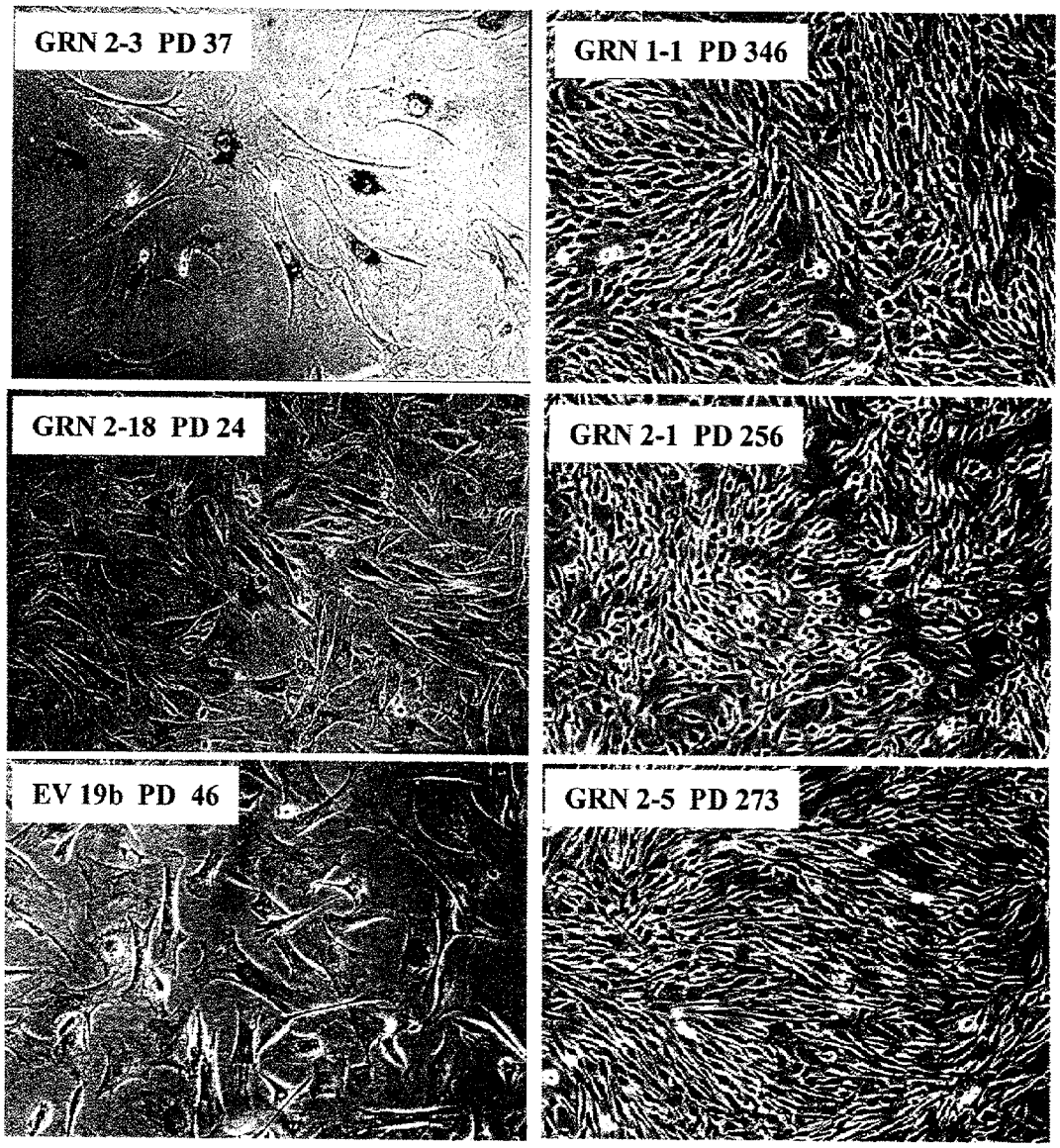

FIG. 4 shows staining of the cells with X-gal, which stains senescing cells blue. The cells were fixed in 2% formaldehyde/0.2%glutaraldehyde for 3–4 min, then stained with X-gal solution at pH 6. Telomerase negative clones are in the left panels; telomerase positive clones are in the right panels. Cells expressing hTERT showed no positively staining cells after they had been carried to ~256 PDs. In contrast, the cells transfected with the control vector showed over 10% positively staining cells when they had grown to less than ~50 PDs.

No Evidence for Malignant Transformation

The hTERT expressing sheep fibroblasts were analyzed to determine whether or not the hTERT expressing cells showed signs of transformation to a malignant phenotype.

The cells were assessed for karyotype stability. Eight of the 10 telomerase-expressing clones showed normal karyotype when measured (passages 13 to 97).

The cells were also assessed for response to serum starvation. The cells were cultured in medium containing only 0.1% serum for 7 days, and assessed by FACS analysis (fixed in 70% ethanol and stained with propidium iodide). None of the telomerase-expressing clones was proliferating under these conditions. The cells were then recultured 24 h in 10% serum containing medium, and synchronized normally. When cultured for 3 days after reaching confluence, the cells also showed evidence of contact inhibition.

Telomere length was assessed by extracting DNA from cloned cells using a blotting assay. The DNA was digested with RsaI and HinfI, separated on 0.7% agarose, blotted onto a nylon membrane, and probed with $^{32}$P-labeled (TTAGGG)$_3$ oligonucleotide.

It was found that clones with higher hTERT expression levels (detected by Western blot and immunocytochemistry using 1A4 antibody) maintained their telomere length, while clones with lower hTERT expression levels were typically the ones showing shortened telomeres.

A summary of results from these experiments is shown in Table 1.

plates. After 6 days, 10 colonies were confluent and transferred to a 25 cm$^2$ flask. Within 10 days, eight of these colonies were expanded up to a 75 cm$^2$ flask, frozen into six vials, and stored in liquid nitrogen.

When analyzed by immunocytochemistry using hTERT antibody 1A4, most clones showed cytoplasmic staining. One clone designated PF6C-T3C showed significant nuclear staining, similar to the cloned sheep cell line GRN2.2 (Example 1).

TABLE 1

Characteristics of Telomerized Sheep Fibroblast Clones

| Designation | PCR for puromycin gene | TRAP assay (telomerase activity) | Population doublings observed | Response to serum starvation | Contact inhibition | Karyotype |
|---|---|---|---|---|---|---|
| GRN 1-1 | + | − | 354 | Normal (p54–56) | Normal (p72) | Normal (p14, p49) |
| GRN 1-2 | + | −→+ | 289 | Normal (p50) | Normal (p47) | Normal (p8, p35) |
| GRN 2-1 | + | + | 264 | Normal (p50) | Normal (p43) | Normal (p13, p80) |
| GRN 2-2 | + | −→+ | 294 | Normal (p48) | Normal (p52) | Normal (p30) Abnormal (p90) |
| GRN2-3 | + | − | 37$^a$ | n.d. | n.d. | n.d. |
| GRN2-4 | + | − | 75$^a$ | n.d. | n.d. | n.d. |
| GRN 2-5 | + | + | 279 | Normal (p54) | Normal (p46) | Normal (p12, p86) |
| GRN 2-7 | + | + | 314 | Normal (p62) | Normal (p64) | Normal (p15, p97) |
| GRN 2-8 | + | + | 318 | Normal (p60) | Normal (p52–53) | Normal (p15) |
| GRN 2-10 | + | + | 166$^b$ | n.d. | n.d. | Abnormal (p13) |
| GRN 2-12 | + | + | 293 | Normal (p50) | Normal (p51–53) | n.d. |
| GRN 2-13 | + | + | 258 | Normal (p47) | Normal (p48–49) | Normal (p16) |
| GRN 2-18 | − | − | 83$^a$ | Abnormal (p18) | n.d. | n.d. |
| GRN 2-20 | + | −→? | 113$^b$ | n.d. | n.d. | n.d. |

$^a$Cells became senescent
$^b$Growth curve stopped

Expression of hTERT in Pig Nuclear Donors

A primary fibroblast cell line was isolated from fetal pig carcass, and seeded into 25 cm$^2$ flasks at 2.5×10$^5$ cells in 10 mL Dulbecco's MEM containing 20% serum.

Lipofection with hTERT was performed as follows: 4.4× 10$^6$ PF6C p3 cells were transfected with lipofectamine™ plus 30 µg pGRN145 at a ratio of 3:1 with 4 h incubation. Twenty-four hours after transfection, the cells were divided into 6×10 cm plates (7×10$^5$ cells per plate). After 3 days, the cells were 95% confluent, and selection medium was added.

Electroporation was performed as follows: 4.6×10$^6$ PF6C p3 cells were washed and electroporated in prepared electroporation buffer (9 hypo-osmolar: 1 iso-osmolar). The Eppendorf™ electroporator settings were 300 v, 100 µs. Immediately after electroporation the cells were divided into 6×10 cm plates (7×10$^5$ cells per plate). After 3 days, selection medium was added to each plate.

Sixteen days after transfection, established colonies of isolated cells were visible in the six lipofection plates. In comparison, in the electroporation plates only single cells were visible with no colony formation. Thirty seven colonies were picked by ring cloning and transferred to 12 well Example 3

Human TERT Improves Genetic Stability in Non-Human Nuclear Donor Cells

It has been suggested that the telomeres play an important role in genome stability (Hackett et al., Cell 106:275, 2001; Riha et al., Science 291:1797, 2001). To assess the effects of hTERT expression on the genome stability of the stably transfected sheep fibroblast, the cell lines transfected with the hTERT gene were analyzed for hTERT expression and activity, and cytogenetic analysis.

Telomere length was determined by telomere restriction fragment (TRF) Southern blot analysis as described previously (Harley et al., Nature 345:458, 1990). Briefly, 1–3 µg of DNA was digested with restriction enzymes Hinf/RsaI and fractionated by 0.7% agarose gel electrophoresis, then transferred onto a positively charged nylon membrane. The membrane was hybridized with (TTAGGG)$_3$ probe labeled with either γ-[$^{32}$P]ATP or digoxigenin. Signals were visualized by phosphorImager scan either directly ($^{32}$P labeled probe) or after antibody/substrate reactions (digoxigenin labeled probe). Mean TRF was calculated as described by Ouellette et al., J. Biol. Chem. 275:10072, 2000.

Expression of hTERT and endogenous sheep GAPDH was measured as follows. Cells were trypsinized and counted, then washed with PBS. Total RNA was extracted with RNAzol B and digested with DNase I. First strand cDNA was synthesized from 5 μg of total RNA by reverse transcriptase in 20 μL volume with oligo $Pd(T)_{15}$. Each PCR was carried out with 5 μl of the reverse transcription product and amplified for 26 cycles of 94° C. for 30 sec, 60° C. for 30 sec and 72° C. for 45 sec using specific primers for human TERT or sheep GAPDH. Real time qRT-PCR primers and TaqMan probes were selected for hTERT and sheep GAPDH using Primer Express software (Applied Biosystems). Each TaqMan™ reaction was performed in quadruplicate. The hTERT mRNA copy number was calculated with a standard curve generated from hTERT cDNA plasmid at concentrations equivalent to 0.01 to 1000 copies per cell. Telomerase activity of cell extracts was analyzed by telomeric repeat amplification protocol (TRAP) assay as described previously (Kim et al., Nucleic Acids Res. 25:2595, 1997). Results are shown in Table 2:

TABLE 2

Telomere length, Telomerase Activity, and hTERT Expression

| Cell clone | Mean TRF[a] (kb) | TRAP Assay[b] PD = 0 | TRAP Assay[b] PD > 200 | Relative hTERT mRNA Expression[c] | hTERT mRNA per Cell |
|---|---|---|---|---|---|
| 1-1 | 8.4 | 30% | 48% | 2.6 | 0.34 |
| 2-1 | 20.7 | 51% | 46% | 5870 | 375 |
| 2-5 | 21.0 | 39% | 52% | 1280 | 87 |
| 2-7 | 21.2 | 30% | 52% | 5250 | 345 |
| 2-8 | 10.8 | 52% | 39% | 8.1 | 0.58 |
| 2-12 | 14.6 | 60% | 55% | 9.3 | 0.65 |
| 2-13 | 6.0 | 38% | 30% | 1.0 | 0.08 |
| BW6F2 (young) | 20.9 | 0 | — | 0 | 0.02 |
| BW6F2 (senescent) | 11.3 | — | 0 | not done | not done |

[a]Mean TRF when telomere length is stabilized
[b]TRAP activity compared with human 293 cell line
[c]Measured by qRT-PCR, normalized with internal GAPDH level, and calculated relative to clone 2-13

The cell lines exhibiting high steady-state hTERT mRNA levels and detectable hTERT protein (2-1, 2-5 and 2-7) did not undergo telomere shortening and they fully maintained their telomere lengths. Line 2-8 and 2-12, which had low levels of hTERT mRNA and undetectable levels of hTERT protein, exhibited telomere shortening but their telomeres were stabilized with a mean TRF greater than 10 kb. Lines 1-1 and 2-13, with very low level of hTERT mRNA also exhibited telomere shortening but their telomeres shorten to an even greater extent and were only stabilized when the mean TRF was below 1 kb.

For karyotype analysis, slides with metaphase spreads were stained in 5% Gurrs R66 Giemsa and then mounted. Results are shown in Table 3:

TABLE 3

Karyotype of hTERT-expressing sheep fibroblasts

| Cell line | Population Doublings | Days in Culture | 50 | Number of Cells 50 (100%) | 0 | Abnormalities |
|---|---|---|---|---|---|---|
| 1-1 | 333 | 36 | 50 | 50 (100%) | 0 | |
|  | 222 | 197 | 10 | 8 (80%) | 2 )20%) | SM |
|  | 318 | 279 | 30 | 11 (37%) | 19 (63%) | Smet, DIC, Mar |
|  | 363 | 322 | 30 | 2 (7%) | 28 (93%) | SubM, SM, LM |
| 2-1 | 29 | 47 | 30 | 30 (100%) | 0 | |
|  | 231 | 285 | 30 | 30 (100%) | 0 | |
|  | 264 | 320 | 30 | 30 (100%) | 0 | |
| 2-5 | 26 | 47 | 30 | 30 (100%) | 0 | |
|  | 68 | 95 | 30 | 30 (100%) | 0 | |

TABLE 3-continued

Karyotype of hTERT-expressing sheep fibroblasts

| Cell line | Population Doublings | Days in Culture | Number of Cells 50 | 50 (100%) | 0 | Abnormalities |
|---|---|---|---|---|---|---|
|  | 248 | 285 | 30 | 30 (100%) | 0 |  |
|  | 279 | 320 | 10 | 29 (97%) | 1 (3%) | LM |
| 2-7 | 36 | 48 | 30 | 30 (100%) | 0 |  |
|  | 281 | 281 | 30 | 30 (100%) | 0 |  |
|  | 313 | 316 | 30 | 29 (97%) | 1 (3%) | SubM |
| 2-8 | 36 | 48 | 30 | 30 (100%) | 0 |  |
|  | 228 | 231 | 10 | 10 (100%) | 0 |  |
|  | 286 | 284 | 30 | 24 (80%) | 6 (20%) |  |
|  | 317 | 316 | 30 | 15 (50%) | 15 (50%) | SM, SubM |
| 2-12 | 18 | 32 | 10 | 10 (100%) | 0 |  |
|  | 201 | 230 | 10 | 10 (100%) | 0 |  |
|  | 256 | 279 | 30 | 29 (97%) | 1 (3%) | Mar |
|  | 429 | 433 | 30 | 16 (53%) | 14 (47%) | LM |
| 2-13 | 21 | 49 | 30 | 30 (100%) | 0 |  |
|  | 225 | 280 | 30 | 5 (17%) | 25 (83%) | Mar, Ring, DIC, LM, |
|  | 266 | 322 | 30 | 0 | 30 (100%) | SM, LM, SM, SubM, Ring |

DIC, dicentric;
LM, large metacentic;
Mar, marker chromosome;
Ring, ring chromosome;
SM, small metacentric;
SubM, submetacentric At the beginning of their proliferative lifespan, all hTERT transfected clones showed normal karyotype. However, after about 220 population doublings, clones 1-1 and 2-13, started to exhibit a high frequency of abnormal karyotype (20% or more cells). These abnormalities included abnormal submetrocentric, dicentric and ring chromosomes, which likely resulted from chromosomal end-end fusions. The frequency of these abnormalities increased with cell ageing. Lines 2-8 and 2-12 also started to exhibit chromosomal abnormalities after extended culture, although this occurred at later PDs than was the case for lines 1-1 or 2-13. By contrast, cells 2-1, 2-5 and 2-7 essentially maintained a normal karyotype even at high population doublings, although very occasionally an abnormal karyotype was observed. The genomic instability of these cell lines was inversely correlated with the level of hTERT mRNA expression: high hTERT expressing lines, 2-1, 2-5, 2-7, showed no abnormal karyotype; low hTERT expressing lines 2-12 and 2-8, showed a low frequency of abnormality (3% and 20% respectively); and very low hTERT expressing lines 1-1 and 2-13 showed high frequencies of karyotypic abnormalities (63% and 83%, respectively).

These data lead to the conclusion that high levels of TERT expression are required to maintain the genomic stability of these lines. When lower levels of TERT are present, the telomeres shorten and are then maintained at a standard length determined directly by the level of TERT expression. Genomic instability in terms of the timing and degree of karyotypic abnormalities is inversely related to the level of TERT mRNA expression. Thus, TERT may provide genomic stability by performing functions beyond telomere elongation.

Example 4

Construction of Targeting Vectors

Vectors have been constructed to disrupt the α(1,3)galactosyltransferase (α1,3GT) gene and the prion protein (PrP) gene by homologous recombination.

Vector for Targeting Galactosyltransferase

The sequence of the sheep cDNA for α1,3GT is shown in SEQ. ID NOs: 2 & 3. To develop genomic constructs, DNA was isolated from Black Welsh Mountain fetal fibroblasts, and a λDASHII phage library was constructed. Sau3A partially digested genomic DNA was dephosphorylated and ligated to compatible BamHI vector arms (Stratagene). The ligation products were packaged to produce recombinant phage, which were propagated on spi selective XL1-Blue-MRA(P2) bacterial cells. The resulting library had a complexity of $1.4 \times 10^6$ recombinants, and was subsequently amplified once. Six phage clones were isolated that spanned Exon-4, Exon-6-7 and Exon-9.

Recombinant phage designated B, C and G, have been deposited as a pooled sample with the National Collections of Industrial and Marine Bacteria Limited (NCIMB), Aberdeen, U.K, under Accession No. NCIMB 41056. The phage can be separated using the oligonucleotide probes 5'-GG-GAGGAAGC GAAGGTGCA-3' (SEQ. ID NO: 7), 5'-CT-TGATGGGT TTATCCAGAA CA-3' (SEQ. ID NO: 8) and 5'-TGATAATCCC AGCAGTATTC-3' (SEQ. ID NO: 9), respectively. Each recombinant phage has also been deposited separately with the NCIMB under the following Accession numbers: Clone B, No. 41059; Clone C, No. 41060; and Clone G, No. 41061.

A targeting vector was designed directed towards Exon 4 of the sheep α1,3GT gene. The vector comprises two regions that are complementary to genomic sequence; a 1.2-kb 5' arm, which includes sequence from Intron 3 leading up to and including the start codon in Exon 4, and a ~9-kb 3' arm that initiates 1.5-kb into Intron 4, continuing to Intron 5. Separating these regions is neo$^R$-polyA sequence. After homologous recombination, the vector confers neomycin phosphotransferase resistance to the cells and deletes 1.5-kb of genomic sequence, including the first coding exon of α1,3GT gene. The entire cassette was cloned into pBlue-Script™ for propagation in DH5α bacterial cells.

This vector was designated p0054. It was constructed by amplifying a truncated left arm (300 bp, includes EcoRI site) (using primers 199001, 5'-ACGTGGCTCC AAGAAT-TCTC CAGGCAAGAG TACTGG-3', SEQ. ID NO: 10; and 199006, 5'-CATCTTGTTC AATGGCCGAT CCCAT-TATTT TCTCCTGGGA AAAGAAAAG-3', with tail complementary to the start of neo coding sequence, SEQ. ID NO: 11), and a neo-polyA sequence obtained from Stratagene (using primers 199005, 5'-CTTTTCTTTT CCCAG-GAGAA AATAATGGGA TCGGCCATTG AACAAGATG-3', SEQ. ID NO: 12, with tail complementary to left arm; and 199004, 5'-CAGGTCGACG GATCCGAACA AAC-3', SEQ. ID NO: 13). These fragments were used to prime from each other to give a 1.2-kb fusion product. This was ligated to Intron 3 sequence, to extend the left arm, and to ~9-kb of 3' sequence to create the right arm, which initiates 1.5-kb into Intron 4, continuing to Intron 5.

Another promoterless vector is constructed, having the designation p0063. Instead of the neo drug resistance gene, it contains the pac gene that codes for puromycin N-acetyl-transferase, permitting a second round of screening using a different drug. The pac sequence is available in plasmid pPUR from ClonTech. The oligonucleotide primers used to generate the 5'-pac-polyA fusion were, for the 5' region, 199001 (SEQ. ID NO: 14) and 699002 (5'-GCGCACCGTG GGCTTGTACT CGGTCATTAT TTTCTCCTGG GAAAA-GAAAA G-3', SEQ. ID NO: 15), with tail complementary to the start of pac coding sequence; and, for pac-polyA, 699004 (5'-GAGAAAATAA TGACCGAGTA CAAGCCCACG GTGC-3' SEQ. ID NO: 16), with tail complementary to left arm, and 699005 (5'-CTGGGGATCC AGACATGATA AGATAC-3' SEQ. ID NO: 17).

Vectors for Targeting Prion Protein

The plasmid designated p0036 for homologous recombination to inactivate the sheep PrP gene responsible for scrapie was constructed as follows. Phage corresponding to GenBank Accession Number U67922 (Lee et al., Genome Res. 8:1022, 1998) was isolated using a PrP coding sequence probe (ATG start codon to TGA stop codon). PCR of the 5'arm using the sheep genomic library was performed using primers 6F (19786) and 7R (22278) to give a 2.4 kb fragment. This also engineered a SacI site to the 5'end of the vector, which allowed the final vector to be linearized before transfection. PCR of neo-pA (from pMC1-neo; Stratagene) sequence was performed using primers 10F and 8R to give a 0.9 kb fragment.

Primers 7R and 10F, which were used to produce these products, also contained sequence corresponding to the start of the neo gene and to the end of the 3' arm, respectively. By incubating the 2.4 kb and 0.9 kb fragments together in a second PCR reaction, they primed from each other to produce the fusion product of 3.3 kb. This product was cloned into SacI and SalI sites in pBluescript. To complete the vector, a ~3 kb KpnI fragment (23721 to 26748) was cloned into the KpnI site of the above precursor vector.

The primers used were as follows: Primer 6F: CCGAGCTCG CCAATTTCAT GGCTGCAGTCACC (SEQ. ID NO: 18). Primer 7R: CGATCCCAT GATGACT-TCT CTGCAAAATAAAG (SEQ. ID NO: 19). Primer 10F: GAGAAGTCA TCATGGGATC GGCCATTGAACA (SEQ. ID NO: 20).

Primer 8R: TGCAGGTCG ACGGATCCGAA (SEQ. ID NO: 21).

Example 5

Targeting the Galactosyl Transferase and PrP Genes

Electroporation conditions were optimized using a β-galactosidase marker plasmid, pCMV-Sport-βgal (Gibco). Using a 0.4 cm cuvette with $3 \times 10^5$ cells (0.8 mL, 6 μg plasmid DNA) and a setting of 250 μF: 400 Volts (Gene Pulser, BioRad), 10–30% of the surviving fibroblasts stained positive for β-gal expression.

For targeting the α1,3GT gene, 10, 25 or 100 μg of NotI linearized p0054 vector was mixed with $1 \times 10^7$ early passage Black Welsh Mountain fetal fibroblasts and pulsed. Cells were grown on tissue culture plastic for 24 h before G418 was added at 300 μg/mL. After 10–14 days, colonies were isolated.

For targeting the PrP gene, 10 to 100 μg of SacI linearized p0036 vector was mixed with $1 \times 10^7$ early passage Black Welsh Mountain fetal fibroblasts (BW6F2) and pulsed at 25μF: 400V. Cells were grown on tissue culture plastic for 24 h, and then G418 was added to the medium at 400μg/mL. After 10-14 days, colonies were isolated.

Site-specific recombination was detected by PCR amplification. Wild type and targeted α1,3GT alleles were detected using sense (399010, 5'-CAGCTGTGTG GGTATGGGAG GG-3'; SEQ. ID NO: 22) and antisense (499006, 5'-CTGAACTGAA TGTTTATCCA GGCCATC-3'; SEQ. ID NO: 23) PCR primers, yielding products of 2.8-kb and 2.2-kb, respectively. A second PCR screen with primers 399010 (SEQ. ID NO: 22) and 399005 (5'-AGC-CGATTGT CTGTTGTGCC CAGTCAT-3'; SEQ. ID NO: 24) produced a fragment of 1.5-kb only in clones that were correctly targeted.

PCR amplification for wild type and targeted PrP alleles was performed using sense (Target F1, 5'-TTCAGTCGCT CTGTTGTGTC CCA-3'; SEQ. ID NO: 25) and antisense (Target R1, 5'-AGCATCCCTC CTGCCTTCAG TTCTTC-3'; SEQ. ID NO: 26) PCR primers, yielding products of 4.6-kb and 3.9-kb, respectively. A second PCR screen with primers Target R1 (SEQ. ID NO: 26) and 399005 (SEQ. ID NO: 24) produced a fragment of 3-kb only in clones that were correctly targeted.

For Southern blot analysis of the α1,3GT gene, probe fragments were generated as follows. Oligos 800-005 and 800-006 were annealed by reducing the temperature by 1° C. every 5 min from 94° C. to 4° C. 800-005 forward=GAT CCC AGC TGT GTG GGT ATG GGA GGG AAA GGC CAC CTG GGA AAT GGT TGG GTC TCA ATT GTA AAA GAC CAG CAT GCT TTC TGC TCT GAA CGG CGG AGC ACG TAG TTA GG (SEQ. ID NO: 27); 800-006 reverse=GAT CCC TAA CTA CGT GCT CCG CCG TTC AGA GCA GAA AGC ATG CTG GTC TTT TAC AAT TGA GAC CCA ACC ATT TCC CAG GTG GCC TTT CCC TCC CAT ACC CAC ACA GCT GG (SEQ. ID NO: 28). These oligos correspond to genomic sequence immediately 5' to the left arm of the aGT targeting vector. They were ligated together by virtue of the engineered BamHI overhang sequences on each end thus forming a concatamer containing three repeated oligo sequences. For PrP, the region from 16701 to 17151 of accession u67922 was amplified by PCR and used as a probe fragment. This lies 5' of the left arm of the PrP targeting vector.

Southern analysis was conducted as follows. 10 μg genomic DNA was digested with BamHI, electrophoresed, and transferred to Ambion Bright Star™ membranes, using the Southern MaX™ system according to manufacturer's directions. Membranes were prehybridized in Ambion Ultrahyb™ solution at 42° C.; then probe was added and the incubation continued at the same temperature overnight. Membranes were washed in buffers of increasing stringency at 42° C. Patterns of hybridization were detected using a BioRad phosphorimager. Conditions for PrP S. blots were performed in the same way except genomic DNA was digested with BgII restriction enzyme.

Figure 5:
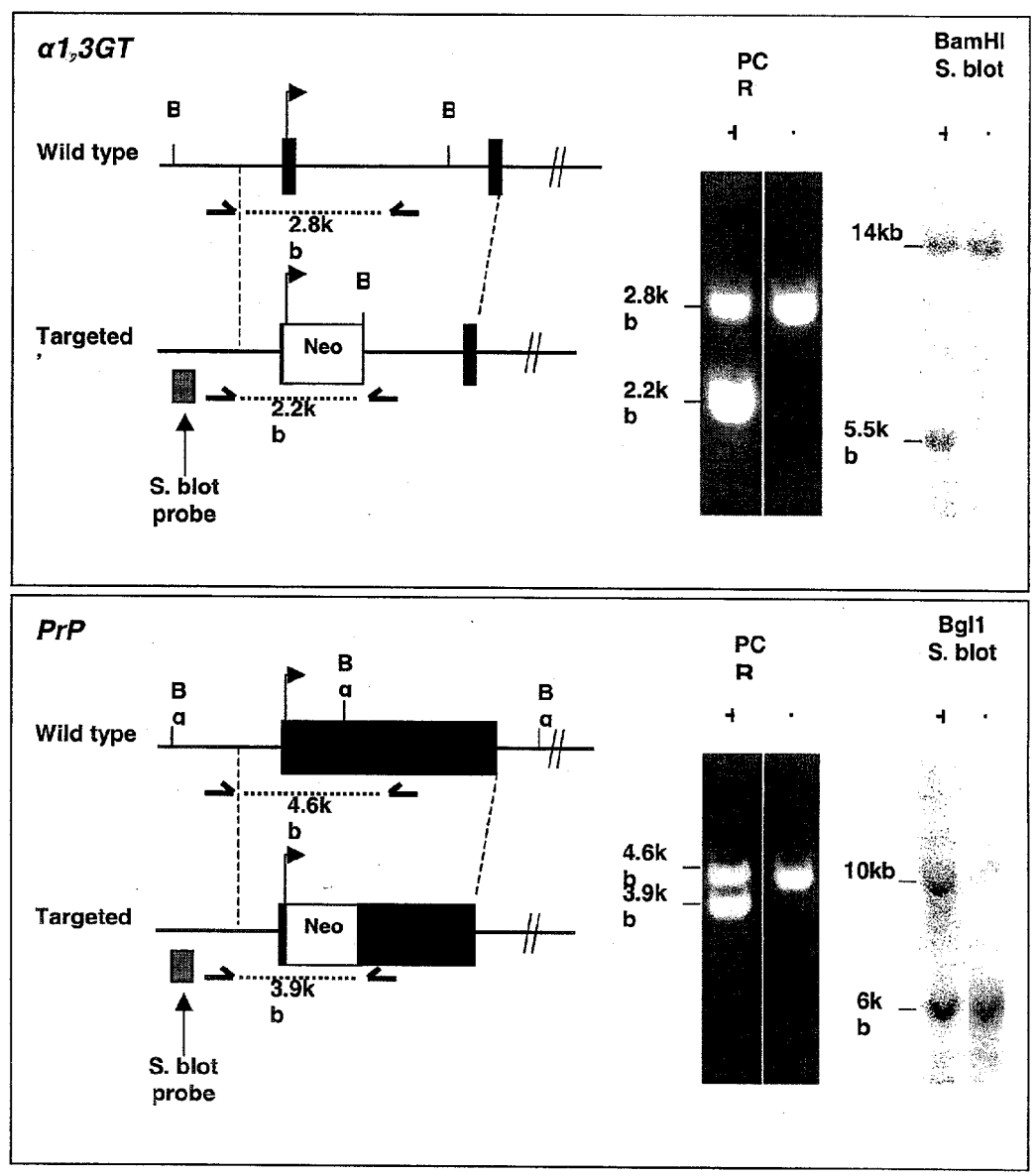

FIG. 5 shows schematically the targeting of the α1,3GT and the PrP genes undertaken in primary sheep fibroblasts. Each targeting vector replaces part of the protein encoding region with a shorter sequence that interrupts the normal encoding region, and simultaneously inserts a drug selection gene, and alters the distance between restriction enzyme cleavage sites. Successfully targeted clones are detected as an altered PCR amplification product, or by a different restriction fragment on Southern blot analysis of BamHI digested DNA.

The frequency of site-specific recombination observed in these experiments is shown in Table 2:

TABLE 2

Gene Targeting Efficiency in Primary Sheep Fibroblast Cultures

| Parental culture | Target locus | Drug resistant colonies | Targeting events detected | Colonies suitable for nuclear transfer |
|---|---|---|---|---|
| Black Welsh | α1,3GT | 877 | 10 (1.1%) | 0 (0%) |
| Black Welsh | PrP | 533 | 55 (10.3%) | 1 (0.2%) |
| Finn Dorset | α1,3GT | 568 | 35 (6.2%) | 2 (0.4%) |

Cells were prepared for nuclear transfer by the method already described, namely serum starvation for 5 days prior to use as a donor. Nuclear transfer is typically conducted as follows. Oocytes are harvested from adult female breeding sheep treated with an analogue of gonadotrophin releasing hormone (Buserelin™, given 24 h after sponge removal). The oocytes are stripped of cumulus cells by triturating with a pipette and incubating with hyaluronidase. They are then enucleated by removing the first polar body and metaphase plate. A single targeted nuclear donor cell is introduced under the zona of each oocyte. The cell combination is subject to simultaneous electrofusion and activation (0.25 kV cm$^{-1}$ AC for 5 sec. to align oocyte and donor cell, followed by 3 pulses of 1.25 kV cm$^{-1}$ DC for 80 μsec to fuse and activate the reconstructed embryo). The activated cell is maintained in culture overnight at 39° C. Next day, the cells are embedded in agar chips to protect from macrophages, and then transferred to the ligated oviduct of a temporary recipient.

Estrous is controlled in the temporary recipient by treatment with intravaginal progestagen sponge for 11 to 16 days, with or with subcutaneous or intramuscular injection of 500 i.u. of PMSG. The timing brings the temporary recipients to estrus ~3 days before the oocyte donors. Cells are collected under general anesthesia using barbiturate followed by gaseous anesthetics. The reproductive tract is exposed by mid-ventral laparotomy; placing ligatures of silk at each utero-tubal junction, and embryos are transferred through the fimbriated end of the oviduct. The laparotomy is then closed, and a long-acting antibiotic is administered. The embryos are flushed from the temporary recipient after 6 days, and developing embryos are removed from the agar chip.

Blastocysts and morula are then transferred into the recipients that will carry the embryo to term. Estrus is controlled by treatment with an intravaginal progestagen sponge for 11 to 16 days, bringing the final recipients to estrus simultaneously with the oocyte donor. The permanent recipients are anesthetized by intravenous barbiturate and gaseous anesthetics, the reproductive tract is exposed by mid-ventral laparotomy, and the oviduct or uterus is temporarily cannulated for transfer of the embryos. Alternatively, three small puncture incisions are made anterior to the udder, and a laparoscope, manipulating forceps and needle are inserted for manipulation of the uterus. The oviduct or uterus is temporarily cannulated for transfer of the embryos, and the incision is sutured closed.

Recipients of oocytes with a targeted nucleus, engrafted in the manner outlined, were monitored for the status of their pregnancy by subcutaneous ultrasonic scanning on a weekly basis. For animals maintaining their pregnancy, the progress of the fetus is monitored regularly by ultrasound, and brought to term. Results are shown in Table 3. The longest-lived animal born with a PrP knockout survived 12 days.

TABLE 3

Nuclear Transfer from Gene Targeted Primary Cells

| | Nuclear donor cell | | |
|---|---|---|---|
| Stage of Animal Cloning | Parental Finn Dorset | α1,3GT targeted | PrP targeted |
| Reconstructions | 126 | 142 | 454 |
| Morula and blastocyst | 33 | 21 | 43 |
| Fetuses at day 60 | 5 | 5 | 8 |
| Lambs at birth; live (dead) | 0 (2) | 0 | 3 (1) |
| Lambs alive at 1 week | 0 | 0 | 1 |

Example 6

Gene Targeting in Telomerized Fibroblasts

Primary Black Welsh fibroblasts (designation BW6F2) were transfected with the hTERT gene as described in Example 1. The characteristics of telomerized clone GRN1.1 are described in Example 2.

GRN1.1 cells at passage 5 or 25 were resuscitated into T175 flasks and grown to subconfluency. Cells (2.8×10$^6$, passage 5; 8.3×10$^6$, passage 25) were electroporated with 10 μg of NotI linearized p0054 targeting vector, using a setting of 125 μF: 350 V in Flowgen™ 0.4 cm/800 μl cuvettes. Diluted cells were plated to 20×96 well plates. The next day, G418 (600 μg/mL) was added to the medium to begin the selection process. Cell death appeared after 8–10 days in G418, much longer than when using parental BW6F2 cells. Colonies were observed after ~2 weeks and replica plated (41 colonies from passage 5 cells; 2 colonies from passage 25 cells) on day 20 of selection.

Figure 6:
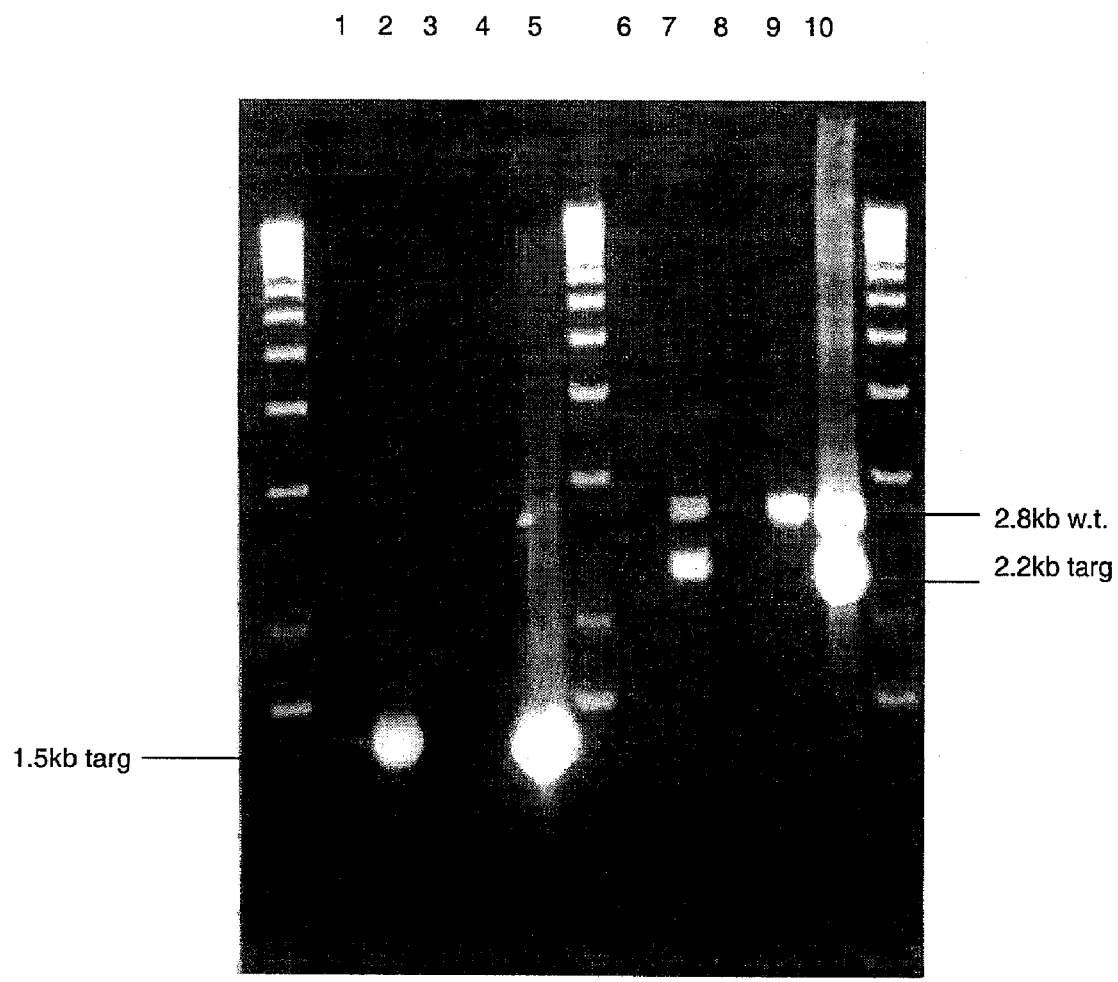

FIG. 6 shows results of PCR analysis on DNA isolated from the selected colonies. Lanes: 1-5=primers for neo gene; 6-10=primers for wild-type or targeted α1,3GT sequence. 1, 6=B9 low DNA conc. (targeted). 2, 7=B9 high DNA conc. (targeted). 3, 8=C9 low DNA conc. 4, 9=C9 high DNA conc. 5, 10=312 targeted positive control DNA. One targeting event (clone B9) was detected from the passage 5 electroporation.

This clone and eight non-targeted clones were resuscitated in 24 well plates. In all cases, cells grew to confluency. The B9 (correctly targeted) cell line, and the C9 cell line (one of the eight containing randomly integrated α1,3GT) grew fastest. Clones B9 and C9 have been karyotyped, and both are 54XY.

Thus, telomerized sheep fibroblasts were successfully targeted with the promoterless neo α1,3GT targeting vector, p0054. The targeted clone (B9) has been expanded, and retains a stable karyotype. This clone exists as a pure population of targeted cells and continues to grow at passage 17 (~80 doublings). Successfully targeted clones can be used for nuclear transfer, or for targeting the same gene on the other allele, thereby creating a homozygous knockout.

Example 7

Targeting and Telomerizing Fibroblasts Simultaneously

This example illustrates the design and use of targeting vectors that can be used to simultaneously inactivate an endogenous gene, and telomerize the cells for improved proliferation and genomic stability.

Figure 7:
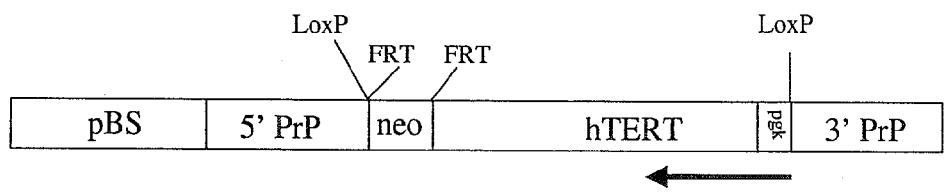
Figure 7:
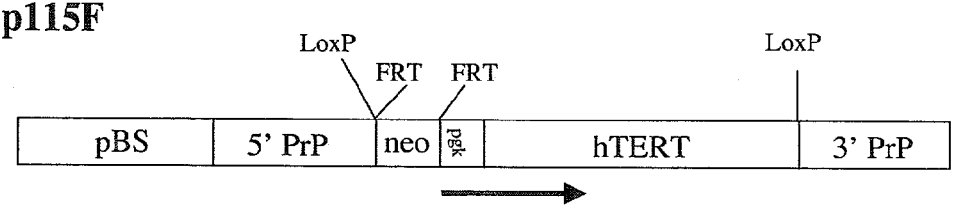

FIG. 7 is a map of the two promoter-less-neo PrP gene knockout targeting vectors that were constructed. Both vectors have a 5' arm and a 3' arm of the sheep PrP gene. The 5' arm is a fusion DNA fragment with the 3' end of sheep PrP gene intron 2 and 5' end of exon 3. The 3' arm is the 3' end of sheep PrP gene exon 3. Contiguous with the sheep PrP 5' arm is the neo resistant gene whose transcription relies on the endogenous PrP promoter. Both vectors have the human telomerase gene (hTERT) inserted between PrP 5' and 3' arms and a phosphoglycerate kinase (PGK) promoter flanking 5' end of hTERT to direct its expression. The pPGK-hTERT gene in the two vectors is forward or reverse orientation, as indicated by arrows (forward for p115F and reverse for p115R). In addition, there are FRT site-specific recombinase sites on both sides of neo (for excision of neo gene with flp recombinase), plus aloxP sites on either side of neo and hTERT (for excision with Cre recombinase).

The p115R or p115F vectors were used to target sheep fibroblasts compared with the p0036 PrP targeting vector which does not contain hTERT. The results are summarized in Table 4.

TABLE 4

PrP Targeting Efficiency using hTERT Containing Vectors

| Parental Line | PrP Targeting Vector | No. of G418 Resistant Colonies | Targeting Events Detected | Targeted Colonies Resuscitated |
|---|---|---|---|---|
| 754F1 (Poll Dorset) | p115R (hTERT) | 114 | 10 (8.8%) | 7 (6.1%) |
| 754F1 (Poll Dorset) | p115F (hTERT) | 291 | 7 (2.4%) | 6 (2%) |
| 59F1 (Poll Dorset) | p0036 (no hTERT) | 59 | 1 (1.7%) | 0 |

Seventeen targeted cell clones were identified, of which 13 reached confluence after resuscitation. Overall, 3.2% of G418 resistant targeted clones were recovered without senescence. This contrasts to recovery frequencies below 1% using PrP targeting vectors without hTERT. Thus, including hTERT in gene targeting vector can increase the effective gene targeting efficiency by more than 10 fold.

Table 5 shows the karyotype analysis of five of the cell lines established from successfully targeted fibroblasts. Thirty cells were analyzed for each line.

TABLE 5

Karyotype of Targeted Cell Lines

| | <52 | 52 | 53 | 54 | 55 | 56 | >56 | Conclusion |
|---|---|---|---|---|---|---|---|---|
| 115F-C5p4 | — | — | — | 30 | — | — | — | 54 XX |
| 115F-A1p4 | — | 1 | — | 29 | — | — | — | 54 XX |
| 115R-D3p6 | — | — | — | 29 | 1 | — | — | 54 XX |
| 115R-B2p5 | 1 | 2 | 3 | 24 | — | — | — | 54 XX |
| 115F-G9p4 | — | 1 | — | 29 | — | — | — | 54 XX |

These results show that in 4 of the 5 cell lines, virtually all the cells had the normal 54 autosomes characteristic of the sheep.

Figure 8:
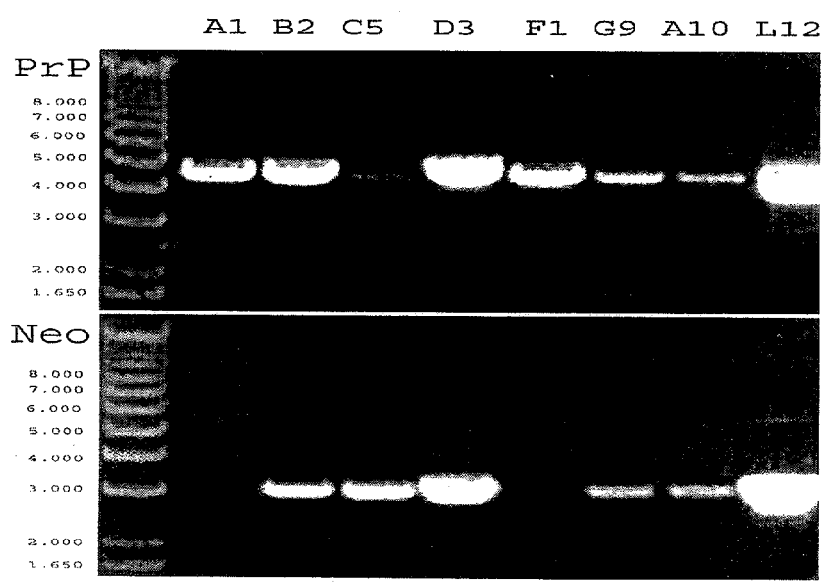
FIG. 8 is a half-tone reproduction of PCR analysis to identify cells in which the PrP gene was successfully targeted, shown by amplification product produced using neo specific primers and decreased amplification product produced using PrP specific primers.

FIG. 8 shows PCR analysis to identify cells in which the PrP gene was successfully targeted. The first primer hybridizes 5' to the PrP intron 2, and has the sequence TTCAGTCGC TCTGTTGTGTCCCA (SEQ. ID NO: 29). The second primer hybridizes at the 3' end of PrP exon 3, and has the sequence AGCATCCC TCCTGCCTTC AGTTCTTC (SEQ. ID NO: 30). Since intron 2 is deleted upon targeting, the second primer but not the first will hybridize where targeting is successful, and no amplification product will be produced (top panel). When the first primer is substituted with a sequence 5' to the neo gene (AGCCGATTG TCTGTTGTGC CCAGTCAT; SEQ. ID NO: 31), amplification product should be obtained.

The results show that the PrP-neo band was amplified for the five targeted lines 115R-B2 (B2), 115R-D3 (D3), 115F-C5 (C5), 115F-G9 (G9) and 115F-A10 (A10), indicating homologous recombination with the targeting vector. Two PrP bands (3.9 and 4.6 Kb) amplified from L12, a cell line previously targeted with the p0036 vector which does not contain hTERT. As predicted, no PCR amplification took place using the neo primer in either the non-targeted cell line, 754F1-A1 (A1) or the parental cell line, 754F1 (F1).

Figure 9:
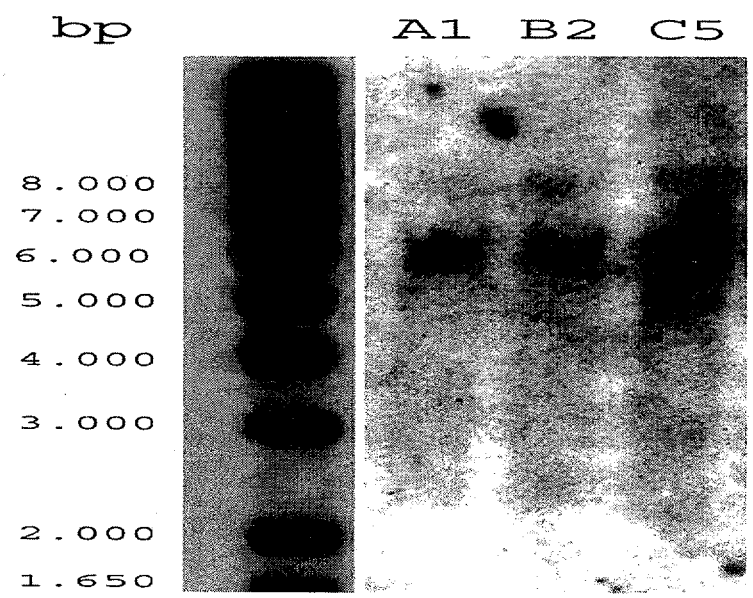
FIG. 9 is a half-tone reproduction of Southern analysis. In cells successfully targeted, a second band of 7.3 kb was detected, corresponding to the targeted allele.

FIG. 9. shows Southern analysis of DNA prepared from resuscitated cells. The PrP probe was 450 bp in length amplified with a pair of PrP specific primers, 21F (CAAAAGAACT AGTTCCCC AATAAAC; SEQ. ID NO: 31) and 21R (TAACAAATT TTACTTGCTGC TTGTG; SEQ. ID NO: 33). The probe hybridizes to intron 2 of the PrP gene, showing a 6 kb BglII band in the wild type. When homologous recombination occurs, this BglII site is deleted and a fragment of 1.3 kb from neo-hTERT added. In cells targeted with either p115R or p115F, the probe detected a second band of 7.3 kb corresponding to the targeted allele.

FIG. 10 shows the telomere restriction fragments (TRF) of targeted and non-targeted cell lines. After DNAs were digested and blotted, a labeled telomere repeat sequence was used to hybridize the blot. The result shows here, that all the targeted cell lines, 115R-B2 (B2), 115R-D3 (D3), 115F-C5 (C5), 115F-G9 (G9) and 115F-A10 (A10) as well as the early passage parental cell line, 754F1 (F1) maintained their telomere lengths. In most differentiated cells, the telomerase activity is not expressed and telomere length shortens with each cell division. Thus, both the non-targeted fibroblast line 754F1-A1 (A1) and cells targeted without telomerization (L12) the telomeres shortened. Human genomic DNA (HG) was used here as control. Quantitation of TRF length is shown in Table 6.

TABLE 6

Characteristics of Targeted Colonies

| Targeted Colony | Targeting Vector | Passage | Targeting Confirmed PCR | Targeting Confirmed Southern | Normal Karyotype | TRF |
|---|---|---|---|---|---|---|
| 115R-B2 | p115R | P5 | + | + | 80% | Long |
| 115R-D3 | p115R | P6 | + | + | 97% | Long |
| 115F-C5 | p115F | P4 | + | + | 100% | Long |
| 115-G9 | p115F | P4 | + | + | 97% | Long |
| 754F1 | | | − | − | 100% | Long |
| 754F1-A1 | | P4 | − | − | 97% | Short |

The telomeres of cell lines simultaneously targeted and telomerized are the same length as early passage sheep fibroblasts—and (unlike non-telomerized cells) are maintained in proliferative culture. It is predicted that these cells are suitable for nuclear targeting with or without further genetic modification.

The compositions and procedures provided in the description can be effectively modified by those skilled in the art without departing from the spirit of the invention embodied in the claims that follow.

TABLE 7

Sequences Listed in this Disclosure

| SEQ. ID NO: | Descriptive Annotation | Species of Origin |
|---|---|---|
| 1 | Sequence of plasmid pGRN145, containing the human TERT sequence. | Artificial construct comprising human TERT, myeloproliferative sarcoma virus (MPSV) promoter, and vector components |
| 2 | α1,3GT cDNA sequence | Sheep |
| 3 | α1,3GT amino acid sequence | Sheep |
| 4 | PrP cDNA sequence | Sheep |
| 5 | PrP cDNA amino acid sequence | Sheep |
| 6 | Sequence of plasmid pWGB5a, in which the hTERT expression cassette is flanked on each side by a loxP recombination recognition site | Artificial construct comprising human TERT, myeloproliferative sarcoma virus (MPSV) promoter, and vector components |
| 7 to 33 | Probes and POR primers | Artificial sequences and sequence fragments |

SEQ. ID NO:1

TGATC ctctagagtcggtgggcctcggggcgggtgcggggtcggcggggccgccccgggtggcttcggtcggag

CCATGGGGTCGTGCGCTCCTTTCGGTCGGGCGCTGCGGGTCGTGGGCGG

GCGTCAGGCACCGGGCTTGCGGGTCATGCACCAGGTCGCGCGGTCCTTCG

GGCACTCGACGTCGGCGGTGACGGTGAAGCCGAGCCGCTCGTAGAAGGGG

AGGTTGCGGGGCGCGGAGGTCTCCAGGAAGGCGGGCACCCCGGCGCGCTC

GGCCGCCTCCACTCCGGGGAGCACGACGGCGCTGCCCAGACCCTTGCCCT

GGTGGTCGGGCGAGACGCCGACGGTGGCCAGGAACCACGCGGGCTCCTTG

GGCCGGTGCGGCGCCAGGAGGCCTTCCATCTGTTGCTGCGCGGCCAGCCG

GGAACCGCTCAACTCGGCCATGCGCGGGCCGATCTCGGCGAACACCGCCC

CCGCTTCGACGCTCTCCGGCGTGGTCCAGACCGCCACCGCGGCGCCGTCG

TCCGCGACCCACACCTTGCCGATGTCGAGCCCGACGCGCGTGAGGAAGAGTTCTTGCAGCTCGGTGACCC

GCTCGATGTGGCGGTcagggtccactgtatggcgtgttgcagGGTAGTCGGCGAACG

TABLE 7-continued

Sequences Listed in this Disclosure

CGGCGGCGAGGGTGCGTACGGCC

CGGGGGACGTCGTCGCGGGTGGCGAGGCGCACCGTGGGCTTGTACTCGGT

CATGGAAGGTCGTCTCCTTGTGAGGGGTCAGGGGCGTGGGTCAGGGGATGGTGGCGG

CACCGGTCGTGGCGGCCGacGGCCTCCAAAAAAGCCTCCTCACTACTTCT

GGAATAGCTCAGAGGCCGAGGCGGCCTCGGCCTCTGCATAAATAAAAAAAATTAGTCAGCCATGGGGCGGAGA

ATGGGCGGAACTGGGCGGAGTTAGGGGCGGGATGGGCGGAGTTAGGGGCG

GGACTATGGTTGCTGACTAATTGAGATGCATGCTTTGCATACTTCTGCCT

GCTGGGGAGCCTGGGGACTTTCCACACCTGGTTGCTGACTAATTGAGATG

CATGCTTTGCATACTTCTGCCTGCTGGGGAGCCTGGGGACTTTCCACACC

CTAACTGACACACATTCCA

CAGcct ggcgcgcg agaTCC

AGACATGATAAGATACATTGATGAGTTTGGACAAACCACAACTAGAATGCAGTGAAAAAAAT

GCTTTATTTGTGAAATTTGTGATGCTATTGCTTTATTTGTAACCATTA

TAAGCTGCAATAAACAAGTTAACAACAACAATTGCATTCATTTTATGTTTCAGGTTCAGGGG

GAGGTGTGGGAGGTTTTTTAAAGCAAGTAAAACCTCTACAAATGTGGTATGGCTGATTATGA

TCTCTAGTCAAGGCACTATACATCAAATATTCCTTATTAACCCCTTTACAAATTAAAAAGCTAAAGGTA

CACAATTTTTGAGCATAGTTATTAATAGCAGACACTCTATGCCTGTGTGGAGTAAGAAAAAACAGTATGTTA

TGATTATAACTGTTATGCCTACTTATAAAGGTTACAGAATATTTTTCCATAATTTTCTTGTATAGCAGTGCA

GCTTTTTCCTTTGTGGTGTAAATAGCAAAGCAAGCAAGAGTTCTATTACTA

AACACAGCATGACTCAAAAAACTTAGCAATTCTGAAGGAAAGTCCTTGGGGTCTTCTACCTTTCTCTTCTTTTTTGGAGGAG

TAGAATGTTGAGAGTCAGCAGTAGCCTCATCATCACTAGATGGCATTTCTTCTGAGCAAAACAGGTTTTCCT

CATTAAAGGCATTCCACCACTGCTCCCATTCATCAGTTCCATAGGTTGGAATCTAAAATACACAAACAATTA

GAATCAGTAGTTTAACACATTATACACTTAAAAATTTTATATTTACCTTATAGCTTTAAATCTCTGTAGGTA

GTTTGTCCAATTATGTCACACCACAGAAGTAAGGTTCCTTCACAAAGATCTAAAGCCAGCAAAAGTCCCATG

GTCTTATAAAAATGCATAGCTTTAGGAGGGGAGCAGAGAACTTGAAAGCATCTTCCTGTTA

GTCTTTCTTCTCGTAGACTTCAAACTTATACTTGATGCCTTTTTCCTCCTGGACCTCAGAG

AGGACGCCTGGGTATTCTGGGAGAA

GTTTATATTTCCCCAAATCAATTTCTGGGAAAAACGTGTCACTTTCAAAT

TCCTGCATGATCCTTGTCACAAAGAGTCTAAGGTGGCCTGGTTGATTCAT

GGCTTCCTGGTAAACAGAACTGCCTCCGACTATCCAAACCATGTCTACTTTACTTG

CCAATTCCGGTTGTTCAATAAGTCTTAAGGCATCAT

CCAAACTTTTGG

CAAGAAAATGAGCTCCTCGTGGTGGTTCTTTGAGTTCTCTACTGAGAACTATATTAATTCTGTCCTTTAAAGGTCGATT

CTTCTCAGGAATGGAGAACCAGGTTTTCCTACCCATAATCACCAGATTCTGTTTACCTTCCACTGAAGAGGTTGTGGTC

ATTCTTTGGAAGTACTTGAACTCGTTCCTGAGCGGAG

GCCAGGGTAGGTCTCCGTTCTTGCCAATCCCCATATTTTGGGACACGGCGACGATGCAGTTCAATGGTCGAACCAT

GATGGCAGCGGGGATAAAATCCTACCAGCCTTCACGCTAGGATTGCCGTCAAGTTTGGCGCGAAATCGCAGCCCTG

TABLE 7-continued

Sequences Listed in this Disclosure

AGCTGTCCC

CCCCCCCAAGCTATTTGCCAAAGCCTGGGCCTCCAAAAAAGC

CTCCTC

ACTACTTCTGGAATAGCTCAGAGGCCGAGGCGGCCTCGGCCTCTGCATAAATAAAAAAAATTAGTCAGCCAT

GGGGCGGAGAATGGGCGGAACTGGGCGGAGTTAGGGGCGGGATGGGCGGAGTTAGGGGCGGGACTATGGTTG

CTGACTAATTGAGATGCATGCTTTGCATACTTCTGCCTGCTGGGGAGCCTGGGGACTTTCCACACCTGGTTG

CTGACTAATTGAGATGCATGCTTTGCATACTTCTGCCTGCTGGGGAGCCTGGGGACTTTCCACACCCT

AACT

GACACACATTCCACAGATCCCGCAAGAGGCCCGGCAGTACCGGCATAACCAAGCCTATGCCTACAGCATCCA

GGGTGACGGTGCCGAGGATGACGATGAGCGCATTGTTAGATTTCATACACGGTGCCTGACTGCGTTAGCAAT

TTAACTGT

GATAAACTACCGCATTAAAGCTAAGCGATTAGTCCAATTTG

TTAAAGACAGGATATCAGTGGTCCA

GGCTCTAGTTTTGACTCAACAATATCACCAGATT

GGCTCTAGTTTTGACTCAACAATATCACCAGCTGAAGCCTATAG

AGTACGAGCCATAGATAGAATAAAAGATTTTATTTAGTCTCCAGAAAAAG

GGGGGAATGAAAGACCCCACCTGTAGGTTTGGCAAGCTAGCTTAAGTAAC

GCCATTTTGCAAGGCATGGAAAATACATAACTGAGAATAGAGAAGTTCAG

ATCAAGGTTAGGAACAGAGAGACAGCAGAATATGGGCCAAACAGGATATC

TGTGGTAAGCAGTTCCTGCCCCGGCTCAGGGCCAAGAACAGTTGGAACAG

CAGAATATGGGCCAAACAGGATATCTGTGGTAAGCAGTTCCTGCCCCGGC

TCAGGGCCAAGAACAGATGGTCCCCAGATGCGGTCCCGCCCTCAGCAGTT

TCTAGAGAACCATCAGATGTTTCCAGGGTGCCCCAAGGACCTGAAATGAC

CCTGTGCCTTATTTGAACTAACCAATCAGTTCGCTTCTCGCTTCTGTTCG

CGCGCTTCTGCTCCCCGAGCTCAATAAAAGAGCCCACAACCCCTCACTCG

GCGCGCCAGTCCTCCGATAGACTGCGTCGCCCG

GGTACC

GAGCTCGAATTGATCTCGAGGAACT

GAAAAACCAGAAAGTTAACTGGTAAGTTTAGTCTTTTTGTCTTTTATTTC

AGGT

CCCGGATCG

GAATTC

CACCATGCCGCGCGCTCCCCGCTGCCGAGCCGTGCGCTCCCTGCT

GCGCAGCCACTACCGCGAGGTGCTGCCGCTGGCCACGTTCGTGCGGCGCCTGGGGCCCCAGGGCTGGCGGCTG

GTGCAGCGCGGGACCCGGCGGCTTTCCGCGCGCTGGTGGCCCAGTGCCTGGTGTGCGTGCCCTGGGACGCAC

GGCCGCCCCCGCCGCCCCTCCTTCCGCCAGGTGTCCTGCCTGAAGGAGCTGGTGGCCCGAGTGCTGCAGAG

GCTGTGCGAGCGCGGCGCGAAGAACGTGCTGGCCTTCGGCTTCGCGCTGCTGGACGGGCCCGCGGGGGCCCC

CCCGAGGCCTTCACCACCAGCGTGCGCAGCTACCTGCCCAACACGGTGACCGACGCACTGCGGGGGAGCGGGG

TABLE 7-continued

Sequences Listed in this Disclosure

CGTGGGGCTGCTGCTGCGCCGCGTGGGCGACGACGTGCTGGTTCACCTGCTGGCACGCTGCGCGCTCTTTGT

GCTGGTGGCTCCCAGCTGCGCCTACCAGGTGTGCGGGCCGCCGCTGTACCAGCTCGGCGCTGCCACTCAGGCC

CGGCCCCCGCCACACGCTAGTGGACCCCGAAGGCGTCTGGGATGCGAACGGGCCTGGAACCATAGCGTCAGGG

AGGCCGGGGTCCCCCTGGGCCTGCCAGCCCCGGGTGCGAGGAGGCGCGGGGGCAGTGCCAGCCGAAGTCTGCC

GTTGCCCAAGAGGCCCAGGCGTGGCGCTGCCCCTGAGCCGGAGCGGACGCCCGTTGGGCAGGGGTCCTGGGCC

GACCCGGGCAGGACGCGTGGACCGAGTGACCGTGGTTTCTGTGTGGTGTCACCTGCCAGACCCGCCGAAGAAG

CCACCTCTTTGGAGGGTGCGCTCTCTGGCACGCGCCACTCCCACCCATCCGTGGGCCGCCACCACCACGCGGG

CCCCCCATCCACATCGCGGCCACCACGTCCCTGGGACACGCCTTGTCCCCCGGTGTACGCCGAGACCAAGCAC

TTCCTCTACTCCTCAGGCGACAAGGAGCAGCTGCGGCCCTCCTTCCTACTCAGCTCTCTGAGGCCCAGCCTGA

CTGGCGCTCGGAGGCTCGTGGAGACCATCTTTCTGGGTTCCAGGCCCTGGATGCCAGGGACTCCCCGCAGGTT

GCCCCGCCTGCCCCAGCGCTACTGGCAAATGCGGCCCCTGTTTCTGGAGCTGCTTGGGAACCACGCGCAGTGC

CCCTACGGGGTGCTCCTCAAGACGCACTGCCCGCTGCGAGCTGCGGTCACCCCAGCAGCCGGTGTCTGTGCCC

GGGAGAAGCCCCAGGGCTCTGTGGCGGCCCCCGAGGAGGAGGACACAGACCCCCGTCGCCTGGTGCAGCTGCT

CCGCCAGCACAGCAGCCCCTGGCAGGTGTACGGCTTCGTGCGGGCCTGCCTGCGCCGGCTGGTGCCCCCAGGC

CTCTGGGGCTCCAGGCACAACGAACGCCGCTTCCTCAGGAACACCAAGAAGTTCATCTCCCTGGGGAAGCATG

CCAAGCTCTCGCTGCAGGAGCTGACGTGGAAGATGAGCGTGCGGGACTGCGCTTGGCTGCGCAGGAGCCCAGG

GGTTGGCTGTGTTCCGGCCGCAGAGCACCGTCTGCGTGAGGAGATCCTGGCCAAGTTCCTGCACTGGCTGATG

AGTGTGTACGTCGTCGAGCTGCTCAGGTCTTTCTTTTATGTCACGGAGACCACGTTTCAAAAGAACAGGCTCT

TTTTCTACCGGCCGAGTGTCTGGAGCAAGTTGCAAAGCATTGGAATCAGACAGCACTTGAAGAGGGTGCAGCT

GCGGGAGCTGTCGGAAGCAGAGGTCAGGCAGCATCGGGAAGCCAGGCCCGCCCTGCTGACGTCCAGACTCCGC

TTCATCCCCAAGCCTGACGGGCTGCGGCCGATTGTGAACATGGACTACGTCGTGGGAGCCAGAACGTTCCGCA

GAGAAAAGAGGGCCGAGCGTCTCACCTCGAGGGTGAAGGCACTGTTCAGCGTGCTCAACTACGAGCGGGCGCG

GCGCCCCGGCCTCCTGGGCGCCTCTGTGCTGGGCCTGGACGATATCCACAGGGCCTGGCGCACCTTCGTGCTG

CGTGTGCGGGCCCAGGACCCGCCGCCTGAGCTGTACTTTGTCAAGGTGGATGTGACGGGCGCGTACGACACCA

TCCCCCAGGACAGGCTCACGGAGGTCATCGCCAGCATCATCAAACCCCAGAACACGTACTGCGTGCGTCGGTA

TGCCGTGGTCCAGAAGGCCGCCCATGGGCACGTCCGCAAGGCCTTCAAGAGCCACGTCTCTACCTTGACAGAC

CTCCAGCCGTACATGCGACAGTTCGTGGCTCA

CCTGCAGG

AGACCAGCCCGCT

GAGGGATGCCGTCGTCATCGAGCAGAGCTCCTCCCTGAATGAGGCCAGCAGTGGCCTCTTCGACGTCTTCCTA

CGCTTCATGTGCCACCACGCCGTGCGCATCAGGGGCAAGTCCTACGTCCAGTGCCAGGGGATCCCGCAGGGCT

CCATCCTCTCCACGCTGCTCTGCAGCCTGTGCTACGCGACATGGAGAACAAGCTGTTTGCGGGGATTCGGCG

GGACGGGCTGCTCCTGCGTTTGGTGGATGATTTCTTGTTGGTGACACCTCACCTCACCCACGCGAAAACCTTC

CTCAGGACCCTGGTCCGAGGTGTCCCTGAGTATGGCTGCGTGGTGAACTTGCGGAAGACAGTGGTGAACTTCC

CTGTAGAAGACGAGGCCCTGGGTGGCACGGCTTTTGTTCAGATGCCGGCCCACGGCCTATTCCCCTGGTGCGG

CCTGCTGCTGGATACCCGGACCCTGGAGGTGCAGAGCGACTACTCCAGCTATGCCCGGACCTCCATCAGAGCC

AGTGTCACCTTCAACCGCGGCTTCAAGGCTGGGAGGAACATGCGTCGCAAACTCTTTGGGGTCTTGCGGCTGA

AGTGTCACAGCCTGTTTCTGGATTTGCAGGTGAACAGCCTCCAGACGGTGTGCACCAACATCTACAAGATCCT

CCTGCTGCAGGCGTACAGGTTTCACGCATGTGTGCTGCAGCTCCCATTTCATCAGCAAGTTTGGAAGAACCCC

TABLE 7-continued
Sequences Listed in this Disclosure

ACATTTTTCCTGCGCGTCATCTCTGACACGGCCTCCCTCTGCTACTCCATCCTGAAAGCCAAGAACGCAGGGA

TGTCGCTGGGGGCCAAGGGCGCCGCCGGCCCTCTGCCCTCCGAGGCCGTGCAGTGGCTGTGCCACCAAGCATT

CCTGGTCAAGCTGACTCGACACCGTGTCACCTACGTGCCACTCCTGGGGTCACTCAGGACAGCCCAGACGCAG

CTGAGTCGGAAGCTCCCGGGACGACGCTGACTGCCCTGGAGGCCGCAGCCAACCCGGCACTGCCCTCAGACT

TCAAGACCATCCTGGACTGA

TGGGAC

GCGGCCGC

TCTAGAACTAGTGGATCCCCCGGGCTGCAG

GAATTC

TCACGTGCGGATCCACCTAGGTGTCGACCTGCAGGTCGCGAAGCTTCGATCCAG

ACATGATAAGATACATTGATGAGTTTGGACAAACCACAACTAG

AATGCAGTGAAAAAAATGCTTTATTTGTGAAATTTGTGATGCTATTGCTT

TATTTGTAACCATTATAAGCTGCAATAAACAAGTTAACAACAACAATTGC

ATTCATTTTATGTTTCAGGTTCAGGGGGAGGTGTGGGAGGTTTTTTAAAG

CAAGTAAAACCTCTACAAATGTGGTATGGCTGATTATGATCCGGCTGCCT

CGCGCGTTTCGGTGATGACGGTGAAAACCTCTGACACATGCAGCTCCCGG

AGACGGTCACAGCTTGTCTGTAAGCGGATGCCGGGAGCAGACAAGCCCGT

CAGGGCGCGTCAGCGGGTGTTGGCGGGTGTCGGGGCGCAGCCATGACCCA

GTCACGTAGCGATAGCGGAGTGTATTCGAGCTCGGACATTGATTATTG

ACTAGT

TATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTT

TGACTCACGGGGATTTCCAAGTCTCCACCCAG

CGGACCC

CGTCCCTAAC

CCACGGGGCCCGTGG

CTATGGCAGGGCCTGC

CGCCCCGACGTTGGCTGCGAGCCCTGGGCCTTCACCCGAACTTGGGGGGTGGGTGGGAAAAGGAAGAAACGCGGGCGTAT

TGGCCCCAATGGGGTCTCGGTGGGGTATCGACAGAGTGCCAGCCCTGGGACCGAACCCCGCGTTTATGAACA

AACGACCCAACACCCGTGCGTTTTATTCTGTCTTTTTATTGCCGTCATAGCGCGGGTTCCTTCCGGTATTGT

CTCCTTCCGTGTTTCAGTTAGCCTCCCCCATCTCCCCAGATCTGCACCCAATCGGCAGGCACGGGCGGCGAT

TABLE 7-continued

Sequences Listed in this Disclosure

CTCCAATCTGCGGGATCAGTCAGATCACCCGAGT

GCGTGGGCATGACAATCGTGCCCTGGGGACCAACACAATCCAGAAGGGCCTGAATCACTGCGACCGGCCCTC

CCGCGACCCAGCCGAGCGAGCTTAGCGAACTGTGGACGAGAACTGTGCCACCAAGCGTAAGGCCGTTCTCTC

GCATTTGCCTTGCTAGGCTCGCGCGAGTTGCTGGCTGAGGCGTTCTCGAAATCAGCTCTTGTTCGGTCGGCA

TCTACTCTATTCCTTTGCCCTCGGACGAGTGCTGGGGCGTCGGTTTCCACTATCGGCGAGTACTTCTACACA

GCCATCGGTCCAGACGGCCGCGCTTCTGCGGGCGATTTGTGTACGCCCGACAGTCCCGGCTCCGGATCGGAC

GATTGCGTCGCATCGACCCTGCGCCCAAGCTGCATCATCGAAATTGCCGTCAACCAAGCTCTGATAGAGTTG

GTCAAGACCAATGCGGAGCATATACGCCCGGAGCCGCGGCGATCCTGCAAGCTCCGGATGCCTCCGCTCGAA

GTAGCGCGTCTGCTGCTCCATACAAGCCAACCACGGCCTCCAGAAGAAGATGTTGGCGACCTCGTATTGGGA

ATCCCCGAACATCGCCTCGCTCCAGTCAATGACCGCTGTTATGCGGCCATTGTCCGTCAGGACATTGTTGGA

GCCGAAATCCGCGTGCACGAGGTGCCGGACTTCGGGGCAGTCCTCGGCCCAAAGCATCAGCTCATCGAGAGC

CTGCGCGACGGACGCACTGACGGTGTCGTCCATCACAGTTTGCCAGTGATACACATGGGGATCAGCAATCGC

GCATATGAAATCACGCCATGTAGTGTATTGACCGATTCCTTGCGGTCCGAATGGGCCGAACCCGCTCGTCTG

GCTAAGATCGGCCGCAGCGATCGCATCCATGGCCTCCGCGACCGGCTGCAGAACAGCGGGCAGTTCGGTTTC

AGGCAGGTCTTGCAACGTGACACCCTGTGCACGCCGGGAGATGC

AATAGGTCAGGCTCTCGCTGAACTCCCCGATATCAAGCACTTCCGGAA

TCGGGAGCGGCGCCGATGCAAAGTGCCGATAAACATAACGATCTTTGTAGAA

ACCATCGGCGCAGCTATTTACCCGCAGGACATATCCACGCCCTCCTACATCGAAGCTGAAAGCACGAGATTC

TTCGCCCTCCGAGAGCTGCATCAGGTCGGAGACGCTGTCGAACTTTTCGATCAGAAACTTCTCGACAGACGT

CGCGGTGAGTTCAGGCTTTTTCATATCTCCCGGATCTGCGGCACGCTGTTGACGCTGTT

AACCGGGTCGCTGCAGGGTCGCTCGGTGTTCGAGGCCACACGCGTCACCTTAATATGCGAAGTGGACCTCGG

ACCGCGCCGCCCCGACTG

CATCTGCGTGTTCGGATTCGCCAATGACAAG

ACGCTGGGCGGGGTTTGTGTCAT

CATAGAACTAAAGACATGCAAATATATTTCTTCCGGGGACACCGCCAGCAAACGCGAGCAACGGGCCACGGG

GATGAAGCAGTTAATGCGGTAGTTTATCACAGTTAAATTGCTAACGCAGTCAGGCACCGTGT

ATGAAATCTAACAATGCGCTCATCGTCATCCTCGGCACCGTCACCCTGGATGCTGTAGGCATAGGCTTGGT

TATGCCGGTACTGCCGGGCCTCTTGCGGGATATCGTCCATTCCGACAGCATCGCCAGTCACTATGGCGTGC

TGCTAGCGCTATATGCGTTG

ATGCAATTTCTA

TGCGTA

AGAGGTTCCAACTTTCACCATAATGAAATAAG

ATCACTACCGGGCGTATTTTTTGAGTTATCGAGATTTTCAGGAGCTAAGGAAGCTAAAATGGAGAAAAAAATCACTGGAT

ATACCACCGTTGATATATCCCAATGGCATCGTAAAGAACATTTTGAGGCATTTCAGTCAGTTGCTCAATGTACCTATAAC

CAGACCGTTCAGCTGGATATTACGGCCTTTTTAAAGACCGTAAAGAAAAATAAGCACAAGTTTTATCCGGCCTTTATTCA

CATTCTTGCCCGCCT

GATGAATGCTCATCCCGAGTTCCGTATGGCA

ATGAAAGACGGTGAGCTGGTGATATGGGATAGTG

TTCACCCTTGTTACACCGTTTTCCATGAGCAAACTGAAACGTTTTCATCGCTCTGGAGTGAATACCACGACGATTTCCGG

TABLE 7-continued

Sequences Listed in this Disclosure

CAGTTTCTACACATATATTCGCAAGATGTGGCGTGTTACGGTGAAAACCTGGCCTATTTCCCTAAAGGGTTTATTGAGAA

TATGTTTTTCGTCTCAGCCAATCCCTGGGTGAGTTTCACCAGTTTTGATTTAAACGTGGCCAATATGGACAACTTCTTCG

CCCCCGTTTTCACCATGGGCAAATATTATACGCAAGGCGACAAGGTGCTGATGCCGCTGGCGATTCAGGTTCATCATGCC

GTTTGTGATGGCTTCCATGTCGGCAGAATGCTTAATGAATTACAACAGTGTACCGCATCAGGCGAAATTGTAAACGTTAA

TATTTTGTTAAAATTCGCGTAAATATTTGTTAAATCAGCTCATTTTTTAACCAATAGGCCGAAATCGGCAAAATCCCTTA

TAAATCAAAAGAATAGACCGAGATAGGGTTGAGTGTTGTTCCAGTTTGGAACAAGAGTCCACTATTAAAGAACGTGGACT

CCAACGTCAAAGGGCGAAAAACCGTCTATCAGGGCGATGGCCCACTACGTGAACCATCACCCAAATCAAGTTTTTTGCGG

TCGAGGTGCCGTAAAGCTCTAAATCGGAACCCTAAAGGGAGCCCCCGATTTAGAGCTTGACGGGAAAGCCGGCGAACGT

GGCGAGAAAGGAAGGGAAGAAAGCGAAAGGAGCGGGCGCTAGGGCGCTGGCAAGTGTAGCGGTCACGCTGCGCGTAACCA

CCACACCCGCCGCGCTTAATGCGCCGCTACAGGGCGCGTCCATTCGCCATTCAGGCTGCCTGCATTAATGAATCGGCCAA

CGCGCGGGAGAGGCGGTTTGCGTATTGGGCGCTCTTCCGCTTCCTCGCTCAC

TCA

CTC

GCTGCGCTCGGTCGTTCGGCTGCGGCGAGCGGTATCAGCTCACTCAAAGGCGGTAATACGGTTATCCACAG

AATCAGGGGATAACGCAGGAAAGAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGACGCTCAAGTCAGAGGT

GGCGAAACCCGACAGGACTATAAAGATACCAGGCGTTTCCCCCTGGAACCTCCCTCGTGCGCTCTCCTGTTC

CGACCCTGCCGCTTACCGGATACCTGTCCGCCTTTCTCCCTTCGGGAAGCGTGGCGCTTTCTCAATGCTCAC

GCTGTAGGTATCTCAGTTCGGTGTAGGTCGTTCGCTCCAAGCTGGGCTGTGTGCACGAACCCCCCGTTCAGC

CCGACCGCTGCGCCTTATCCGGTAACTATCGTCTTGAGTCCAACCCGGTAAGA

CACGAC

TTATCGCCACTGGCAGCAGCCACTGGTAACAGGATTAGCAGAGCGAGGTATGTAGGCGGTGCTACA

GAGTTCTTGAAGTGGTGGCCTAAC

TACGGCTACACTAGAAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAGATTACGCGCAGAAA

AAAAGGATCTCAAGAAGATCCTTT

GATCTTTTCTACGGGGTCTGACGCTCAGTGGAACGAA

AACTCA

CGTTAAGGGATTTTGGTCATGAGATTATCAAAAAGGATCTTCACCTAGATCCTTTTA

AATTAAAAATGAAGTTTTAAATCAATCTAAAGTATATATGAGTAAACTTGGTCTGACAGTTACCAATGCTTAATCA

GTGAGGCACCTATCTCAGCGATCT

GTCTATTTCGTTCATCCATAGTTGCCTGACTCCCCGTCGTGTAGATAACTACGATACGGGAGGGCTTACCATCTGG

CCCCAGTGCTGCAATGATACCGCG

AGACCCACGCTCACCGGCTCCAGATTTATCAGCAATAAACCAGCCAGCCGGAAGGGCCGAGCGCAGAAGTGGTCCT

GCAACTTTATCCGCCTCCATCCAG

TCTATTAATTGTTGCCGGGAAGCTAGAGTAAGTAGTTCGCCAGTTAATAGTT

TGCGCA

ACGTTGTTGCCATTGCTGCAGGCATCGTGGTGTCACGCTCGTCGTTTGGT

TABLE 7-continued

Sequences Listed in this Disclosure

ATGGGTTCATTCAGCTCCGGTTCCCAACGATCAAGGCGAGTTACATGATCCCCCATGTT

GTGCAAAAAAGCGGTTAGCTCCTTCGGTCCTCCGATCGTTGTCAGAAGTAAGTTGGCCG

CAGTGTTATCACTCATGGTTATGGCAGCACTGCATAATTCTCTTACTGTCATGCCATCC

GTAAGATGCTTTTCTGTGACTGGTGAGTACTCAACCAAGTCATTCTGAGAATAGTGTAT

GCGGCGACCGAGTTGCTCTTGCCCGGCGTCAACACGGGATAATACCGCGCCACATAGCA

GAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTT

CAGCAT

CTTTTACTTTCACCAGCGTTTCTGTGGTGAGGAAAAACAGGAAG

GCAAAATGCCGC

AAAAAAGGGAATAAGGGCGACACGGAAATGTTGAATACTCATACTCTTCCTTTTTCAATAT

TATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTT

CGTCTTC

AGCCGAGGACGCCGCCGGGGAGCCGAGGCTCCGGCCAGCCCCCAGCGCGCCCAGCTTCTG    SEQ. ID NO:2

CAGATCAGG

AGTCAGAACGCTGCAC

CTTCGCTTCCTCCCAGCCCTGCCTCCTTCTGCAAAACGGAGCTCAATAGAACTTGGTACT

TTTGCCTTTTACTCTGGGAGGAGAGAAGCAGACGATGAGGAGAAAATA

[beginning of coding sequence]
ATGAATGTCAAA

GGAAAAGTGATTCTGTCAATGCTGGTTGTCTCAACTGTCATTGTTGTGTTTTGGGAATAT

ATCCACAGCCCAGAAGGCTCTTTGTTCTGGATAAACCCATCAAGAAACCCAGAAGTCAGT

GGCGGCAGCAGCATTCAGAAGGGCTGGTGGTTTCCGAGATGGTTTAACAATGGTTACCAA

GAAGAAGATGAAGACGTAGACGAAGAAAAGGAACAAAGAAAGGAAGACAAAAGCAAGCTT

AAGCTATCGGACTGGTTCAACCCATTTAAACGCCCTGAGGTTGTGACTATGAGAGATTGG

AAGGCACCCGTGGTGTGGGAAGGCACTTACAACAGAGCCGTCTTAGACGATTACTACGCC

AAGCAGAAAATTACCGTCGGCCTGACGGTTTTCGCCGTCGGAAGATACATTGAGCATTAC

TTGGAGGAGTTCTTAACGTCTGCTAATAAGCACTTCATGGTTGGCCACCGAGTCATCTTT

TACGTCATGGTGGACGACGTCTCCAGGATGCCTTTGATAGAGCTGGGCCCTCTGCGCTCC

TTCAAAGTGTTTGAGGTCAAGCCTGAGAGGAGGTGGCAGGACGTCAGCATGGTGCGCATG

AAGACCATCGGGGAGCACATCGTGGCCCACATCCAGCGTGAGGTTGACTTCCTCTTCTGC

ATGGACGTGGACCAGGTCTTCCAAGACGAGTTCGGGGTGGAGACCCTGGGTGAGTCGGTG

GCCCAGCTACAGGCCTGGTGGTACAAGGCAGATCCCGATGAGTTTACCTACGAGAGGCGC

AAGGAGTCTGCAGCATACATTCCCTTCGGCGAAGGGGATTTTTATTACCACGCAGCCATT

TTTGGGGGAACACCCACTCAGGTCCTTAACATCACCCAGGAATGCTTCAAAGGAATCCTC

AAGGACAAGAAAAATGACATAGAAGCCCAATGGCATGATGAGAGCCATCTAAACAAGTAT

TTCCTTCTCAACAAACCCACTAAAATCTTATCCCCGGAATACTGCTGGGATTATCATATA

TABLE 7-continued

Sequences Listed in this Disclosure

GGCCTACCTGCGGATATTAAGCTTGTCAAGATGTCTTGGCAGACAAAAGAGTATAATGTG

GTTAGAAATAACGTCTGA

[end of coding sequence]

SEQ. ID NO:3

MNVKGKVILS MLVVSTVIVV FWEYIHSPEG SLFWINPSRN PEVSGGSSIQ

KGWWFPRWFN NGYQEEDEDV DEEKEQRKED KSKLKLSDWF NPFKRPEVVT

MTDWKAPVVW EGTYNRAVLD DYYAKQKITV GLTVFAVGRY IEHYLEEFLT

SANKVIFYVMVDD VSRMPLIELG PLRSFKVFEV KPERRWQDVS

MVRMKTIGEH IVAHIQREVD FLFCMDVDQV FQDEFGVETL GESVAQLQAW

WYKADPDEFT YERRKESAAY IPFGEGDFYY HAAIFGGTPT QVLNITQECF

KGILKDKKND IEAQWHDESH LNKYFLLNKP TKILSPEYCW DYHIGLPADI

KLVKMSWQTK EYNVVRNNV*

SEQ. ID NO:4

```
   1 ctgcagactt taagtgattc ttacgtgggc atttgatgct gacaccctct ttattttgca
  61 gagaagtcat catggtgaaa agccacatag gcagttggat cctggttctc tttgtggcca
 121 tgtggagtga cgtgggcctc tgcaagaagc gaccaaaacc tggcggagga tggaacactg
 181 ggggagccg ataccgggA cagggcagtc ctggaggcaa ccgctatcca cctcagggag
 241 gggtggctg gggtcagccc catggaggtg gctgggccA acctcatgga ggtggctggg
 301 gtcagcccca tggtggtggc tggggacagc cacatggtgg tggaggctgg ggtcaaggtg
 361 gtagccacag tcagtggaac aagcccagta agccaaaaac caacatgaag catgtggcag
 421 gagctgctgc agctggagca gtggtagggg gccttggtgg ctacatgctg ggaagtgcca
 481 tgagcaggcc tcttatacat tttggcaatg actatgagga ccgttactat cgtgaaaaca
 541 tgtaccgtta ccccaaccaa gtgtactaca gaccagtgga tcggtatagt aaccagaaca
 601 actttgtgca tgactgtgtc aacatcacag tcaagcaaca cacagtcacc accaccacca
 661 aggggagaa cttcaccgaa actgacatca agataatgga gcgagtggtg gagcaaatgt
 721 gcatcaccca gtaccagaga gaatcccagg cttattacca aagggggca agtgtgatcc
 781 tcttttcttc ccctcctgtg atcctcctca tctctttcct cattttctc atagtaggat
 841 agggcaacc ttcctgtttt cattatcttc ttaatctttg ccaggttggg ggagggagtg
 901 tctacctgca gccctgtagt ggtggtgtct catttcttgc ttctctcttg ttacctgtat
 961 aataataccc ttggcgctta cagcactggg aaatgacaag cagacatgag atgctattta
1021 ttcaagtccc attagctcag tattctaatg tcccatctta gcagtgattt tgtagcaatt
1081 ttctcatttg tttcaagaac acctgactac atttcccttt gggaatagca tttctgccaa
1141 gtctggaagg aggccacata atattcattc aaaaaaacaa aactggaaat ccttagttca
1201 tagacccagg gtccaccctg ttgagagcat gtgtcctgtg tctgcagaga actataaagg
1261 atattctgca ttttgcaggt tacatttgca ggtaacacag ccatctattg catcaagaat
1321 ggatattcat gcaaccttg acttatgggc agaggacatc ttcacaagga atgaacataa
1381 tacaaaggct tctgagacta aaaaattcca acatatggaa gaggtgccct tggtggcagc
1441 cttccatttt gtatgtttaa agcaccttca agtgatattc ctttctttag taacataaag
1501 tatagataat taggtaccct taattaaact accttctaga cactgagagc aaatctgttg
```

TABLE 7-continued

Sequences Listed in this Disclosure

```
1561 tttatctgga acccaggatg attttgacat tgcttaggga tgtgagagtt ggactgtaaa 1621 gaaagctgag tgctgaagag ttcatgcttt tgaactatag tgttggagaa aactcttgag 1681 agtcccttgg actgaaagga gatcagtcct gaatattcat tggaaggact gatgctgaag 1741 ctgaaactcc agtactttgg tcacctgatg ggaagaactg aaggcaggag ggatgctagg 1801 aaagactgaa ggcaggagga gaaggggacg acagaggatg agatggctag atggcatcat 1861 ggactcaatg gacatgagct taagtaaact ccaggagttg gcaatggaca gggagacctg 1921 gcgtcctgca gtccatggtg tcgcagagtc ggacacgatt gagtgactaa attgaggtga 1981 cccagattta acatagagaa tgcagataca aaactcatat tcatttgatt gaatcttttc 2041 ctgaaccagt gctagtgttg gactggtaag ggtataacag catatatagg ttatgtgatg 2101 aagagatagt gtacatgaaa tatgtgcatt tctttattgc tgtcttataa ttgtcaaaaa 2161 agaaaattag gtccttggtt tctgtaaaat tgacttgaat caaagggag gcatttaaag 2221 aaataaatta gagatgatag aaatctgatc cattcagagt agaaaagaa attccattac 2281 tgttattaaa gaaggtaaaa ttattccctg aattgttcaa tattgtcacc tagcagatag 2341 acactattct gtactgtttt tactagcttg caccttgtgg tatcctatgt aaaaacatat 2401 ttgcatatga caaactttt ctgttagagc aattaacatc tgaaccacct aatgcattac 2461 ctgttttgt aaggtacttt ttgtaaggta ctaaggagat gtgggtttaa tccctaggtc 2521 aggtaaatcc cctagaggaa gaaatggcaa cccactccag tattcttgcc aggaaaatcc 2581 agtgggcaga ggagcctggc agggtacagt ctgagcatgg ggttgcaaag agtgagacaa 2641 gacttgagct actgaacaat aaggacaata aatgctgggt cggctaaaag gttcattagg 2701 ttttttttct gtaagatggc tctagtagta cttgtcttta tcttcattcg aaacaatttt 2761 gttagattgt atgtgacagc tcttgtatca gcatgcattt gaaaaaaaca tcacaattgg 2821 taaattttg tatagccatc ttactattga agatggaaga aaagaagcaa aattttcagc 2881 atatcatgct gtacttattt caagaaagat aaccaaaatg caaaaatgta tttgtgaagt 2941 gtatggagaa ggggctgcaa ctgatcaagc ttgtcaaagt agtttgtgaa gtttcgtgct 3001 ggagatttct tattggacga tgctccacag ttggatatac cagttgaagt tgatagtgat 3061 caaattgaga tattgagaat aatcgatgtt ataccacgcg ggagatagct gacatactca 3121 aaatatccaa atagaacctt gaaaaccatt tgcaccatct cagttatgtt aatcactttg 3181 atgtttgagt tccacataag caaaaaaaca acaacaaaaa aaaatacaac cttgaccata 3241 tttgcgcatg cagttctcta ctgaaatgat tgaaaacact ttgtttttaa aaacagattt 3301 tgattaacag tgggtacgat acaataacgt agatggaaga aattgtaggg tgagcaaaat 3361 gaaccacacc accaaaggcc agtcttcctc taaagaagat gtgtgtatgg tgggattgga 3421 aagtaatcct ctattatgaa ttcttctgga aaacactgct cctaattaga ccaactgaaa 3481 acagcactca acgaaaagca tccagaatta gtcaatagaa aacataatct tccatcagga 3541 taacgcaaga ctacatattt ctttgatgac ccagcatggc tggagtttct gattcatctg 3601 ttgtattcag acgttgcatc tttggatttt ttccatttat ttcagtctac aaaattatca 3661 taatggaaaa aatttccatt ccctggaaga tgtaaagtgc atctggaaaa tttctttgct 3721 caaaaagata aaaagttttg tgaacacaga attatgacgt tgcctgaaaa atggcagaag 3781 gtagtggaac aaaagagtga ctatgttgtt tggtaaagtt cttagtgaaa atgaaaaatg 3841 tgtcttttat ttttatttaa acaccaaagg cacattttag caacccaata ctgaatctaa
```

TABLE 7-continued

Sequences Listed in this Disclosure

```
3901 aggaaactct tctgtgtgtt gtccttacag tgtgcactga tagtttgtat aagaatccag
3961 agtgatattt gaaatacgca tgtgcttata tttttttatat ttgtaacttt gcatgtactt
4021 gttttgtgtt aaaagtttat aaatatttaa tatctgacta aaattaaaca ggagctaaaa
4081 ggagtatctt ccacggagtt gtctggctgt gttcaccaga tgtgcacaca tgttggcagc
4141 ttcatttggg gggttaatat gagaaaagtg acacattcag tcctcacact gccaattgca
4201 ggaggagggc tactcctgat cctgcttcag ccttattccc agtcacatgc cagctg
```

SEQ. ID NO:5

MVKSHIGSWILVLFVAMWSDVGLCKKRPKPGGGWNTGGSRYPGQ

GSPGGNRYPPQGGGGWGQPHGGGWGQPHGGGWGQPHGGGWGQGGSHSQW

NKPSKPKTNMKHVAGAAAAGAVVGGLGGYMLGSAMSRPLIHFGNDYEDRYYRENMYRY

PNQVYYRPVDRYSNQNNFVHDCVNITVKQHTVTTTTKGENFTETDIKIMERVVEQMCI

TQYQRESQAYYQRGASVILFSSPPVILLISFLIFLIVG

SEQ. ID NO:6

```
   1 CGGCCGCCGG CAGATCTGAT CCTGATCATA ACTTCGTATA GCATACATTA
  51 TACGAAGTTA TCATGAGATC CGACCTCGAG GCCGCTCTAG AACTAGTGGA
 101 TCCAGACATG ATAAGATACA TTGATGAGTT TGGACAAACC ACAACTAGAA
 151 TGCAGTGAAA AAAATGCTTT ATTTGTGAAA TTTGTGATGC TATTGCTTTA
 201 TTTGTAACCA TTATAAGCTG CAATAAACAA GTTAACAACA ACAATTGCAT
 251 TCATTTTATG TTTCAGGTTC AGGGGGAGGT GTGGGAGGTT TTTTAAAGCA
 301 AGTAAAACCT CTACAAATGT GGTATGGCTG ATTATGATCT CTAGTCAAGG
 351 CACTATACAT CAAATATTCC TTATTAACCC CTTTACAAAT TAAAAAGCTA
 401 AAGGTACACA ATTTTTGAGC ATAGTTATTA ATAGGAGACA CTCTATGCCT
 451 GTGTGGAGTA AGAAAAAACA GTATGTTATG ATTATAACTG TTATGCCTAC
 501 TTATAAAGGT TACAGAATAT TTTTCCATAA TTTTCTTGTA TAGCAGTGCA
 551 GCTTTTTCCT TGTGGTGTA AATAGCAAAG CAAGCAAGAG TTCTATTACT
 601 AAACACAGCA TGACTCAAAA AACTTAGCAA TTCTGAAGGA AAGTCCTTGG
 651 GGTCTTCTAC CTTTCTCTTC TTTTTTGGAG GAGTAGAATG TTGAGAGTCA
 701 GCAGTAGCCT CATCATCACT AGATGGCATT TCTTCTGAGC AAAACAGGTT
 751 TTCCTCATTA AAGGCATTCC ACCACTGCTC CCATTCATCA GTTCCATAGG
 801 TTGGAATCTA AAATACACAA ACAATTAGAA TCAGTAGTTT AACACATTAT
 851 ACACTTAAAA ATTTTATATT TACCTTAGAG CTTTAAATCT CTGTAGGTAG
 901 TTTGTCCAAT TATGTCACAC CACAGAAGTA AGGTTCCTTG ACAAAGATCC
 951 CCCTCGACGG TATCGATAAG CTCTAGAGTC AGGCACCGGG CTTGCGGGTC
1001 ATGCACCAGG TGCGCGGTCC TTCGGGCACC TCGACGTCGG CGGTGACGGT
1051 GAAGCCGAGC CGCTCGTAGA AGGGGAGGTT GCGGGGCGCG GAGGTCTCCA
1101 GGAAGGCGGG CACCCCGGCG CGCTCGGCCG CCTCCACTCC GGGGAGCACG
1151 ACGGCGCTGC CCAGACCCTT GCCCTGGTGG TCGGGCGAGA CGCCGACGGT
1201 GGCCAGGAAC CACGCGGGCT CCTTGGGGCG GTGCGGCGCC AGGAGGGCTT
1251 CCATCTGTTG CTGCGCGGCC AGCCGGGAAC CGCTCAACTC GGCCATGCGC
```

TABLE 7-continued

Sequences Listed in this Disclosure

```
1301 GGGCCGATCT CGGCGAACAC CGCCCCCGCT TCGACGCTCT CCGGCGTGGT

1351 CCAGACGGCC ACCGCGGCGC CGTGGTCCGC GACCCACACC TTGCCGATGT

1401 CGAGCCGGAC GCGCGTGAGG AAGAGTTCTT GCAGCTCGGT GACCCGCTCG

1451 ATGTGGCGGT CCGGGTCGAC GGTGTGGCGC GTGGCGGGGT AGTCGGCGAA

1501 CGCGGCGGCG AGGGTGCGTA GGGCCCGGGG GACGTCGTCG CGGGTGGCGA

1551 GGCGCACCGT GGGCTTGTAC TCGGTCATGG TTGTGGCAAG CTTATCATCG

1601 TGTTTTTCAA AGGAAAACCA CGTCCCCGTG GTTCGGGGGG CCTAGAGCTT

1651 TTTTAACCTC GACTAAACAC ATGTAAAGCA TGTGCACCGA GGCCCCAGAT

1701 CAGATTCCCA TACAATGGGG TACCTTCTGG GCATCCTTGA GCCCCTTGTT

1751 GACTACGCTT GAGGAGAGCC ATTTGACTCT TTCCACAAGT ATCCAACTCA

1801 CAACGTGGCA CTGGGGTTGT GCCGCCTTTG CAGGTGTATC TTATACACGT

1851 GGCTTTTGGC CGCAGAGGCA CCTGTCGCCA GGTGGGGGGT TCCGCTGCCT

1901 GCAAAGGGTC GCTACAGACG TTGTTTGTCT TCAAGAAGCT TCCAGAGGAA

1951 CTGCTTCCTT CACGACATTC AACAGACCTT GCATTCCTTT GGCGAGAGGG

2001 GAAAGACCCC TAGGAATGCT CGTCAAGAAG ACAGGGCCAG GTTTCCGGGC

2051 CCTCACATTG CCAAAAGACG GCAATATGGT GGAAAATCAC ATATAGACAA

2101 ACACACACCG GCCTTATTCC AAGCGGCTTC GGCCAGTAAC GTTAGGGGGG

2151 GGGGAGGGAG AGGGGCGGAA TTAGCTTGAT ATCGAATTCC GGCCGCGTCC

2201 CATCAGTCCA GGATGGTCTT GAAGTGTGAG GGCAGTGCCG GGTTGGCTGC

2251 GGCCTCCAGG GCAGTCAGCG TCGTCCCCGG GAGCTTCCGA CTCAGCTGCG

2301 TCTGGGCTGT CCTGAGTGAC CCCAGGAGTG GCACGTAGGT GACACGGTGT

2351 CGAGTCAGCT TGAGCAGGAA TGCTTGGTGG CACAGCCACT GCACGGCCTC

2401 GGAGGGCAGA GGGCCGGCGG CGCCCTTGGC CCCCAGCGAC ATCCCTGCGT

2451 TCTTGGCTTT CAGGATGGAG TAGCAGAGGG AGGCCGTGTC AGAGATGACG

2501 CGCAGGAAAA ATGTGGGGTT CTTCCAAACT TGCTGATGAA ATGGGAGCTG

2551 CAGCACACAT GCGTGAAACC TGTACGCCTG CAGCAGGAGG ATCTTGTAGA

2601 TGTTGGTGCA CACCGTCTGG AGGCTGTTCA CCTGCAAATC CAGAAACAGG

2651 CTGTGACACT TCAGCCGCAA GACCCCAAAG AGTTTGCGAC GCATGTTCCT

2701 CCCAGCCTTG AAGCCGCGGT TGAAGGTGAC ACTGGCTCTG ATGGAGGTCC

2751 GGGCATAGCT GGAGTAGTCG CTCTGCACCT CCAGGGTCCG GGTATCCAGC

2801 AGCAGGCCGC ACCAGGGGAA TAGGCCGTGG GCCGGCATCT GAACAAAAGC

2851 CGTGCCACCC AGGGCCTCGT CTTCTACAGG GAAGTTCACC ACTGTCTTCC

2901 GCAAGTTCAC CACGCAGCCA TACTCAGGGA CACCTCGGAC CAGGGTCCTG

2951 AGGAAGGTTT TCGCGTGGGT GAGGTGAGGT GTCACCAACA AGAAATCATC

3001 CACCAAACGC AGGAGCAGCC CGTCCCGCCG AATCCCCGCA AACAGCTTGT

3051 TCTCCATGTC GCCGTAGCAC AGGCTGCAGA GCAGCGTGGA GAGGATGGAG

3101 CCCTGCGGGA TCCGCTGGCA CTGGACGTAG GACTTGCCCC TGATGCGCAC

3151 GGCGTGGTGG CACATGAAGC GTAGGAAGAC GTCGAAGAGG CCACTGCTGG

3201 CCTCATTCAG GGAGGAGCTC TGCTCGATGA CGACGGCATC CCTCAGCGGG
```

TABLE 7-continued

Sequences Listed in this Disclosure

```
3251 CTGGTCTCCT GCAGGTGAGC CACGAACTGT CGCATGTACG GCTGGAGGTC

3301 TGTCAAGGTA GAGACGTGGC TCTTGAAGGC CTTGCGGACG TGCCCATGGG

3351 CGGCCTTCTG GACCACGGCA TACCGACGCA CGCAGTACGT GTTCTGGGGT

3401 TTGATGATGC TGGCGATGAC CTCCGTGAGC CTGTCCTGGG GGATGGTGTC

3451 GTACGCGCCC GTCACATCCA CCTTGACAAA GTACAGCTCA GGCGGCGGGT

3501 CCTGGGCCCG CACACGCAGC ACGAAGGTGC GCCAGGCCCT GTGGATATCG

3551 TCCAGGCCCA GCACAGAGGC GCCCAGGAGG CCGGGCGCC GCGCCCGCTC

3601 GTAGTTGAGC ACGCTGAACA GTGCCTTCAC CCTCGAGGTG AGACGCTCGG

3651 CCCTCTTTTC TCTGCGGAAC GTTCTGGCTC CCACGACGTA GTCCATGTTC

3701 ACAATCGGCC GCAGCCCGTC AGGCTTGGGG ATGAAGCGGA GTCTGGACGT

3751 CAGCAGGGCG GGCCTGGCTT CCCGATGCTG CCTGACCTCT GCTTCCGACA

3801 GCTCCCGCAG CTGCACCCTC TTCAAGTGCT GTCTGATTCC AATGCTTTGC

3851 AACTTGCTCC AGACACTCGG CCGGTAGAAA AAGAGCCTGT TCTTTTGAAA

3901 CGTGGTCTCC GTGACATAAA AGAAAGACCT GAGCAGCTCG ACGACGTACA

3951 CACTCATCAG CCAGTGCAGG AACTTGGCCA GGATCTCCTC ACGCAGACGG

4001 TGCTCTGCGG CCGGAACACA GCCAACCCCT GGGCTCCTGC GCAGCCAAGC

4051 GCAGTCCCGC ACGCTCATCT TCCACGTCAG CTCCTGCAGC GAGAGCTTGG

4101 CATGCTTCCC CAGGGAGATG AACTTCTTGG TGTTCCTGAG GAAGCGGCGT

4151 TCGTTGTGCC TGGAGCCCCA GAGGCCTGGG GGCACCAGCC GGCGCAGGCA

4201 GGCCCGCACG AAGCCGTACA CCTGCCAGGG GCTGCTGTGC TGGCGGAGCA

4251 GCTGCACCAG GCGACGGGGG TCTGTGTCCT CCTCCTCGGG GGCCGCCACA

4301 GAGCCCTGGG GCTTCTCCCG GCACAGACA CCGGCTGCTG GGGTGACCGC

4351 AGCTGGCAGC GGGCAGTGCG TCTTGAGGAG CACCCCGTAG GGGCACTGCG

4401 CGTGGTTCCC AAGCAGCTCC AGAAACAGGG GCCGCATTTG CCAGTAGCGC

4451 TGGGGCAGGC GGGGCAACCT GCGGGAGTC CCTGGCATCC AGGGCCTGGA

4501 ACCCAGAAAG ATGGTCTCCA CGAGCCTCCG AGCGCCAGTC AGGCTGGGCC

4551 TCAGAGAGCT GAGTAGGAAG GAGGGCCGCA GCTGCTCCTT GTCGCCTGAG

4601 GAGTAGAGGA AGTGCTTGGT CTCGGCGTAC ACCGGGGAC AAGGCGTGTC

4651 CCAGGGACGT GGTGGCCGCG ATGTGGATGG GGGGCCCGCG TGGTGCTGGC

4701 GGCCCACGGA TGGGTGGGAG TGGCGCGTGC CAGAGAGCGC ACCCTCCAAA

4751 GAGGTGGCTT CTTCGGCGGG TCTGGCAGGT GACACCACAC AGAAACCACG

4801 GTCACTCGGT CCACGCGTCC TGCCCGGGTG GGCCCAGGAC CCCTGCCCAA

4851 CGGGCGTCCG CTCCGGCTCA GGGGCAGCGC CACGCCTGGG CCTCTTGGGC

4901 AACGGCAGAC TTCGGCTGGC ACTGCCCCCG CGCCTCCTCG CACCCGGGGC

4951 TGGCAGGCCC AGGGGACCC CGGCCTCCCT GACGCTATGG TTCCAGGCCC

5001 GTTCGCATCC CAGACGCCTT CGGGGTCCAC TAGCGTGTGG CGGGGGCCGG

5051 GCCTGAGTGG CAGCGCCGAG CTGGTACAGC GGCGGCCCGC ACACCTGGTA

5101 GGCGGAGCTG GGAGCCACCA GCAGAAAGAG CGCGCAGCGT GCCAGCAGGT
```

TABLE 7-continued

Sequences Listed in this Disclosure

```
5151 GAACCAGCAC GTCGTCGCCC ACGCGGCGCA GCAGCAGCCC CCACGCCCCG

5201 GTCCCCCGCA GTGCGTCGGT CACCGTGTTG GGCAGGTAGC TGCGCACGCT

5251 GGTGGTGAAG GCCTCGGGGG GGCCCCCGCG GGCCCCGTCC AGCAGCGCGA

5301 AGCCGAAGGC CAGCACGTTC TTCGCGCCGC GCTCGCACAG CCTCTGCAGC

5351 ACTCGGGCCA CGAGCTCCTT CAGGCAGGAC ACCTGGCGGA AGGAGGGGGC

5401 GGCGGGGGGC GGCCGTGCGT CCCAGGGCAC GCACACCAGG CACTGGGCCA

5451 CCAGCGCGCG GAAAGCCGCC GGGTCCCCGC GCTGCACCAG CCGCCAGCCC

5501 TGGGGCCCCA GGCGCCGCAC GAACGTGGCC AGCGGCAGCA CCTCGCGGTA

5551 GTGGCTGCGC AGCAGGGAGC GCACGGCTCG GCAGCGGGGA GCGCGCGGCA

5601 TGGTGGAATT CCGATCCGGG ACCTGAAATA AAGACAAAA AGACTAAACT

5651 TACCAGTTAA CTTTCTGGTT TTTGAGTTCC TCGAGATCAA TTCGAGCTCG

5701 GTACCCGGGC GACGCAGTCT ATCGGAGGAC TGGCGCGCCG AGTGAGGGGT

5751 TGTGGGCTCT TTTATTGAGC TCGGGGAGCA GAAGCGCGCG AACAGAAGCG

5801 AGAAGCGAAC TGATTGGTTA GTTCAAATAA GGCACAGGGT CATTTCAGGT

5851 CCTTGGGGCA CCCTGGAAAC ATCTGATGGT TCTCTAGAAA CTGCTGAGGG

5901 CGGGACCGCA TCTGGGACC ATCTGTTCTT GGCGGTGAGC CGGGGCAGGA

5951 ACTGCTTACC ACAGATATCC TGTTTGGCCC ATATTCTGCT GTTCCAACTG

6001 TTCTTGGCCC TGAGCCGGGG CAGGAACTGC TTACCACAGA TATCCTGTTT

6051 GGCCCATATT CTGCTGTCTC TCTGTTCCTA ACCTTGATCT GAACTTCTCT

6101 ATTCTCAGTT ATGTATTTTC CATGCCTTGC AAAATGGCGT TACTTAAGCT

6151 AGCTTGCCAA ACCTACAGGT GGGGTCTTTC ATTCCCCCCT TTTTCTGGAG

6201 ACTAAATAAA ATCTTTTATT CTATCTATGG CTCGTACTCT ATAGGCTTCA

6251 GCTGGTGATA TTGTTGAGTC AAAACTAGAG CCAATCTGGT GATATTGTTG

6301 AGTCAAAACT AGAGCCTGGA CCACTGATAT CCTGTCTTTA ACAAATTGGA

6351 CTAATCGCTT AGCCCGGGGG ATCCACTAGT TCTAGAGCGG CCAATTCATA

6401 ACTTCGTATA GCATACATTA TACGAAGTTA TCGTCGACCA CGTGAGATCT

6451 GCCGGTCTCC CTATAGTGAG TCGTATTAAT TTCGATAAGC CAGGTTAACC

6501 TGCATTAATG AATCGGCCAA CGCGCGGGGA GAGGCGGTTT GCGTATTGGG

6551 CGCTCTTCCG CTTCCTCGCT CACTGACTCG CTGCGCTCGG TCGTTCGGCT

6601 GCGGCGAGCG GTATCAGCTC ACTCAAAGGC GGTAATACGG TTATCCACAG

6651 AATCAGGGGA TAACGCAGGA AAGAAGATGT GAGCAAAAGG CCAGCAAAAG

6701 GCCAGGAACC GTAAAAAGGC CGCGTTGCTG GCGTTTTTCC ATAGGCTCCG

6751 CCCCCCTGAC GAGCATCACA AAAATCGACG CTCAAGTCAG AGGTGGCGAA

6801 ACCCGACAGG ACTATAAAGA TACCAGGCGT TTCCCCCTGG AAGCTCCCTC

6851 GTGCGCTCTC CTGTTCCGAC CCTGCCGCTT ACCGGATACC TGTCCGCCTT

6901 TCTCCCTTCG GGAAGCGTGG CGCTTTCTCA TAGCTCACGC TGTAGGTATC

6951 TCAGTTCGGT GTAGGTCGTT CGCTCCAAGC TGGGCTGTGT GCACGAACCC

7001 CCCGTTCAGC CCGACCGCTG CGCCTTATCC GGTAACTATC GTCTTGAGTC

7051 CAACCCGGTA AGACACGACT TATCGCCACT GGCAGCAGCC AGTGGTAACA
```

TABLE 7-continued

Sequences Listed in this Disclosure

```
7101 GGATTAGCAG AGCGAGGTAT GTAGGCGGTG CTACAGAGTT CTTGAAGTGG

7151 TGGCCTAACT ACGGCTACAC TAGAAGAACA GTATTTGGTA TCTGCGCTCT

7201 GCTGAAGCCA GTTACCTTCG GAAAAAGAGT TGGTAGCTCT TGATCCGGCA

7251 AACAAACCAC CGCTGGTAGC GGTGGTTTTT TTGTTTGCAA GCAGCAGATT

7301 ACGCGCAGAA AAAAGGATC TCAAGAAGAT CCTTTGATCT TTTCTACGGG

7351 GTCTGACGCT CAGTGGAACG AAAACTCACG TTAAGGGATT TTGGTCATGA

7401 GATTATCAAA AAGGATCTTC ACCTAGATCC TTTTAAATTA AAAATGAAGT

7451 TTTAAATCAA TCTAAAGTAT ATATGAGTAA ACTTGGTCTG ACAGTTACCA

7501 ATGCTTAATC AGTGAGGCAC CTATCTCAGC GATCTGTCTA TTTCGTTCAT

7551 CCATAGTTGC CTGACTCCCC GTCGTGTAGA TAACTACGAT ACGGGAGGGC

7601 TTACCATCTG GCCCCAGTGC TGCAATGATA CCGCGAGACC CACGCTCACC

7651 GGCTCCAGAT TTATCAGCAA TAAACCAGCC AGCCGGAAGG GCCGAGCGCA

7701 GAAGTGGTCC TGCAACTTTA TCCGCCTCCA TCCAGTCTAT TAATTGTTGC

7751 CGGGAAGCTA GAGTAAGTAG TTCGCCAGTT AATAGTTTGC GCAACGTTGT

7801 TGCCATTGCT ACAGGCATCG TGGTGTCACG CTCGTCGTTT GGTATGGCTT

7851 CATTCAGCTC CGGTTCCCAA CGATCAAGGC GAGTTACATG ATCCCCCATG

7901 TTGTGCAAAA AAGCGGTTAG CTCCTTCGGT CCTCCGATCG TTGTCAGAAG

7951 TAAGTTGGCC GCAGTGTTAT CACTCATGGT TATGGCAGCA CTGCATAATT

8001 CTCTTACTGT CATGCCATCC GTAAGATGCT TTTCTGTGAC TGGTGAGTAC

8051 TCAACCAAGT CATTCTGAGA ATAGTGTATG CGGCGACCGA GTTGCTCTTG

8101 CCCGGCGTCA ATACGGGATA ATACCGCGCC ACATAGCAGA ACTTTAAAAG

8151 TGCTCATCAT TGGAAAACGT TCTTCGGGGC GAAAACTCTC AAGGATCTTA

8201 CCGCTGTTGA GATCCAGTTC GATGTAACCC ACTCGTGCAC CCAACTGATC

8251 TTGAGCATCT TTTACTTTCA CCAGCGTTTC TGGGTGAGCA AAAACAGGAA

8301 GGCAAAATGC CGCAAAAAAG GGAATAAGGG CGACACGGAA ATGTTGAATA

8351 CTCATACTCT TCCTTTTTCA ATATTATTGA AGCATTTATC AGGGTTATTG

8401 TCTCATGAGC GGATACATAT TTGAATGTAT TTAGAAAAAT AAACAAATAG

8451 GGGTTCCGCG CACATTTCCC CGAAAAGTGC CACCTGACGT CTAAGAAACC

8501 ATTATTATCA TGACATTAAC CTATAAAAAT AGGCGTATCA CGAGGCCCTT

8551 TCGTCTCGCG CGTTTCGGTG ATGACGGTGA AAACGTCTGA CACATGCAGC

8601 TCCCGGAGAC GGTCACAGCT TGTCTGTAAG CGGATGCCGG GAGCAGACAA

8651 GCCCGTCAGG GCGCGTCAGC GGGTGTTGGC GGGTGTCGGG GCTGGCTTAA

8701 CTATGCGGCA TCAGAGCAGA TTGTACTGAG AGTGCACCAT ATG
```

What is claimed as the invention is:

1. A method for generating transgenic non-primate mammals by nuclear transfer cormprising:
   a) genetically modifying a non-primate mammalian, nuclear donor cell with a vector comprising a telomerase reverse transcriptase (TERT) encoding region flanked on either side by sequences that are complementary to genomic DNA sequences in the donor cell so that homologous recombination of the vector into a target gene of the DNA causes the TERT region to be expressed in the cell;
   b) transferring the donor nucleus into an enucleated, unactivated, metaphase II-arrested oocyte of the same species to produce a reconstituted embryo;
   c) activating the reconstituted embryo;
   d) transferring the activated embryo into a female of the same species; and
   e) permitting development of the embryo to term.

2. The method of claim 1, wherein the TERT encoding region in the vector is flanked on either side by recognition sites for a site-specific recombinase.

3. The method of claim 1, wherein homologous recombination of the vector into the locus renders an endogenous gene in the cell inactive.

4. The method of claim 1, wherein homologous recombination of the vector into the cell cause the TERT in the vector to be expressed under the control of an endogenous promoter.

5. The method of claim 4, wherein the vector further comprises a second encoding region, wherein homologous recombination of the vector into the locus causes the second encoding region to be expressed in the cell.

6. The method of claim 5, wherein the second encoding region encodes an antibiotic resistance gene.

7. The method of claim 6, wherein the antibiotic resistance gene is flanked on either side by recognition sites for a site-specific recombinanse.

8. The method of claim 1, wherein the TERT is human telomerase reverse transcriptase.

9. A method for generating transgenic non-primate mammals by nuclear transfer comprising:
   a) genetically modifying a non-primate mammalian, nuclear donor cell with a vector comprising a telomerase reverse transcriptase (TERT) encoding region flanked on either side by sequences that are complementary to genomic DNA sequences in the donor cell so that homologous recombination of the vector into a target gene of the DNA causes the TERT region to be expressed in the cell;
   b) fusing the donor cell to an enucleated, unactivated, metaphase II-arrested oocyte of the same species to produce a reconstituted embryo;
   c) activating the reconstituted embryo;
   d) transferring the activated embryo into a female of the same species; and
   e) permitting development of the embryo to term.

10. The method of claim 9, wherein the TERT encoding region in the vector is flanked on either side by recognition sites for a site-specific recombinase.

11. The method of claim 9, wherein homologous recombination of the vector into the locus renders an endogenous gene in the cell inactive.

12. The method of claim 9, wherein homologous recombination of the vector into the cell cause the TERT in the vector to be expressed under the control of an endogenous promoter.

13. The method of claim 12, wherein the vector further comprises a second encoding region, wherein homologous recombination of the vector into the locus causes the second encoding region to be expressed in the cell.

14. The method of claim 13, wherein the second encoding region encodes an antibiotic resistance gene.

15. The method of claim 14, wherein the antibiotic resistance gene is flanked on either side by recognition sites for a site-specific recombinase.

16. The method of claim 9, wherein the TERT is human telomerase reverse transcriptase.

17. A method for generating transgenic non-primate mammals by nuclear transfer comprising:
   a) genetically modifying a non-primate mammalian, nuclear donor cell with a vector comprising a telomerase reverse transcriptase (TERT) encoding region flanked on either side by sequences that are complementary to genomic DNA sequences in the donor cell so that homologous recombination of the vector into a target gene of the DNA causes the TERT region to be expressed in the cell;
   b) transferring the donor nucleus into an activated, enucleated oocyte of the same species to produce a reconstituted embryo;
   c) transferring the reconstituted embryo into a female of the same species; and
   d) permitting development of the embryo to term.

18. The method of claim 17, wherein the TERT encoding region in the vector is flanked on either side by recognition sites for a site-specific recombinase.

19. The method of claim 17, wherein homologous recombination of the vector into the locus renders an endogenous gene in the cell inactive.

20. The method of claim 17, wherein homologous recombination of the vector into the cell cause the TERT in the vector to be expressed under the control of an endogenous promoter.

21. The method of claim 20, wherein the vector further comprises a second encoding region, wherein homologous recombination of the vector into the locus causes the second encoding region to be expressed in the cell.

22. The method of claim 21, wherein the second encoding region encodes an antibiotic resistance gene.

23. The method of claim 22, wherein the antibiotic resistance gene is flanked on either side by recognition sites for a site-specific recombinase.

24. The method of claim 17, wherein the TERT is human telomerase reverse transcriptase.

25. A method for generating transgenic non-primate mammals by nuclear transfer comprising:
   a) genetically modifying a non-primate mammalian, nuclear donor cell with a vector comprising a telomerase reverse transcriptase (TERT) encoding region flanked on either side by sequences that are complementary to genomic DNA sequences in the donor cell so that homologous recombination of the vector into a target gene of the DNA causes the TERT region to be expressed in the cell;
   b) fusing the donor cell to an activated, enucleated oocyte of the same species to produce a reconstituted embryo;
   c) transferring the reconstituted embryo into a female of the same species; and
   e) permitting development of the embryo to term.

26. The method of claim 25, wherein the TERT encoding region in the vector is flanked on either side by recognition sites for a site-specific recombinase.

27. The method of claim 25, wherein homologous recombination of the vector into the locus renders an endogenous gene in the cell inactive.

28. The method of claim 25, wherein homologous recombination of the vector into the cell cause the TERT in the vector to be expressed under the control of an endogenous promoter.

29. The method of claim 28, wherein the vector further comprises a second encoding region, wherein homologous recombination of the vector into the locus causes the second encoding region to be expressed in the cell.

30. The method of claim 29, wherein the second encoding region encodes an antibiotic resistance gene.

31. The method of claim 30, wherein the antibiotic resistance gene is flanked on either side by recognition sites for a site-specific recombinanse.

32. The method of claim 25, wherein the TERT is human telomerase reverse transcriptase.

* * * * *

UNITED STATES PATENT AND TRADEMARK OFFICE
CERTIFICATE OF CORRECTION

PATENT NO. : 7,265,262 B2 Page 1 of 1
APPLICATION NO. : 10/105616
DATED : September 4, 2007
INVENTOR(S) : A. John Clark et al.

It is certified that error appears in the above-identified patent and that said Letters Patent is hereby corrected as shown below:

On the title page, item (54), line 2, replace "ON" with -- OF --.

Signed and Sealed this

Fourth Day of December, 2007

JON W. DUDAS
*Director of the United States Patent and Trademark Office*

SEQUENCE LISTING

<160> NUMBER OF SEQ ID NOS: 33

<210> SEQ ID NO 1
<211> LENGTH: 13766
<212> TYPE: DNA
<213> ORGANISM: Artificial Sequence
<220> FEATURE:
<223> OTHER INFORMATION: Artificial construct comprising human TERT,
      myeloproliferative sa rcoma virus (MPSV) promoter, and vector
      components

<400> SEQUENCE: 1

| | | | | | |
|---|---|---|---|---|---|
| tgatcctcta | gagtcggtgg | gcctcggggg | cgggtgcggg | gtcggcgggg | ccgccccggg | 60 |
| tggcttcggt | cggagccatg | gggtcgtgcg | ctcctttcgg | tcgggcgctg | cgggtcgtgg | 120 |
| ggcgggcgtc | aggcaccggg | cttgcgggtc | atgcaccagg | tcgcgcggtc | cttcgggcac | 180 |
| tcgacgtcgg | cggtgacggt | gaagccgagc | cgctcgtaga | aggggaggtt | gcggggcgcg | 240 |
| gaggtctcca | ggaaggcggg | caccccggcg | cgctcggccg | cctccactcc | ggggagcacg | 300 |
| acggcgctgc | ccagacccct | gccctggtgg | tcgggcgaga | cgccgacggt | ggccaggaac | 360 |
| cacgcgggct | ccttgggccg | gtgcggcgcc | aggaggcctt | ccatctgttg | ctgcgcggcc | 420 |
| agccgggaac | cgctcaactc | ggccatgcgc | gggccgatct | cggcgaacac | cgccccgct | 480 |
| tcgacgctct | ccggcgtggt | ccagaccgcc | accgcggcgc | cgtcgtccgc | gacccacacc | 540 |
| ttgccgatgt | cgagcccgac | gcgcgtgagg | aagagttctt | gcagctcggt | gacccgctcg | 600 |
| atgtggcggt | cagggtccac | tgtatggcgt | gttgcagggt | agtcggcgaa | cgcggcggcg | 660 |
| agggtgcgta | cggcccgggg | gacgtcgtcg | cgggtggcga | ggcgcaccgt | gggcttgtac | 720 |
| tcggtcatgg | aaggtcgtct | ccttgtgagg | ggtcaggggc | gtgggtcagg | ggatggtggc | 780 |
| ggcaccggtc | gtggcggccg | acggcctcca | aaaaagcctc | ctcactactt | ctggaatagc | 840 |
| tcagaggccg | aggcggcctc | ggcctctgca | taaataaaaa | aaattagtca | gccatggggc | 900 |
| ggagaatggg | cggaactggg | cggagttagg | ggcgggatgg | gcggagttag | gggcgggact | 960 |
| atggttgctg | actaattgag | atgcatgctt | tgcatacttc | tgcctgctgg | ggagcctggg | 1020 |
| gactttccac | acctggttgc | tgactaattg | agatgcatgc | tttgcatact | tctgcctgct | 1080 |
| ggggagcctg | gggactttcc | acaccctaac | tgacacacat | tccacagcct | ggcgcgcgag | 1140 |
| atccagacat | gataagatac | attgatgagt | ttggacaaac | cacaactaga | atgcagtgaa | 1200 |
| aaaaatgctt | tatttgtgaa | atttgtgatg | ctattgcttt | atttgtaacc | attataagct | 1260 |
| gcaataaaca | agttaacaac | aacaattgca | ttcattttat | gtttcaggtt | caggggagg | 1320 |
| tgtgggaggt | tttttaaagc | aagtaaaacc | tctacaaatg | tggtatggct | gattatgatc | 1380 |
| tctagtcaag | gcactataca | tcaaatattc | cttattaacc | cctttacaaa | ttaaaaagct | 1440 |
| aaaggtacac | aattttgag | catagttatt | aatagcagac | actctatgcc | tgtgtggagt | 1500 |
| aagaaaaaac | agtatgttat | gattataact | gttatgccta | cttataaagg | ttacagaata | 1560 |
| tttttccata | attttcttgt | atagcagtgc | agctttttcc | tttgtggtgt | aaatagcaaa | 1620 |
| gcaagcaaga | gttctattac | taaacacagc | atgactcaaa | aaacttagca | attctgaagg | 1680 |
| aaagtccttg | ggtcttcta | cctttctctt | cttttttgga | ggagtagaat | gttgagagtc | 1740 |
| agcagtagcc | tcatcatcac | tagatggcat | ttcttctgag | caaaacaggt | tttcctcatt | 1800 |
| aaaggcattc | caccactgct | cccattcatc | agttccatag | gttggaatct | aaaatacaca | 1860 |
| aacaattaga | atcagtagtt | taacacatta | tacacttaaa | aattttatat | ttaccttata | 1920 |

-continued

| | |
|---|---|
| gctttaaatc tctgtaggta gtttgtccaa ttatgtcaca ccacagaagt aaggttcctt | 1980 |
| cacaaagatc taaagccagc aaaagtccca tggtcttata aaaatgcata gctttaggag | 2040 |
| gggagcagag aacttgaaag catcttcctg ttagtctttc ttctcgtaga cttcaaactt | 2100 |
| atacttgatg cctttttcct cctggacctc agagaggacg cctgggtatt ctgggagaag | 2160 |
| tttatatttc cccaaatcaa tttctgggaa aaacgtgtca ctttcaaatt cctgcatgat | 2220 |
| ccttgtcaca aagagtctaa ggtggcctgg ttgattcatg gcttcctggt aaacagaact | 2280 |
| gcctccgact atccaaacca tgtctacttt acttgccaat tccggttgtt caataagtct | 2340 |
| taaggcatca tccaaacttt tggcaagaaa atgagctcct cgtggtggtt ctttgagttc | 2400 |
| tctactgaga actatattaa ttctgtcctt taaaggtcga ttcttctcag gaatggagaa | 2460 |
| ccaggttttc ctacccataa tcaccagatt ctgtttacct tccactgaag aggttgtggt | 2520 |
| cattctttgg aagtacttga actcgttcct gagcggaggc cagggtaggt ctccgttctt | 2580 |
| gccaatcccc atattttggg acacggcgac gatgcagttc aatggtcgaa ccatgatggc | 2640 |
| agcggggata aaatcctacc agccttcacg ctaggattgc cgtcaagttt ggcgcgaaat | 2700 |
| cgcagccctg agctgtcccc ccccccaagc tatttgccaa agcctgggcc tccaaaaaag | 2760 |
| cctcctcact acttctggaa tagctcagag gccgaggcgg cctcggcctc tgcataaata | 2820 |
| aaaaaaatta gtcagccatg gggcggagaa tgggcggaac tgggcggagt tagggcggg | 2880 |
| atgggcggag ttaggggcgg gactatggtt gctgactaat tgagatgcat gctttgcata | 2940 |
| cttctgcctg ctggggagcc tggggacttt ccacacctgg ttgctgacta attgagatgc | 3000 |
| atgctttgca tacttctgcc tgctggggag cctggggact ttccacaccc taactgacac | 3060 |
| acattccaca gatcccgcaa gaggcccggc agtaccggca taaccaagcc tatgcctaca | 3120 |
| gcatccaggg tgacggtgcc gaggatgacg atgagcgcat tgttagattt catacacggt | 3180 |
| gcctgactgc gttagcaatt taactgtgat aaactaccgc attaaagcta agcgattagt | 3240 |
| ccaatttgtt aaagacagga tatcagtggt ccaggctcta gttttgactc aacaatatca | 3300 |
| ccagattggc tctagttttg actcaacaat atcaccagct gaagcctata gagtacgagc | 3360 |
| catagataga ataaaagatt ttatttagtc tccagaaaaa gggggaatg aaagacccca | 3420 |
| cctgtaggtt tggcaagcta gcttaagtaa cgccattttg caaggcatgg aaaatacata | 3480 |
| actgagaata gagaagttca gatcaaggtt aggaacagag agacagcaga atatgggcca | 3540 |
| aacaggatat ctgtggtaag cagttcctgc cccggctcag ggccaagaac agttggaaca | 3600 |
| gcagaatatg ggccaaacag gatatctgtg gtaagcagtt cctgccccgg ctcagggcca | 3660 |
| agaacagatg gtccccagat gcggtccgc cctcagcagt ttctagagaa ccatcagatg | 3720 |
| tttccagggt gccccaagga cctgaaatga ccctgtgcct tatttgaact aaccaatcag | 3780 |
| ttcgcttctc gcttctgttc gcgcgcttct gctccccgag ctcaataaaa gagcccacaa | 3840 |
| cccctcactc ggcgcgccag tcctccgata gactgcgtcg cccgggtacc gagctcgaat | 3900 |
| tgatctcgag gaactgaaaa accagaaagt taactggtaa gtttagtctt tttgtctttt | 3960 |
| atttcaggtc ccggatcgga attccaccat gccgcgcgct cccgctgcc gagccgtgcg | 4020 |
| ctccctgctg cgcagccact accgcgaggt gctgccgctg gccacgttcg tgcggcgcct | 4080 |
| ggggcccag ggctggcggc tggtgcagcg cggggacccg gcggctttcc gcgcgctggt | 4140 |
| ggcccagtgc ctggtgtgcg tgccctggga cgcacggccg ccccccgccg cccctcctt | 4200 |
| ccgccaggtg tcctgcctga aggagctggt ggcccgagtg ctgcagaggc tgtgcgagcg | 4260 |

-continued

```
cggcgcgaag aacgtgctgg ccttcggctt cgcgctgctg gacggggccc gcggggggccc      4320 ccccgaggcc ttcaccacca gcgtgcgcag ctacctgccc aacacggtga ccgacgcact      4380 gcggggggagc gggcgtggg ggctgctgct cgccgcgtg ggcgacgacg tgctggttca      4440
cctgctggca cgctgcgcgc tctttgtgct ggtggctccc agctgcgcct accaggtgtg      4500
cgggccgccg ctgtaccagc tcggcgctgc cactcaggcc cggccccgc cacacgctag      4560 tggaccccga aggcgtctgg gatgcgaacg ggcctggaac catagcgtca gggaggccgg      4620 ggtcccctg ggcctgccag ccccgggtgc gaggaggcgc ggggggcagtg ccagccgaag      4680 tctgccgttg cccaagaggc ccaggcgtgg cgctgcccct gagccggagc ggacgcccgt      4740
tgggcagggg tcctgggccc acccgggcag gacgcgtgga ccgagtgacc gtggtttctg      4800
tgtggtgtca cctgccagac ccgccgaaga agccacctct ttggagggtg cgctctctgg      4860
cacgcgccac tcccacccat ccgtgggccg ccagcaccac gcgggccccc catccacatc      4920
gcggccacca cgtccctggg acacgccttg tcccccggtg tacgccgaga ccaagcactt      4980
cctctactcc tcaggcgaca aggagcagct gcggccctcc ttcctactca gctctctgag      5040
gcccagcctg actggcgctc ggaggctcgt ggagaccatc tttctgggtt ccaggccctg      5100
gatgccaggg actccccgca ggttgccccg cctgccccag cgctactggc aaatgcggcc      5160
cctgtttctg gagctgcttg gaaccacgc gcagtgcccc tacggggtgc tcctcaagac      5220
gcactgcccg ctgcgagctg cggtcacccc agcagccggt gtctgtgccc gggagaagcc      5280
ccagggctct gtggcggccc ccgaggagga ggacacagac cccgtcgcc tggtgcagct      5340 gctccgccag cacagcagcc cctggcaggt gtacggcttc gtgcgggcct gcctgcgccg      5400
gctggtgccc ccaggcctct ggggctccag gcacaacgaa cgccgcttcc tcaggaacac      5460
caagaagttc atctccctgg ggaagcatgc caagctctcg ctgcaggagc tgacgtggaa      5520
gatgagcgtg cgggactgcg cttggctgcg caggagccca ggggttggct gtgttccggc      5580
cgcagagcac cgtctgcgtg aggagatcct ggccaagttc ctgcactggc tgatgagtgt      5640
gtacgtcgtc gagctgctca ggtctttctt ttatgtcacg gagaccacgt ttcaaaagaa      5700 caggctctttt ttctaccggc cgagtgtctg gagcaagttg caaagcattg gaatcagaca      5760
gcacttgaag agggtgcagc tgcgggagct gtcggaagca gaggtcaggc agcatcggga      5820
agccaggccc gccctgctga cgtccagact ccgcttcatc cccaagcctg acgggctgcg      5880
gccgattgtg aacatggact acgtcgtggg agccagaacg ttccgcagag aaaagagggc      5940
cgagcgtctc acctcgaggg tgaaggcact gttcagcgtg ctcaactacg agcgggcgcg      6000 gcgcccccggc ctcctgggcg cctctgtgct gggcctggac gatatccaca gggcctggcg      6060
caccttcgtg ctgcgtgtgc gggcccagga cccgccgcct gagctgtact ttgtcaaggt      6120
ggatgtgacg ggcgcgtacg acaccatccc ccaggacagg ctcacggagg tcatcgccag      6180
catcatcaaa ccccagaaca cgtactgcgt gcgtcggtat gccgtggtcc agaaggccgc      6240
ccatgggcac gtccgcaagg ccttcaagag ccacgtctct accttgacag acctccagcc      6300
gtacatgcga cagttcgtgg ctcacctgca ggagaccagc ccgctgaggg atgccgtcgt      6360
catcgagcag agctcctccc tgaatgaggc cagcagtggc ctcttcgacg tcttcctacg      6420
cttcatgtgc caccacgccg tgcgcatcag gggcaagtcc tacgtccagt gccagggggat      6480 cccgcagggc tccatcctct ccacgctgct ctgcagcctg tgctacggcg acatggagaa      6540
caagctgttt gcgggattc ggcgggacgg gctgctcctg cgtttggtgg atgatttctt      6600
gttggtgaca cctcacctca cccacgcgaa aaccttcctc aggaccctgg tccgaggtgt      6660
```

```
ccctgagtat ggctgcgtgg tgaacttgcg aagacagtg gtgaacttcc ctgtagaaga    6720
cgaggccctg ggtggcacgg cttttgttca gatgccggcc cacggcctat tccctggtg    6780
cggcctgctg ctggataccc ggaccctgga ggtgcagagc gactactcca gctatgcccg    6840
gacctccatc agagccagtg tcaccttcaa ccgcggcttc aaggctggga ggaacatgcg    6900
tcgcaaaactc tttggggtct tgcggctgaa gtgtcacagc ctgtttctgg atttgcaggt   6960
gaacagcctc cagacggtgt gcaccaacat ctacaagatc ctcctgctgc aggcgtacag    7020
gtttcacgca tgtgtgctgc agctcccatt tcatcagcaa gtttggaaga accccacatt    7080
tttcctgcgc gtcatctctg acacggcctc cctctgctac tccatcctga agccaagaa    7140
cgcaggatg tcgctggggg ccaagggcgc cgccggccct ctgccctccg aggccgtgca    7200
gtggctgtgc caccaagcat tcctgctcaa gctgactcga caccgtgtca cctacgtgcc    7260
actcctgggg tcactcagga cagcccgac gcagctgagt cggaagctcc cggggacgac    7320
gctgactgcc ctggaggccg cagccaaccc ggcactgccc tcagacttca agaccatcct    7380
ggactgatgg gacgcggccg ctctagaact agtggatccc ccgggctgca ggaattctca    7440
cgtgcggatc cacctaggtg tcgacctgca ggtcgcgaag cttcgatcca gacatgataa    7500
gatacattga tgagtttgga caaaccacaa ctagaatgca gtgaaaaaaa tgctttattt    7560
gtgaaatttg tgatgctatt gctttatttg taaccattat aagctgcaat aaacaagtta    7620
acaacaacaa ttgcattcat tttatgtttc aggttcaggg ggaggtgtgg gaggttttttt   7680
aaagcaagta aaacctctac aaatgtggta tggctgatta tgatccggct gcctcgcgcg    7740
tttcggtgat gacggtgaaa acctctgaca catgcagctc ccggagacgg tcacagcttg    7800
tctgtaagcg gatgccggga gcagacaagc ccgtcagggc gcgtcagcgg gtgttggcgg    7860
gtgtcggggc gcagccatga cccagtcacg tagcgatagc ggagtgtatt cgagctcgga    7920
cattgattat tgactagtta ttaatagtaa tcaattacgg ggtcattagt tcatagccca    7980
tatatggagt tccgcgttac ataacttacg gtaaatggcc cgcctggctg accgcccaac    8040
gacccccgcc cattgacgtc aataatgacg tatgttccca tagtaacgcc aatagggact    8100
ttccattgac gtcaatgggt ggagtattta cggtaaactg cccacttggc agtacatcaa    8160
gtgtatcata tgccaagtac gccccctatt gacgtcaatg acggtaaatg gcccgcctgg    8220
cattatgccc agtacatgac cttatgggac tttcctactt ggcagtacat ctacgtatta    8280
gtcatcgcta ttaccatggt gatgcggttt tggcagtaca tcaatgggcg tggatagcgg    8340
tttgactcac ggggatttcc aagtctccac ccagcggacc ccgtccctaa cccacggggc    8400
ccgtggctat ggcagggcct gccgcccga cgttggctgc gagccctggg ccttcacccg    8460
aacttggggg gtggggtggg gaaaaggaag aaacgcgggc gtattggccc caatggggtc    8520
tcggtggggt atcgacagag tgccagccct gggaccgaac cccgcgttta tgaacaaacg    8580
acccaacacc cgtgcgtttt attctgtctt tttattgccg tcatagcgcg ggttccttcc    8640
ggtattgtct ccttccgtgt ttcagttagc ctcccccatc tccccagatc tgcacccaat    8700
cggcaggcac gggcggcgat ctccaatctg cgggatcagt cagatcaccc gagtgcgtgg    8760
gcatgacaat cgtgccctgg ggaccaacac aatccagaag ggcctgaatc actgcgaccg    8820
gccctcccgc gacccagccg agcgagctta gcgaactgtg gacgagaact gtgccaccaa    8880
gcgtaaggcc gttctctcgc atttgccttg ctaggctcgc gcgagttgct ggctgaggcg    8940
ttctcgaaat cagctcttgt tcggtcggca tctactctat tcctttgccc tcggacgagt    9000
```

```
gctgggcgt cggtttccac tatcggcgag tacttctaca cagccatcgg tccagacggc    9060
cgcgcttctg cgggcgattt gtgtacgccc gacagtcccg gctccggatc ggacgattgc    9120
gtcgcatcga ccctgcgccc aagctgcatc atcgaaattg ccgtcaacca agctctgata    9180
gagttggtca agaccaatgc ggagcatata cgcccggagc cgcggcgatc ctgcaagctc    9240
cggatgcctc cgctcgaagt agcgcgtctg ctgctccata caagccaacc acggcctcca    9300
gaagaagatg ttggcgacct cgtattggga atccccgaac atcgcctcgc tccagtcaat    9360
gaccgctgtt atgcggccat tgtccgtcag gacattgttg gagccgaaat ccgcgtgcac    9420
gaggtgccgg acttcggggc agtcctcggc ccaaagcatc agctcatcga gagcctgcgc    9480
gacggacgca ctgacggtgt cgtccatcac agtttgccag tgatacacat ggggatcagc    9540
aatcgcgcat atgaaatcac gccatgtagt gtattgaccg attccttgcg gtccgaatgg    9600
gccgaacccg ctcgtctggc taagatcggc cgcagcgatc gcatccatgg cctccgcgac    9660
cggctgcaga acagcgggca gttcggtttc aggcaggtct tgcaacgtga caccctgtgc    9720
acggcgggag atgcaatagg tcaggctctc gctgaactcc ccgatatcaa gcacttccgg    9780
aatcgggagc gcgccgatg caaagtgccg ataaacataa cgatctttgt agaaaccatc    9840
ggcgcagcta tttacccgca ggacatatcc acgccctcct acatcgaagc tgaaagcacg    9900
agattcttcg ccctccgaga gctgcatcag gtcggagacg ctgtcgaact tttcgatcag    9960
aaacttctcg acagacgtcg cggtgagttc aggctttttc atatctcccg gatctgcggc   10020
acgctgttga cgctgttaag cgggtcgctg cagggtcgct cggtgttcga ggccacacgc   10080
gtcaccttaa tatgcgaagt ggacctcgga ccgcgccgcc ccgactgcat ctgcgtgttc   10140
ggattcgcca atgacaagac gctgggcggg gtttgtgtca tcatagaact aaagacatgc   10200
aaatatattt cttccgggga caccgccagc aaacgcgagc aacgggccac ggggatgaag   10260
cagtaatgc ggtagtttat cacagttaaa ttgctaacgc agtcaggcac cgtgtatgaa   10320
atctaacaat gcgctcatcg tcatcctcgg caccgtcacc ctggatgctg taggcatagg   10380
cttggttatg ccggtactgc cgggcctctt gcgggatatc gtccattccg acagcatcgc   10440
cagtcactat ggcgtgctgc tagcgctata tgcgttgatg caatttctat gcgtaagagg   10500
ttccaacttt caccataatg aaataagatc actaccgggc gtattttttg agttatcgag   10560
attttcagga gctaaggaag ctaaaatgga gaaaaaatc actggatata ccaccgttga   10620
tatatcccaa tggcatcgta agaacattt tgaggcattt cagtcagttg ctcaatgtac   10680
ctataaccag accgttcagc tggatattac ggccttttta aagaccgtaa agaaaaataa   10740
gcacaagttt tatccggcct ttattcacat tcttgcccgc ctgatgaatg ctcatcccga   10800
gttccgtatg gcaatgaaag acggtgagct ggtgatatgg gatagtgttc acccttgtta   10860
caccgttttc catgagcaaa ctgaaacgtt ttcatcgctc tggagtgaat accacgacga   10920
tttccggcag tttctacaca tatattcgca agatgtggcg tgttacggtg aaaacctggc   10980
ctatttccct aaagggttta ttgagaatat gttttcgtc tcagccaatc cctgggtgag   11040
tttcaccagt tttgatttaa acgtggccaa tatggacaac ttcttcgccc ccgttttcac   11100
catgggcaaa tattatacgc aaggcgacaa ggtgctgatg ccgctggcga ttcaggttca   11160
tcatgccgtt tgtgatggct tccatgtcgg cagaatgctt aatgaattac aacagtgtac   11220
cgcatcaggc gaaattgtaa acgttaatat tttgttaaaa ttcgcgtaaa tatttgttaa   11280
atcagctcat ttttttaacca ataggccgaa atcggcaaaa tcccttataa atcaaaagaa   11340
tagaccgaga tagggttgag tgttgttcca gtttggaaca agagtccact attaaagaac   11400
```

```
gtggactcca acgtcaaagg gcgaaaaacc gtctatcagg gcgatggccc actacgtgaa    11460
ccatcaccca aatcaagttt tttgcggtcg aggtgccgta aagctctaaa tcggaaccct    11520
aaagggagcc cccgatttag agcttgacgg ggaaagccgg cgaacgtggc gagaaaggaa    11580
gggaagaaag cgaaaggagc gggcgctagg gcgctggcaa gtgtagcggt cacgctgcgc    11640
gtaaccacca cacccgccgc gcttaatgcg ccgctacagg gcgcgtccat tcgccattca    11700
ggctgcctgc attaatgaat cggccaacgc gcggggagag gcggtttgcg tattgggcgc    11760
tcttccgctt cctcgctcac tgactcgctg cgctcggtcg ttcggctgcg gcgagcggta    11820
tcagctcact caaaggcggt aatacggtta tccacagaat caggggataa cgcaggaaag    11880
aacatgtgag caaaaggcca gcaaaaggcc aggaaccgta aaaaggccgc gttgctggcg    11940 ttttccata ggctccgccc ccctgacgag catcacaaaa atcgacgctc aagtcagagg     12000
tggcgaaacc cgacaggact ataaagatac caggcgtttc ccctggaag ctccctcgtg     12060 cgctctcctg ttccgaccct gccgcttacc ggatacctgt ccgcctttct cccttcggga    12120
agcgtggcgc tttctcaatg ctcacgctgt aggtatctca gttcggtgta ggtcgttcgc    12180
tccaagctgg gctgtgtgca cgaaccccc gttcagcccg accgctgcgc cttatccggt      12240
aactatcgtc ttgagtccaa cccggtaaga cacgacttat cgccactggc agcagccact    12300
ggtaacagga ttagcagagc gaggtatgta ggcggtgcta cagagttctt gaagtggtgg    12360
cctaactacg gctacactag aaggacagta tttggtatct gcgctctgct gaagccagtt    12420
accttcggaa aaagagttgg tagctcttga tccggcaaac aaaccaccgc tggtagcggt    12480
ggtttttttg tttgcaagca gcagattacg cgcagaaaaa aaggatctca agaagatcct    12540
ttgatctttt ctacggggtc tgacgctcag tggaacgaaa actcacgtta agggattttg    12600
gtcatgagat tatcaaaaag gatcttcacc tagatccttt taaattaaaa atgaagtttt    12660
aaatcaatct aaagtatata tgagtaaact tggtctgaca gttaccaatg cttaatcagt    12720
gaggcaccta tctcagcgat ctgtctattt cgttcatcca tagttgcctg actccccgtc    12780
gtgtagataa ctacgatacg ggagggctta ccatctggcc ccagtgctgc aatgataccg    12840
cgagacccac gctcaccggc tccagattta tcagcaataa accagccagc cggaagggcc    12900
gagcgcagaa gtggtcctgc aactttatcc gcctccatcc agtctattaa ttgttgccgg    12960
gaagctagag taagtagttc gccagttaat agtttgcgca acgttgttgc cattgctgca    13020
ggcatcgtgg tgtcacgctc gtcgtttggt atggcttcat tcagctccgg ttcccaacga    13080
tcaaggcgag ttacatgatc ccccatgttg tgcaaaaaag cggttagctc cttcggtcct    13140
ccgatcgttg tcagaagtaa gttggccgca gtgttatcac tcatggttat ggcagcactg    13200
cataattctc ttactgtcat gccatccgta agatgctttt ctgtgactgg tgagtactca    13260
accaagtcat tctgagaata gtgtatgcgg cgaccgagtt gctcttgccc ggcgtcaaca    13320
cgggataata ccgcgccaca tagcagaact ttaaaagtgc tcatcattgg aaaacgttct    13380
tcggggcgaa aactctcaag gatcttaccg ctgttgagat ccagttcgat gtaacccact    13440
cgtgcaccca actgatcttc agcatctttt actttcacca gcgtttctgt ggtgaggaaa    13500
aacaggaagg caaaatgccg caaaaaaggg aataagggcg acacggaaat gttgaatact    13560
catactcttc cttttcaat attattgaag catttatcag ggttattgtc tcatgagcgg      13620
atacatattt gaatgtattt agaaaaataa acaaataggg gttccgcgca catttccccg     13680
aaaagtgcca cctgacgtct aagaaaccat tattatcatg acattaacct ataaaaatag     13740
```

```
                                               -continued gcgtatcacg aggcccttte gtcttc                                                13766

<210> SEQ ID NO 2
<211> LENGTH: 1303
<212> TYPE: DNA
<213> ORGANISM: Ovis sp.
<220> FEATURE:
<221> NAME/KEY: CDS
<222> LOCATION: (194)..(1303)
<223> OTHER INFORMATION:

<400> SEQUENCE: 2
agccgaggac gccgccgggg agccgaggct ccggccagcc cccagcgcgc ccagcttctg         60
cagatcagga gtcagaacgc tgcaccttcg cttcctccca gccctgcctc cttctgcaaa        120
acggagctca atagaacttg gtacttttgc cttttactct gggaggagag aagcagacga        180
tgaggagaaa ata atg aat gtc aaa gga aaa gtg att ctg tca atg ctg          229
             Met Asn Val Lys Gly Lys Val Ile Leu Ser Met Leu
               1               5                  10 gtt gtc tca act gtc att gtt gtg ttt tgg gaa tat atc cac agc cca          277
Val Val Ser Thr Val Ile Val Val Phe Trp Glu Tyr Ile His Ser Pro
         15                  20                  25 gaa ggc tct ttg ttc tgg ata aac cca tca aga aac cca gaa gtc agt          325
Glu Gly Ser Leu Phe Trp Ile Asn Pro Ser Arg Asn Pro Glu Val Ser
 30                  35                  40 ggc ggc agc agc att cag aag ggc tgg tgg ttt ccg aga tgg ttt aac          373
Gly Gly Ser Ser Ile Gln Lys Gly Trp Trp Phe Pro Arg Trp Phe Asn
 45                  50                  55                  60 aat ggt tac caa gaa gaa gat gaa gac gta gac gaa gaa aag gaa caa          421
Asn Gly Tyr Gln Glu Glu Asp Glu Asp Val Asp Glu Glu Lys Glu Gln
                 65                  70                  75 aga aag gaa gac aaa agc aag ctt aag cta tcg gac tgg ttc aac cca          469
Arg Lys Glu Asp Lys Ser Lys Leu Lys Leu Ser Asp Trp Phe Asn Pro
             80                  85                  90 ttt aaa cgc cct gag gtt gtg act atg aca gat tgg aag gca ccc gtg          517
Phe Lys Arg Pro Glu Val Val Thr Met Thr Asp Trp Lys Ala Pro Val
         95                 100                 105 gtg tgg gaa ggc act tac aac aga gcc gtc tta gac gat tac tac gcc          565
Val Trp Glu Gly Thr Tyr Asn Arg Ala Val Leu Asp Asp Tyr Tyr Ala
    110                 115                 120 aag cag aaa att acc gtc ggc ctg acg gtt ttc gcc gtc gga aga tac          613
Lys Gln Lys Ile Thr Val Gly Leu Thr Val Phe Ala Val Gly Arg Tyr
125                 130                 135                 140 att gag cat tac ttg gag gag ttc tta acg tct gct aat aag cac ttc          661
Ile Glu His Tyr Leu Glu Glu Phe Leu Thr Ser Ala Asn Lys His Phe
                145                 150                 155 atg gtt ggc cac cga gtc atc ttt tac gtc atg gtg gac gac gtc tcc          709
Met Val Gly His Arg Val Ile Phe Tyr Val Met Val Asp Asp Val Ser
            160                 165                 170 agg atg cct ttg ata gag ctg ggc cct ctg cgc tcc ttc aaa gtg ttt          757
Arg Met Pro Leu Ile Glu Leu Gly Pro Leu Arg Ser Phe Lys Val Phe
        175                 180                 185 gag gtc aag cct gag agg agg tgg cag gac gtc agc atg gtg cgc atg          805
Glu Val Lys Pro Glu Arg Arg Trp Gln Asp Val Ser Met Val Arg Met
    190                 195                 200 aag acc atc ggg gag cac atc gtg gcc cac atc cag cgt gag gtt gac          853
Lys Thr Ile Gly Glu His Ile Val Ala His Ile Gln Arg Glu Val Asp
205                 210                 215                 220 ttc ctc ttc tgc atg gac gtg gac cag gtc ttc caa gac gag ttc ggg          901
Phe Leu Phe Cys Met Asp Val Asp Gln Val Phe Gln Asp Glu Phe Gly
                225                 230                 235
```

-continued

```
gtg gag acc ctg ggt gag tcg gtg gcc cag cta cag gcc tgg tgg tac      949
Val Glu Thr Leu Gly Glu Ser Val Ala Gln Leu Gln Ala Trp Trp Tyr
            240                 245                 250 aag gca gat ccc gat gag ttt acc tac gag agg cgc aag gag tct gca      997
Lys Ala Asp Pro Asp Glu Phe Thr Tyr Glu Arg Arg Lys Glu Ser Ala
            255                 260                 265 gca tac att ccc ttc ggc gaa ggg gat ttt tat tac cac gca gcc att     1045
Ala Tyr Ile Pro Phe Gly Glu Gly Asp Phe Tyr Tyr His Ala Ala Ile
        270                 275                 280 ttt ggg gga aca ccc act cag gtc ctt aac atc acc cag gaa tgc ttc     1093
Phe Gly Gly Thr Pro Thr Gln Val Leu Asn Ile Thr Gln Glu Cys Phe
285                 290                 295                 300 aaa gga atc ctc aag gac aag aaa aat gac ata gaa gcc caa tgg cat     1141
Lys Gly Ile Leu Lys Asp Lys Lys Asn Asp Ile Glu Ala Gln Trp His
                305                 310                 315 gat gag agc cat cta aac aag tat ttc ctt ctc aac aaa ccc act aaa     1189
Asp Glu Ser His Leu Asn Lys Tyr Phe Leu Leu Asn Lys Pro Thr Lys
            320                 325                 330 atc tta tcc ccg gaa tac tgc tgg gat tat cat ata ggc cta cct gcg     1237
Ile Leu Ser Pro Glu Tyr Cys Trp Asp Tyr His Ile Gly Leu Pro Ala
            335                 340                 345 gat att aag ctt gtc aag atg tct tgg cag aca aaa gag tat aat gtg     1285
Asp Ile Lys Leu Val Lys Met Ser Trp Gln Thr Lys Glu Tyr Asn Val
        350                 355                 360 gtt aga aat aac gtc tga                                             1303
Val Arg Asn Asn Val
365

<210> SEQ ID NO 3
<211> LENGTH: 369
<212> TYPE: PRT
<213> ORGANISM: Ovis sp.

<400> SEQUENCE: 3

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Ser Gly Gly Ser Ser
        35                  40                  45

Ile Gln Lys Gly Trp Trp Phe Pro Arg Trp Phe Asn Asn Gly Tyr Gln
    50                  55                  60

Glu Glu Asp Glu Asp Val Asp Glu Lys Glu Gln Arg Lys Glu Asp
65                  70                  75                  80

Lys Ser Lys Leu Lys Leu Ser Asp Trp Phe Asn Pro Phe Lys Arg Pro
                85                  90                  95

Glu Val Val Thr Met Thr Asp Trp Lys Ala Pro Val Val Trp Glu Gly
            100                 105                 110

Thr Tyr Asn Arg Ala Val Leu Asp Asp Tyr Tyr Ala Lys Gln Lys Ile
        115                 120                 125

Thr Val Gly Leu Thr Val Phe Ala Val Gly Arg Tyr Ile Glu His Tyr
    130                 135                 140

Leu Glu Glu Phe Leu Thr Ser Ala Asn Lys His Phe Met Val Gly His
145                 150                 155                 160

Arg Val Ile Phe Tyr Val Met Val Asp Asp Val Ser Arg Met Pro Leu
                165                 170                 175

Ile Glu Leu Gly Pro Leu Arg Ser Phe Lys Val Phe Glu Val Lys Pro
```

```
                    180                 185                 190
Glu Arg Arg Trp Gln Asp Val Ser Met Val Arg Met Lys Thr Ile Gly
        195                 200                 205

Glu His Ile Val Ala His Ile Gln Arg Glu Val Asp Phe Leu Phe Cys
    210                 215                 220

Met Asp Val Asp Gln Val Phe Gln Asp Glu Phe Gly Val Glu Thr Leu
225                 230                 235                 240

Gly Glu Ser Val Ala Gln Leu Gln Ala Trp Trp Tyr Lys Ala Asp Pro
                245                 250                 255

Asp Glu Phe Thr Tyr Glu Arg Arg Lys Glu Ser Ala Ala Tyr Ile Pro
            260                 265                 270

Phe Gly Glu Gly Asp Phe Tyr Tyr His Ala Ala Ile Phe Gly Gly Thr
        275                 280                 285

Pro Thr Gln Val Leu Asn Ile Thr Gln Glu Cys Phe Lys Gly Ile Leu
    290                 295                 300

Lys Asp Lys Lys Asn Asp Ile Glu Ala Gln Trp His Asp Glu Ser His
305                 310                 315                 320

Leu Asn Lys Tyr Phe Leu Leu Asn Lys Pro Thr Lys Ile Leu Ser Pro
                325                 330                 335

Glu Tyr Cys Trp Asp Tyr His Ile Gly Leu Pro Ala Asp Ile Lys Leu
            340                 345                 350

Val Lys Met Ser Trp Gln Thr Lys Glu Tyr Asn Val Val Arg Asn Asn
        355                 360                 365

Val

<210> SEQ ID NO 4
<211> LENGTH: 4256
<212> TYPE: DNA
<213> ORGANISM: Ovis sp.
<220> FEATURE:
<221> NAME/KEY: CDS
<222> LOCATION: (72)..(842)
<223> OTHER INFORMATION:

<400> SEQUENCE: 4
ctgcagactt taagtgattc ttacgtgggc atttgatgct gacaccctct ttattttgca     60
gagaagtcat c atg gtg aaa agc cac ata ggc agt tgg atc ctg gtt ctc    110
            Met Val Lys Ser His Ile Gly Ser Trp Ile Leu Val Leu
              1               5                  10 ttt gtg gcc atg tgg agt gac gtg ggc ctc tgc aag aag cga cca aaa    158
Phe Val Ala Met Trp Ser Asp Val Gly Leu Cys Lys Lys Arg Pro Lys
         15                  20                  25 cct ggc gga gga tgg aac act ggg ggg agc cga tac ccg gga cag ggc    206
Pro Gly Gly Gly Trp Asn Thr Gly Gly Ser Arg Tyr Pro Gly Gln Gly
 30                  35                  40                  45 agt cct gga ggc aac cgc tat cca cct cag gga ggg ggt ggc tgg ggt    254
Ser Pro Gly Gly Asn Arg Tyr Pro Pro Gln Gly Gly Gly Gly Trp Gly
                 50                  55                  60 cag ccc cat gga ggt ggc tgg ggc caa cct cat gga ggt ggc tgg ggt    302
Gln Pro His Gly Gly Gly Trp Gly Gln Pro His Gly Gly Gly Trp Gly
             65                  70                  75 cag ccc cat ggt ggt ggc tgg gga cag cca cat ggt ggt gga ggc tgg    350
Gln Pro His Gly Gly Gly Trp Gly Gln Pro His Gly Gly Gly Gly Trp
         80                  85                  90 ggt caa ggt ggt agc cac agt cag tgg aac aag ccc agt aag cca aaa    398
Gly Gln Gly Gly Ser His Ser Gln Trp Asn Lys Pro Ser Lys Pro Lys
 95                 100                 105
```

```
acc aac atg aag cat gtg gca gga gct gct gca gct gga gca gtg gta    446
Thr Asn Met Lys His Val Ala Gly Ala Ala Ala Ala Gly Ala Val Val
110                 115                 120                 125 ggg ggc ctt ggt ggc tac atg ctg gga agt gcc atg agc agg cct ctt    494
Gly Gly Leu Gly Gly Tyr Met Leu Gly Ser Ala Met Ser Arg Pro Leu
            130                 135                 140 ata cat ttt ggc aat gac tat gag gac cgt tac tat cgt gaa aac atg    542
Ile His Phe Gly Asn Asp Tyr Glu Asp Arg Tyr Tyr Arg Glu Asn Met
                145                 150                 155 tac cgt tac ccc aac caa gtg tac tac aga cca gtg gat cgg tat agt    590
Tyr Arg Tyr Pro Asn Gln Val Tyr Tyr Arg Pro Val Asp Arg Tyr Ser
            160                 165                 170 aac cag aac aac ttt gtg cat gac tgt gtc aac atc aca gtc aag caa    638
Asn Gln Asn Asn Phe Val His Asp Cys Val Asn Ile Thr Val Lys Gln
        175                 180                 185 cac aca gtc acc acc acc acc aag ggg gag aac ttc acc gaa act gac    686
His Thr Val Thr Thr Thr Thr Lys Gly Glu Asn Phe Thr Glu Thr Asp
190                 195                 200                 205 atc aag ata atg gag cga gtg gtg gag caa atg tgc atc acc cag tac    734
Ile Lys Ile Met Glu Arg Val Val Glu Gln Met Cys Ile Thr Gln Tyr
                210                 215                 220 cag aga gaa tcc cag gct tat tac caa agg ggg gca agt gtg atc ctc    782
Gln Arg Glu Ser Gln Ala Tyr Tyr Gln Arg Gly Ala Ser Val Ile Leu
            225                 230                 235 ttt tct tcc cct cct gtg atc ctc ctc atc tct ttc ctc att ttt ctc    830
Phe Ser Ser Pro Pro Val Ile Leu Leu Ile Ser Phe Leu Ile Phe Leu
        240                 245                 250 ata gta gga tag gggcaacctt cctgttttca ttatcttctt aatctttgcc         882
Ile Val Gly
    255 aggttggggg agggagtgtc tacctgcagc cctgtagtgg tggtgtctca tttcttgctt    942 ctctcttgtt acctgtataa taataccctt ggcgcttaca gcactgggaa atgacaagca   1002 gacatgagat gctatttatt caagtcccat tagctcagta ttctaatgtc ccatcttagc   1062 agtgattttg tagcaatttt ctcatttgtt tcaagaacac ctgactacat ttcccttttgg  1122 gaatagcatt tctgccaagt ctggaaggag gccacataat attcattcaa aaaaacaaaa   1182 ctggaaatcc ttagttcata gacccagggt ccaccctgtt gagagcatgt gtcctgtgtc   1242 tgcagagaac tataaaggat attctgcatt ttgcaggtta catttgcagg taacacagcc   1302 atctattgca tcaagaatgg atattcatgc aacctttgac ttatgggcag aggacatctt   1362 cacaaggaat gaacataata caaaggcttc tgagactaaa aaattccaac atatggaaga   1422 ggtgccctttg gtggcagcct tccattttgt atgtttaaag caccttcaag tgatattcct   1482 ttctttagta acataaagta tagataatta aggtacctta attaaactac cttctagaca   1542 ctgagagcaa atctgttgtt tatctggaac ccaggatgat tttgacattg cttagggatg   1602 tgagagttgg actgtaaaga aagctgagtg ctgaagagtt catgctttttg aactatagtg   1662 ttggagaaaa ctcttgagag tcccttggac tgaaaggaga tcagtcctga atattcattg   1722 gaaggactga tgctgaagct gaaactccag tactttggtc acctgatggg aagaactgaa   1782 ggcaggaggg atgctaggaa agactgaagg caggaggaga aggggacgac agaggatgag   1842 atggctagat ggcatcatgg actcaatgga catgagctta agtaaactcc aggagttggc   1902 aatggacagg gagacctggc gtcctgcagt ccatggtgtc gcagagtcgg acacgattga   1962 gtgactaaat tgaggtgacc cagatttaac atagagaatg cagatacaaa actcatattc   2022 atttgattga atcttttcct gaaccagtgc tagtgttgga ctggtaaggg tataacagca   2082
```

```
tatataggtt atgtgatgaa gagatagtgt acatgaaata tgtgcatttc tttattgctg      2142
tcttataatt gtcaaaaaag aaaattaggt ccttggtttc tgtaaaattg acttgaatca      2202
aaagggaggc atttaaagaa ataaattaga gatgatagaa atctgatcca ttcagagtag      2262
aaaaagaaat tccattactg ttattaaaga aggtaaaatt attccctgaa ttgttcaata      2322
ttgtcaccta gcagatagac actattctgt actgttttta ctagcttgca ccttgtggta      2382
tcctatgtaa aaacatattt gcatatgaca aacttttttct gttagagcaa ttaacatctg      2442
aaccacctaa tgcattacct gttttttgtaa ggtacttttt gtaaggtact aaggagatgt      2502
gggtttaatc cctaggtcag gtaaatcccc tagaggaaga aatggcaacc cactccagta      2562
ttcttgccag gaaatccag tgggcagagg agcctggcag ggtacagtct gagcatgggg      2622
ttgcaaagag tgagacaaga cttgagctac tgaacaataa ggacaataaa tgctgggtcg      2682
gctaaaaggt tcattaggtt tttttttctgt aagatggctc tagtagtact tgtctttatc      2742
ttcattcgaa acaattttgt tagattgtat gtgacagctc ttgtatcagc atgcatttga      2802
aaaaaacatc acaattggta aattttttgta tagccatctt actattgaag atggaagaaa      2862
agaagcaaaa ttttcagcat atcatgctgt acttatttca agaaagataa ccaaaatgca      2922
aaaatgtatt tgtgaagtgt atggagaagg ggctgcaact gatcaagctt gtcaaagtag      2982
tttgtgaagt ttcgtgctgg agatttctta ttggacgatg ctccacagtt ggatatacca      3042
gttgaagttg atagtgatca aattgagata ttgagaataa tcgatgttat accacgcggg      3102
agatagctga catactcaaa atatccaaat agaaccttga aaaccatttg caccatctca      3162
gttatgttaa tcactttgat gtttgagttc cacataagca aaaaaacaac aacaaaaaaa      3222
aatacaacct tgaccatatt tgcgcatgca gttctctact gaaatgattg aaaacacttt      3282
gtttttaaaa acagattttg attaacagtg ggtacgatac aataacgtag atggaagaaa      3342
ttgtagggtg agcaaaatga accacaccac caaaggccag tcttcctcta aagaagatgt      3402
gtgtatggtg ggattggaaa gtaatcctct attatgaatt cttctggaaa acactgctcc      3462
taattagacc aactgaaaac agcactcaac gaaaagcatc cagaattagt caatagaaaa      3522
cataatcttc catcaggata acgcaagact acatatttct ttgatgaccc agcatggctg      3582
gagtttctga ttcatctgtt gtattcagac gttgcatctt tggatttttt ccatttattt      3642
cagtctacaa aattatcata atggaaaaaa tttccattcc ctggaagatg taaagtgcat      3702
ctggaaaatt tctttgctca aaaagataaa aagttttgtg aacacagaat tatgacgttg      3762
cctgaaaaat ggcagaaggt agtggaacaa aagagtgact atgttgtttg gtaaagttct      3822
tagtgaaaat gaaaaatgtg tcttttattt ttatttaaac accaaaggca cattttagca      3882
acccaatact gaatctaaag gaaactcttc tgtgtgttgt ccttacagtg tgcactgata      3942
gtttgtataa gaatccagag tgatatttga aatacgcatg tgcttatatt ttttatattt      4002
gtaactttgc atgtacttgt tttgtgttaa aagtttataa atatttaata tctgactaaa      4062
attaaacagg agctaaaagg agtatcttcc acggagttgt ctggctgtgt tcaccagatg      4122
tgcacacatg ttggcagctt catttggggg gttaatatga gaaaagtgac acattcagtc      4182
ctcacactgc caattgcagg aggagggcta ctcctgatcc tgcttcagcc ttattcccag      4242
tcacatgcca gctg                                                       4256
```

<210> SEQ ID NO 5
<211> LENGTH: 256
<212> TYPE: PRT

<213> ORGANISM: Ovis sp.

<400> SEQUENCE: 5

```
Met Val Lys Ser His Ile Gly Ser Trp Ile Leu Val Leu Phe Val Ala
1               5                   10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
        35                  40                  45
Gly Asn Arg Tyr Pro Pro Gln Gly Gly Gly Trp Gly Gln Pro His
50                  55                  60
Gly Gly Gly Trp Gly Gln Pro His Gly Gly Gly Trp Gly Gln Pro His
65                  70                  75                  80
Gly Gly Gly Trp Gly Gln Pro His Gly Gly Gly Trp Gly Gln Gly
                85                  90                  95
Gly Ser His Ser Gln Trp Asn Lys Pro Ser Lys Pro Lys Thr Asn Met
            100                 105                 110
Lys His Val Ala Gly Ala Ala Ala Gly Ala Val Val Gly Gly Leu
        115                 120                 125
Gly Gly Tyr Met Leu Gly Ser Ala Met Ser Arg Pro Leu Ile His Phe
    130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Arg Tyr Ser Asn Gln Asn
                165                 170                 175
Asn Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Ile
        195                 200                 205
Met Glu Arg Val Val Glu Gln Met Cys Ile Thr Gln Tyr Gln Arg Glu
    210                 215                 220
Ser Gln Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255
```

<210> SEQ ID NO 6
<211> LENGTH: 8742
<212> TYPE: DNA
<213> ORGANISM: Artificial Sequence
<220> FEATURE:
<223> OTHER INFORMATION: Artificial construct comprising human TERT, myeloproliferative sa rcoma virus (MPSV) promoter, and vector components

<400> SEQUENCE: 6

| | | | | | | |
|---|---|---|---|---|---|---|
| cggccgccgg | cagatctgat | cctgatcata | acttcgtata | gcatacatta | tacgaagtta | 60 |
| tcatgagatc | cgacctcgag | gccgctctag | aactagtgga | tccagacatg | ataagataca | 120 |
| ttgatgagtt | tggacaaacc | acaactagaa | tgcagtgaaa | aaaatgcttt | atttgtgaaa | 180 |
| tttgtgatgc | tattgcttta | tttgtaacca | ttataagctg | caataaacaa | gttaacaaca | 240 |
| acaattgcat | tcattttatg | tttcaggttc | aggggaggt | gtgggaggtt | ttttaaagca | 300 |
| agtaaaacct | ctacaaatgt | ggtatggctg | attatgatct | ctagtcaagg | cactatacat | 360 |
| caaatattcc | ttattaaccc | ctttacaaat | taaaaagcta | aggtacaca | attttttgagc | 420 |
| atagttatta | atagcagaca | ctctatgcct | gtgtggagta | agaaaaaaca | gtatgttatg | 480 |

```
attataactg ttatgcctac ttataaaggt tacagaatat ttttccataa ttttcttgta      540
tagcagtgca gcttttttcct ttgtggtgta aatagcaaag caagcaagag ttctattact     600
aaacacagca tgactcaaaa aacttagcaa ttctgaagga aagtccttgg ggtcttctac      660 cttttctcttc tttttttggag gagtagaatg ttgagagtca gcagtagcct catcatcact    720
agatggcatt tcttctgagc aaaacaggtt ttcctcatta aaggcattcc accactgctc      780
ccattcatca gttccatagg ttggaatcta aaatacacaa acaattagaa tcagtagttt      840
aacacattat acacttaaaa atttttatatt taccttagag ctttaaatct ctgtaggtag     900
tttgtccaat tatgtcacac cacagaagta aggttccttc acaaagatcc ccctcgacgg      960
tatcgataag ctctagagtc aggcaccggg cttgcgggtc atgcaccagg tgcgcggtcc     1020
ttcgggcacc tcgacgtcgg cggtgacggt gaagccgagc cgctcgtaga aggggaggtt    1080
gcggggcgcg gaggtctcca ggaaggcggg caccccggcg cgctcggccg cctccactcc    1140
ggggagcacg acggcgctgc ccagacccctt gccctggtgg tcgggcgaga cgccgacggt   1200
ggccaggaac cacgcgggct ccttgggccg gtgcggcgcc aggaggcctt ccatctgttg    1260
ctgcgcggcc agccgggaac cgctcaactc ggccatgcgc gggccgatct cggcgaacac    1320
cgcccccgct tcgacgctct ccggcgtggt ccagaccgcc accgcggcgc cgtcgtccgc    1380
gacccacacc ttgccgatgt cgagcccgac gcgcgtgagg aagagttctt gcagctcggt    1440
gacccgctcg atgtggcggt ccgggtcgac ggtgtggcgc gtggcggggt agtcggcgaa    1500
cgcggcggcg agggtgcgta cggcccgggg gacgtcgtcg cgggtggcga ggcgcaccgt    1560
gggcttgtac tcggtcatgg ttgtggcaag cttatcatcg tgttttttcaa aggaaaaacca  1620 cgtccccgtg gttcgggggg cctagagctt ttttaacctc gactaaacac atgtaaagca    1680
tgtgcaccga ggccccagat cagattccca tacaatgggg taccttctgg gcatccttca    1740 gcccccttgtt gactacgctt gaggagagcc atttgactct ttccacaact atccaactca   1800
caacgtggca ctgggttgt gccgcctttg caggtgtatc ttatacacgt ggcttttggc     1860
cgcagaggca cctgtcgcca ggtgggggt tccgctgcct gcaaagggtc gctacagacg     1920
ttgtttgtct tcaagaagct tccagaggaa ctgcttcctt cacgacattc aacagacctt    1980
gcattccttt ggcgagaggg gaaagacccc taggaatgct cgtcaagaag acagggccag    2040
gtttccgggc cctcacattg ccaaaagacg gcaatatggt ggaaaatcac atatagacaa    2100
acacacaccg gccttattcc aagcggcttc ggccagtaac gttagggggg ggggagggag    2160 agggcggaa ttagcttgat atcgaattcc ggccgcgtcc catcagtcca ggatggtctt     2220
gaagtctgag ggcagtgccg ggttggctgc ggcctccagg gcagtcagcg tcgtccccgg    2280
gagcttccga ctcagctgcg tctgggctgt cctgagtgac cccaggagtg cacgtaggt     2340 gacacggtgt cgagtcagct tgagcaggaa tgcttggtgg cacagccact gcacggcctc    2400
ggagggcaga gggccggcgg cgcccttggc ccccagcgac atccctgcgt tcttggcttt    2460
caggatggag tagcagaggg aggccgtgtc agagatgacg cgcaggaaaa atgtggggtt    2520
cttccaaact tgctgatgaa atgggagctg cagcacacat gcgtgaaacc tgtacgcctg    2580
cagcaggagg atcttgtaga tgttggtgca caccgtctgg aggctgttca cctgcaaatc    2640
cagaaacagg ctgtgacact tcagccgcaa gaccccaaag agtttgcgac gcatgttcct    2700
cccagccttg aagccgcggt tgaaggtgac actggctctg atggaggtcc gggcatagct    2760
ggagtagtcg ctctgcacct ccagggtccg ggtatccagc agcaggccgc accaggggaa    2820
```

```
taggccgtgg gccggcatct gaacaaaagc cgtgccaccc agggcctcgt cttctacagg    2880
gaagttcacc actgtcttcc gcaagttcac cacgcagcca tactcaggga cacctcggac    2940
cagggtcctg aggaaggttt tcgcgtgggt gaggtgaggt gtcaccaaca agaaatcatc    3000
caccaaacgc aggagcagcc cgtcccgccg aatccccgca aacagcttgt tctccatgtc    3060
gccgtagcac aggctgcaga gcagcgtgga gaggatggag ccctgcggga tccctggca    3120 ctggactag gacttgcccc tgatgcgcac ggcgtggtgg cacatgaagc gtaggaagac    3180
gtcgaagagg ccactgctgg cctcattcag ggaggagctc tgctcgatga cgacggcatc    3240
cctcagcggg ctggtctcct gcaggtgagc cacgaactgt cgcatgtacg gctggaggtc    3300
tgtcaaggta gagacgtggc tcttgaaggc cttgcggacg tgcccatggg cggccttctg    3360
gaccacggca taccgacgca cgcagtacgt gttctgggt tgatgatgc tggcgatgac    3420 ctccgtgagc ctgtcctggg ggatggtgtc gtacgcgccc gtcacatcca ccttgacaaa    3480
gtacagctca ggcggcgggt cctgggcccg cacacgcagc acgaaggtgc gccaggccct    3540
gtggatatcg tccaggccca gcacagaggc gcccaggagg ccggggcgcc gcgcccgctc    3600
gtagttgagc acgctgaaca gtgccttcac cctcgaggtg agacgctcgg ccctcttttc    3660
tctgcggaac gttctggctc ccacgacgta gtccatgttc acaatcggcc gcagcccgtc    3720
aggcttgggg atgaagcgga gtctggacgt cagcagggcg ggcctggctt cccgatgctg    3780
cctgacctct gcttccgaca gctcccgcag ctgcacccctc ttcaagtgct gtctgattcc    3840 aatgcttgc aacttgctcc agacactcgg ccggtagaaa aagagcctgt tcttttgaaa    3900
cgtggtctcc gtgacataaa agaaagacct gagcagctcg acgacgtacc actcatcagc    3960
cagtgcagga acttggccag gatctcctca cgcagacggt gctctgcggc cggaacacag    4020 ccaaccctg gctcctgcg cagccaagcg cagtcccgca cgctcatctt ccacgtcagc    4080
tcctgcagcg agagcttggc atgcttcccc agggagatga acttcttggt gttcctgagg    4140
aagcggcgtt cgttgtgcct ggagccccag aggcctgggg gcaccagccg gcgcaggcag    4200
gcccgcacga agccgtacac ctgccagggg ctgctgtgct ggcggagcag ctgcaccagg    4260 cgacggggt ctgtgtcctc ctcctcgggg gccgccacag agccctgggg cttctcccgg    4320
gcacagacac cggctgctgg ggtgaccgca gctcgcagcg ggcagtgcgt cttgaggagc    4380
accccgtagg ggcactgcgc gtggttccca agcagctcca gaaacagggg ccgcatttgc    4440
cagtagcgct ggggcaggcg gggcaacctg cggggagtcc ctggcatcca gggcctggaa    4500
cccagaaaga tggtctccac gagcctccga gcgccagtca ggctgggcct cagagagctg    4560
agtaggaagg agggccgcag ctgctccttg tcgcctgagg agtagaggaa gtgcttggtc    4620
tcggcgtaca ccgggggaca aggcgtgtcc cagggacgtg gtggccgcga tgtggatggg    4680
gggcccgcgt ggtgctggcg gcccacggat gggtgggagt ggcgcgtgcc agagagcgca    4740
ccctccaaag aggtggcttc ttcggcgggt ctggcaggtg acaccacaca gaaaccacgg    4800
tcactcggtc cacgcgtcct gcccgggtgg gcccaggacc cctgcccaac gggcgtccgc    4860
tccggctcag gggcagcgcc acgcctgggc tcttgggca acggcagact tcggctggca    4920 ctgccccgc gcctcctcgc acccggggct ggcaggccca gggggacccc ggcctccctg    4980
acgctatggt tccaggcccg ttcgcatccc agacgccttc ggggtccact agcgtgtggc    5040
gggggccggg cctgagtggc agcgccgagc tggtacagcg gcggcccgca cacctggtag    5100
gcgcagctgg gagccaccag cacaaagagc gcgcagcgtg ccagcaggtg aaccagcacg    5160
tcgtcgccca cgcggcgcag cagcagcccc cacgcccgc tcccccgcag tgcgtcggtc    5220
```

```
accgtgttgg gcaggtagct gcgcacgctg gtggtgaagg cctcggggggg gccccccgcgg    5280 gccccgtcca gcagcgcgaa gccgaaggcc agcacgttct tcgcgccgcg ctcgcacagc    5340
ctctgcagca ctcgggccac cagctccttc aggcaggaca cctggcggaa ggaggggggcg    5400 gcgggggggcg gccgtgcgtc ccagggcacg cacaccaggc actgggccac cagcgcgcgg    5460
aaagccgccg ggtccccgcg ctgcaccagc cgccagccct ggggcccccag gcgccgcacg    5520 aacgtggcca gcggcagcac ctcgcggtag tggctgcgca gcagggagcg cacggctcgg    5580
cagcggggag cgcgcggcat ggtggaattc cgatccggga cctgaaataa aagacaaaaa    5640
gactaaactt accagttaac tttctggttt ttcagttcct cgagatcaat tcgagctcgg    5700
tacccgggcg acgcagtcta tcggaggact ggcgcgccga gtgagggggtt gtgggctctt    5760 ttattgagct cggggagcag aagcgcgcga acagaagcga gaagcgaact gattggttag    5820
ttcaaataag gcacagggtc atttcaggtc cttgggcac cctggaaaca tctgatggtt    5880
ctctagaaac tgctgagggc gggaccgcat ctggggacca tctgttcttg gccctgagcc    5940
ggggcaggaa ctgcttacca cagatatcct gtttggccca tattctgctg ttccaactgt    6000
tcttggccct gagccggggc aggaactgct taccacagat atcctgtttg cccatattc    6060 tgctgtctct ctgttcctaa ccttgatctg aacttctcta ttctcagtta tgtatttttcc    6120 atgccttgca aaatggcgtt acttaagcta gcttgccaaa cctacaggtg gggtctttca    6180
ttcccccctt tttctggaga ctaaataaaa tcttttattc tatctatggc tcgtactcta    6240
taggcttcag ctggtgatat tgttgagtca aaactagagc caatctggtg atattgttga    6300
gtcaaaacta gagcctggac cactgatatc ctgtctttaa caaattggac taatcgctta    6360
gcccggggga tccactagtt ctagagcggc caattcataa cttcgtatag catacattat    6420
acgaagttat cgtcgaccac gtgagatctg ccggtctccc tatagtgagt cgtattaatt    6480
tcgataagcc aggttaacct gcattaatga atcggccaac gcgcggggag aggcggtttg    6540
cgtattgggc gctcttccgc ttcctcgctc actgactcgc tgcgctcggt cgttcggctg    6600
cggcgagcgg tatcagctca ctcaaaggcg gtaatacggt tatccacaga atcagggggat    6660 aacgcaggaa agaacatgtg agcaaaaggc cagcaaaagg ccaggaaccg taaaaaggcc    6720
gcgttgctgg cgtttttcca taggctccgc ccccctgacg agcatcacaa aaatcgacgc    6780
tcaagtcaga ggtggcgaaa cccgacagga ctataaagat accaggcgtt tcccctggaa    6840
agctccctcg tgcgctctcc tgttccgacc ctgccgctta ccggatacct gtccgccttt    6900
ctcccttcgg gaagcgtggc gctttctcat agctcacgct gtaggtatct cagttcggtg    6960
taggtcgttc gctccaagct gggctgtgtg cacgaacccc ccgttcagcc cgaccgctgc    7020
gccttatccg gtaactatcg tcttgagtcc aacccggtaa gacacgactt atcgccactg    7080
gcagcagcca ctggtaacag gattagcaga gcgaggtatg taggcggtgc tacagagttc    7140
ttgaagtggt ggcctaacta cggctacact agaagaacag tatttggtat ctgcgctctg    7200
ctgaagccag ttaccttcgg aaaaagagtt ggtagctctt gatccggcaa acaaaccacc    7260
gctggtagcg gtggtttttt tgtttgcaag cagcagatta cgcgcagaaa aaaggatct    7320 caagaagatc ctttgatctt ttctacgggg tctgacgctc agtggaacga aaactcacgt    7380
taagggattt tggtcatgag attatcaaaa aggatcttca cctagatcct tttaaattaa    7440
aaatgaagtt ttaaatcaat ctaaagtata tatgagtaaa cttggtctga cagttaccaa    7500
tgcttaatca gtgaggcacc tatctcagcg atctgtctat ttcgttcatc catagttgcc    7560
```

```
tgactcccg  tcgtgtagat  aactacgata  cgggagggct  taccatctgg  ccccagtgct    7620
gcaatgatac  cgcgagaccc  acgctcaccg  gctccagatt  tatcagcaat  aaaccagcca    7680
gccggaaggg  ccgagcgcag  aagtggtcct  gcaactttat  ccgcctccat  ccagtctatt    7740
aattgttgcc  gggaagctag  agtaagtagt  tcgccagtta  atagtttgcg  caacgttgtt    7800
gccattgcta  caggcatcgt  ggtgtcacgc  tcgtcgtttg  gtatggcttc  attcagctcc    7860
ggttcccaac  gatcaaggcg  agttacatga  tcccccatgt  tgtgcaaaaa  agcggttagc    7920
tccttcggtc  ctccgatcgt  tgtcagaagt  aagttggccg  cagtgttatc  actcatggtt    7980
atggcagcac  tgcataattc  tcttactgtc  atgccatccg  taagatgctt  ttctgtgact    8040
ggtgagtact  caaccaagtc  attctgagaa  tagtgtatgc  ggcgaccgag  ttgctcttgc    8100
ccggcgtcaa  tacgggataa  taccgcgcca  catagcagaa  ctttaaaagt  gctcatcatt    8160
ggaaaacgtt  cttcggggcg  aaaactctca  aggatcttac  cgctgttgag  atccagttcg    8220
atgtaaccca  ctcgtgcacc  caactgatct  tcagcatctt  ttactttcac  cagcgtttct    8280
gggtgagcaa  aaacaggaag  gcaaaatgcc  gcaaaaaagg  gaataagggc  gacacggaaa    8340
tgttgaatac  tcatactctt  cctttttcaa  tattattgaa  gcatttatca  gggttattgt    8400
ctcatgagcg  gatacatatt  tgaatgtatt  tagaaaaata  aacaaatagg  ggttccgcgc    8460
acatttcccc  gaaaagtgcc  acctgacgtc  taagaaacca  ttattatcat  gacattaacc    8520
tataaaaata  ggcgtatcac  gaggcccttt  cgtctcgcgc  gtttcggtga  tgacggtgaa    8580
aacctctgac  acatgcagct  cccggagacg  gtcacagctt  gtctgtaagc  ggatgccggg    8640
agcagacaag  cccgtcaggg  cgcgtcagcg  ggtgttggcg  ggtgtcgggg  ctggcttaac    8700
tatgcggcat  cagagcagat  tgtactgaga  gtgcaccata  tg                       8742
```

<210> SEQ ID NO 7
<211> LENGTH: 19
<212> TYPE: DNA
<213> ORGANISM: Artificial Sequence
<220> FEATURE:
<223> OTHER INFORMATION: oligonucleotide probe

<400> SEQUENCE: 7
gggaggaagc gaaggtgca                                          19

<210> SEQ ID NO 8
<211> LENGTH: 22
<212> TYPE: DNA
<213> ORGANISM: Artificial Sequence
<220> FEATURE:
<223> OTHER INFORMATION: oligonucleotide probe

<400> SEQUENCE: 8
cttgatgggt ttatccagaa ca                                      22

<210> SEQ ID NO 9
<211> LENGTH: 20
<212> TYPE: DNA
<213> ORGANISM: Artificial Sequence
<220> FEATURE:
<223> OTHER INFORMATION: oligonucleotide probe

<400> SEQUENCE: 9
tgataatccc agcagtattc                                         20

<210> SEQ ID NO 10
<211> LENGTH: 36

```
<212> TYPE: DNA
<213> ORGANISM: Artificial Sequence
<220> FEATURE:
<223> OTHER INFORMATION: primer

<400> SEQUENCE: 10
acgtggctcc aagaattctc caggcaagag tactgg                            36

<210> SEQ ID NO 11
<211> LENGTH: 49
<212> TYPE: DNA
<213> ORGANISM: Artificial Sequence
<220> FEATURE:
<223> OTHER INFORMATION: primer

<400> SEQUENCE: 11
catcttgttc aatggccgat cccattattt tctcctggga aagaaaag              49

<210> SEQ ID NO 12
<211> LENGTH: 49
<212> TYPE: DNA
<213> ORGANISM: Artificial Sequence
<220> FEATURE:
<223> OTHER INFORMATION: primer

<400> SEQUENCE: 12
cttttctttt cccaggagaa aataatggga tcggccattg aacaagatg             49

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
caggtcgacg gatccgaaca aac                                          23

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
acgtggctcc aagaattctc caggcaagag tactgg                            36

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
gcgcaccgtg ggcttgtact cggtcattat tttctcctgg gaaaagaaaa             50

<210> SEQ ID NO 16
<211> LENGTH: 34
<212> TYPE: DNA
<213> ORGANISM: Artificial Sequence
<220> FEATURE:
<223> OTHER INFORMATION: primer

<400> SEQUENCE: 16
```
gagaaaataa tgaccgagta caagcccacg gtgc                                34

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17
ctggggatcc agacatgata agatac                                          26

<210> SEQ ID NO 18
<211> LENGTH: 32
<212> TYPE: DNA
<213> ORGANISM: Artificial Sequence
<220> FEATURE:
<223> OTHER INFORMATION: primer

<400> SEQUENCE: 18
ccgagctcgc caatttcatg gctgcagtca cc                                   32

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
cgatcccatg atgacttctc tgcaaaataa ag                                   32

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
gagaagtcat catgggatcg gccattgaac a                                    31

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tgcaggtcga cggatccgaa                                                 20

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cagctgtgtg ggtatgggag gg                                              22

<210> SEQ ID NO 23
<211> LENGTH: 27
<212> TYPE: DNA
<213> ORGANISM: Artificial Sequence

```
<220> FEATURE:
<223> OTHER INFORMATION: primer

<400> SEQUENCE: 23
ctgaactgaa tgtttatcca ggccatc                                          27

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
agccgattgt ctgttgtgcc cagtcat                                          27

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
ttcagtcgct ctgttgtgtc cca                                              23

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
agcatccctc ctgccttcag ttcttc                                           26

<210> SEQ ID NO 27
<211> LENGTH: 110
<212> TYPE: DNA
<213> ORGANISM: Artificial Sequence
<220> FEATURE:
<223> OTHER INFORMATION: oligonucleotide probe

<400> SEQUENCE: 27
gatcccagct gtgtgggtat gggagggaaa ggccacctgg gaaatggttg ggtctcaatt      60
gtaaaagacc agcatgcttt ctgctctgaa cggcggagca cgtagttagg               110

<210> SEQ ID NO 28
<211> LENGTH: 110
<212> TYPE: DNA
<213> ORGANISM: Artificial Sequence
<220> FEATURE:
<223> OTHER INFORMATION: oligonucleotide probe

<400> SEQUENCE: 28
gatccctaac tacgtgctcc gccgttcaga gcagaaagca tgctggtctt ttacaattga      60
gacccaacca tttcccaggt ggcctttccc tcccataccc acacagctgg               110

<210> SEQ ID NO 29
<211> LENGTH: 23
<212> TYPE: DNA
<213> ORGANISM: Artificial sequence
<220> FEATURE:
<223> OTHER INFORMATION: probes and primers
```

```
<400> SEQUENCE: 29
ttcagtcgct ctgttgtgtc cca                                              23

<210> SEQ ID NO 30
<211> LENGTH: 26
<212> TYPE: DNA
<213> ORGANISM: Artificial sequence
<220> FEATURE:
<223> OTHER INFORMATION: probes and primers

<400> SEQUENCE: 30
agcatccctc ctgccttcag ttcttc                                           26

<210> SEQ ID NO 31
<211> LENGTH: 27
<212> TYPE: DNA
<213> ORGANISM: Artificial sequence
<220> FEATURE:
<223> OTHER INFORMATION: probes and primers

<400> SEQUENCE: 31
agccgattgt ctgttgtgcc cagtcat                                          27

<210> SEQ ID NO 32
<211> LENGTH: 25
<212> TYPE: DNA
<213> ORGANISM: Artificial sequence
<220> FEATURE:
<223> OTHER INFORMATION: probes and primers

<400> SEQUENCE: 32
caaaagaact agttccccaa taaac                                            25

<210> SEQ ID NO 33
<211> LENGTH: 25
<212> TYPE: DNA
<213> ORGANISM: Artificial sequence
<220> FEATURE:
<223> OTHER INFORMATION: probes and primers

<400> SEQUENCE: 33
taacaaattt tacttgctgc ttgtg                                            25
```